United States Patent
Gunderson et al.

(10) Patent No.: US 11,970,734 B2
(45) Date of Patent: *Apr. 30, 2024

(54) COMPOSITIONS, SYSTEMS, AND METHODS FOR SEQUENCING POLYNUCLEOTIDES USING TETHERS ANCHORED TO POLYMERASES ADJACENT TO NANOPORES

(71) Applicant: Illumina, Inc., San Diego, CA (US)

(72) Inventors: Kevin L Gunderson, Encinitas, CA (US); Jeffrey G. Mandell, La Jolla, CA (US)

(73) Assignee: Illumina, Inc., San Diego, CA (US)

( * ) Notice: Subject to any disclaimer, the term of this patent is extended or adjusted under 35 U.S.C. 154(b) by 567 days.

This patent is subject to a terminal disclaimer.

(21) Appl. No.: 16/870,238

(22) Filed: May 8, 2020

(65) Prior Publication Data

US 2020/0318180 A1 Oct. 8, 2020

Related U.S. Application Data

(63) Continuation of application No. 15/577,728, filed as application No. PCT/US2016/035457 on Jun. 2, 2016, now Pat. No. 10,648,022.

(Continued)

(51) Int. Cl.
*C12Q 1/68* (2018.01)
*C12Q 1/6839* (2018.01)
(Continued)

(52) U.S. Cl.
CPC ......... *C12Q 1/6869* (2013.01); *C12Q 1/6839* (2013.01); *G01N 33/48721* (2013.01)

(58) Field of Classification Search
CPC ...................................................... C12Q 1/68
(Continued)

(56) References Cited

U.S. PATENT DOCUMENTS 6,015,714 A 1/2000 Baldarelli et al.
7,057,026 B2 6/2006 Barnes et al.
(Continued)

FOREIGN PATENT DOCUMENTS

CN 104212711 12/2014
WO 91/06678 5/1991
(Continued)

OTHER PUBLICATIONS

International Search Report, International Application No. PCT/US2016/035457, dated Aug. 12, 2016, 5 pages.
(Continued)

*Primary Examiner* — Aaron A Priest
(74) *Attorney, Agent, or Firm* — Gavrilovich, Dodd & Lindsey LLP

(57) ABSTRACT

A composition includes a nanopore including first and second sides and an aperture, nucleotides each including an elongated tag, and a first polynucleotide that is complementary to a second polynucleotide. A polymerase can be disposed adjacent to the first side of the nanopore and configured to add nucleotides to the first polynucleotide based on a sequence of the second polynucleotide. A permanent tether can include a head region anchored to the polymerase, a tail region, and an elongated body disposed therebetween that occurs in the aperture of the nanopore. A first moiety can be disposed on the elongated body that binds to the elongated tag of a first nucleotide upon which the polymerase is acting. A reporter region can be disposed on the elongated body that indicates when the first nucleotide is complementary or is not complementary to a next nucleotide in the sequence of the second polynucleotide.

21 Claims, 15 Drawing Sheets

Specification includes a Sequence Listing.

Related U.S. Application Data

(60) Provisional application No. 62/170,563, filed on Jun. 3, 2015.

(51) Int. Cl.
*C12Q 1/6869* (2018.01)
*G01N 33/487* (2006.01)

(58) Field of Classification Search
USPC .......................................................... 435/6.1
See application file for complete search history.

(56) References Cited

U.S. PATENT DOCUMENTS

| | | |
|---|---|---|
| 7,211,414 B2 | 5/2007 | Hardin et al. |
| 7,315,019 B2 | 1/2008 | Turner et al. |
| 7,329,492 B2 | 2/2008 | Hardin et al. |
| 7,405,281 B2 | 7/2008 | Xu et al. |
| 7,771,903 B2 | 8/2010 | Zhang et al. |
| 7,816,503 B2 | 10/2010 | Milton et al. |
| 8,133,672 B2 | 3/2012 | Bjornson et al. |
| 8,652,779 B2 | 2/2014 | Turner et al. |
| 8,673,550 B2 | 3/2014 | Gundlach et al. |
| 8,999,716 B2 | 4/2015 | Gundlach et al. |
| 9,017,937 B1 | 4/2015 | Turner |
| 9,027,947 B2 | 4/2015 | Turner et al. |
| 9,708,655 B2 | 7/2017 | Mandell |
| 2008/0108082 A1 | 5/2008 | Rank et al. |
| 2009/0298072 A1 | 12/2009 | Ju et al. |
| 2011/0174625 A1 | 7/2011 | Akeson |
| 2011/0312529 A1 | 12/2011 | He et al. |
| 2013/0146457 A1 | 6/2013 | Gundlach et al. |
| 2013/0240359 A1 | 9/2013 | Turner et al. |
| 2014/0051069 A1 | 2/2014 | Jayasinghe et al. |
| 2014/0087474 A1 | 3/2014 | Huber |
| 2014/0134616 A1 | 5/2014 | Davis et al. |

FOREIGN PATENT DOCUMENTS

| | | |
|---|---|---|
| WO | 2004/018497 A2 | 3/2004 |
| WO | 2007/123744 A2 | 11/2007 |
| WO | 2012/142174 A1 | 10/2012 |
| WO | 2012/164270 A1 | 12/2012 |
| WO | 2013/057495 A2 | 4/2013 |
| WO | 2013/0153359 | 10/2013 |
| WO | 2014/066902 A1 | 5/2014 |
| WO | 2015/126494 A1 | 8/2015 |
| WO | 2015/187670 A2 | 12/2015 |

OTHER PUBLICATIONS

Bentley et al., "Accurate whole human genome sequencing using reversible terminator chemistry," Nature 456:53-59 (2008).

Bonnac, et al., "Synthesis and O-phosphorylation of 3, 3,4,4-tetrafluoroaryl-C-nucleoside analogues", Org Biomol Chem 8(6), 2010, 1445-1454.

Butler, T.Z. et al., "Single-molecule DNA detection with an engineered MspA protein nanopore", Proceedings of the National Academy of Sciences USA, vol. 105, No. 52, Dec. 30, 2008, 20647-20652.

Cabello-Aguilar et al., "Slow translocation of polynucleotides and their discrimination by a-hemolysin inside a single track-etched nanopore desinged by atomic layer depostion", Nanoscale 5, 2013, 9582-9586.

Clarke et al., "Continuous base identification for single-molecule nanopore DNA sequencing", Nat. Biotech., vol. 4, published online, doi:10. 1038/nnano.2009.12, Feb. 22, 2009, 265-270.

Cockroft et al., "A single-molecule nanopore device detects DNA polymerase activity with single-nucleotide resolution", J. Am. Chem. Soc. 130(3), Jan. 23, 2008, 818-820.

Dahl et al., "Dynamics of translocation and substrate binding in individual complexes formed with active site mutants of {phi}29 DNA polymerase," J Biol Chem 289(10): 6350-6361 (2014).

Dekker, "Solid-state nanopores", Nature Nanotechnology 2, 2007, 209-215.

Derrington et al., "Nanopore DNA Sequencing with MspA", PNAS, vol. 107, No. 37, Sep. 14, 2010, 16060-16065.

Fierer et al., "SpyLigase peptide-peptide ligation polymerases aff-fibodies to enhance magentic cancer cell capture", Proc. Nat. Acad. Sci. USA, 111:E1176-1181 (2014), 2014, E1176-E1181.

Filmer, Richard, Office Action, Australian Patent Office, Application No. 2016270887, dated Jan. 9, 2019.

Freudenthal et al., "Observing a DNA polymerase choose right from wrong", Cell 154: 157-168, doi:10. 1016/j.cell.2013.05.048 (2013), 2013, 157-168.

Freudenthal et al., "Watching a DNA polymerase in action", Cell Cycle 13:691-692, doi:10.4161/cc.27789 (2014), 2014, 629-692.

Freudenthal et al., "New structural snapshots provide molecular insights into the mechanism of high fideltiy DNA synthesis", DNA Repair, doi:10.2016/j.dnarep/2015.04.007 (available online Apr. 30, 2015), Apr. 30, 2015.

Garaj et al., "Graphene as a sub-nanometer trans-electrode membrane", Nature 467, 2010, 190-193.

Garalde et al., "Distinct Complexes of DNA Polymerase I (Klenow Fragment) for Base and Sugar Discrimination during Nucleotide Substrate Selection", J. Biol. Chem. 286, 2011, 14480-14492.

Gill et al., "DNA polymerase activity at the single-molecule level", Biochem. Soc. Trans. 39, 2011, 595-599.

Hall et al., "Hybrid pore formation by directed insertion of alpha hemolysis into solid-state nanopores", Nature Nanotechnology 5, 2010, 874-877.

Howorka et al., "Kinetics of duplex formation for individual DNA strands within a single protein nanopore", PNAS 98, 2001, 12996-13301.

Howorka, et al., "Sequence-specific detection of individual DNA strands using engineered nanopores", Nature Biotechnology, vol. 19, Nature Publishing Group http://biotech.nature.com, exhibit cited in U.S. Patent Trial and Appeal Board Case No. IPR2014-00512 and Case No. IPR2014-00513, IPR2014-00513 #42, Jul. 2001, 636-639.

Hurt et al., "Specific Nucleotide Binding and Rebinding to Individual DNA Polymerase Complexes Captured on a Nanopore", JACS 131, 2009, 3772-3778.

Ivankin et al., "Label-Free Optical Detection of Biomolecular Translocation through Nanopore Arrays", ACSNano 8(10): (), 2014, 10774-10781.

Johnson, "The kinetic and chemical mechanism of high-fidelity DNA polymerases", Biochim Biophys Acta 1804(5), 2010, 1041-1048.

Johnson et al., "Processive DNA synthesis observed in a polymerase crystal suggests a mechanism for the prevention of frameshift mutations", Proc. Natl. Acad. Sci. USA 100, 2003, 3895-3900.

Kim et al., "Detecting single-abasic residues within a DNA strand immobilized in a biological nanopore using an integrated CMOS sensor", Sens. Actuators B Chem. 177, 2012, 1075-1082.

Kowalczyk et al., "Single-molecule transport across an individual biomimetic nuclear pore complex," Nature Nanotechnology, 6(7): 433-438 (2011). cited by applicant. Invitation to Pay Additional Fees in PCT/US2015/033749, dated Oct. 29, 2015 (8 pages).

Kulkarni, G.S. and Z. Zhong, "Detection beyond the Debye screening length in a high-frequency nanoelectronic biosensor," Nano Lett 12(2): 719-723 (2012).

Kulkarni, G.S. and Z. Zhong, "Fabrication of carbon nanotube high-frequency nanoelectronic biosensor for sensing in high ionic strength solutions," J Vis Exp(77) (2013).

Kumar et al., "Terminal Phosphate Labeled Nucleotides: Synthesis, Applications, and Linker Effect on Incorporation by DNA Polymerases", Nucleosides, Nucleotides, and Nucleic Acids 24, 2005, 401-408.

Kumar, et al., "PEG-Labeled Nucleotides and Nanopore Detection for Single Molecule DNA Sequencing by Synthesis", Scientific Reports 2, 2012, 684.

Lee et al., "Synthesis and reactivity of novel y-phosphate modified ATP analogues", Bioorganic & Medicinal Chemistry Letters 19, 2009, 3804-3807.

(56) References Cited

OTHER PUBLICATIONS

Lieberman et al., "Kinetic mechanism of translocation and dNTP binding in individual DNA polymerase complexes," J Am Chem Soc 135(24): 9149-9155 (2013).
Manrao et al., "Nucleotide discrimination with DNA immobilized in the MspA nanopore," PLos ONE 6: e25723, 7 pages, (2011).
Markiewicz et al., "Single-molecule microscopy reveals new insights into nucleotide selection by DNA polymerase I", Nucleic Acids Res. 40, 2012, 7975-7984.
Merchant et al., "DNA Translocation through Graphene Nanopores", Nano Letters 10, 2010, 2915-2921.
Mulder et al., "Nucleotide modification at the y-phosphate leads to the improved fidelity of HIV-1 reverse transcriptase", Nucleic Acids Res. 33, No. 15, 2005, 4865-4873.
Olsen et al., "Electronic Measurements of Single-Molecule Processing by DNA Polymerase I (Klenow Fragment)", J Am Chem Soc 135(21), May 2013, pp. 7855-7860.
Osmanovic et al., "Bistable collective behavior of polymers tethered in a nanopore," arxiv.org, Cornell University library, 2012 Olin Library Cornell University Ithaca, NY 14853, XP080525258 (Jul. 17, 2012).
Patel, "Getting a grip on how DNA polymerases function", Nature Structural Biology 8, 2001, 656-659.
Santoso, Yusdi, "Conformational Transitions in DNA Polymerase I Revealed by Single-Molecule FRET", Proceedings of the National Academy of Sciences; vol. 107, No. 2, Jan. 12, 2010, 715-720.
Schneider et al., "DNA Translation through Graphene Nanopores", Nano Letters 10, 2010, 3163-3167.
Sood et al., "Terminal Phosphate-Labeled Nucleotides with Improved Substrate Properties forHomogeneous Nucleic Acid Assays", J Am Chem Soc 127(8), 2005, 2394-2395.
Torella et al., "Identifying Molecular Dynamics in Single-Molecule FRET Experiments with Burst Variance Analysis", Biophysics J. 1OOf, 2011, 1568-1577.
Venkatesan, et al., "Nanopore sensors for nucleic acid analysis", Nature Nanotechnology, vol. 6, No. 10, Sep. 18, 2011, 615-624.
Wang, et al., "Single-molecule DNA detection using a novel SP1 protein nanopore", Chem. Commun., 49, 2013, 1741-1743.
Wilson, Noah A. et al., "Electronic Control of DNA Polymerase Binding and Unbinding to Single DNA Molecules", ACS Nano, vol. 3, No. 4, Apr. 28, 2009, pp. 996-997, Apr. 28, 2009, 996-997.
Xia et al., "Alteration in the cavity size adjacent to the active site of RB69 DNA polymerase changes its conformational dynamics" Nucl. Acids Res., vol. 41, No. 19, pp. 9077-9089, 2013.
Zakeri, et al., "Peptide tag forming a rapid covalent bond to a protein, through engineering a bacterial adhesin", Proc. Nat. Acad. Sci. USA 109:E690-3697 (2012), 2012, E690-E697.
Chavanne, Franz, International Search Report for PCT/US2015/033749, dated Jan. 29, 2016 (9 pages).
Chavanne, Franz, Written Opinion of the International Searching Authority for PCT/US2015/033749 dated Jan. 29, 2016 (11 pages).
Du, Ning, Intellectual Property Office of Singapore, Office Action, Application No. 11201609692S dated Jan. 4, 2018, 4 pages.
Franceschini, L et al., "A nanopore machine promotes the vectorial transport of DNA across membranes", Nature Communications, vol. 4, p. 2415, Sep. 12, 2013.
Howorka et al., "Probing distance and electrical potential within a protein pore with tethered DNA", Biophysical Journal, 83:3202-3210 (2002).

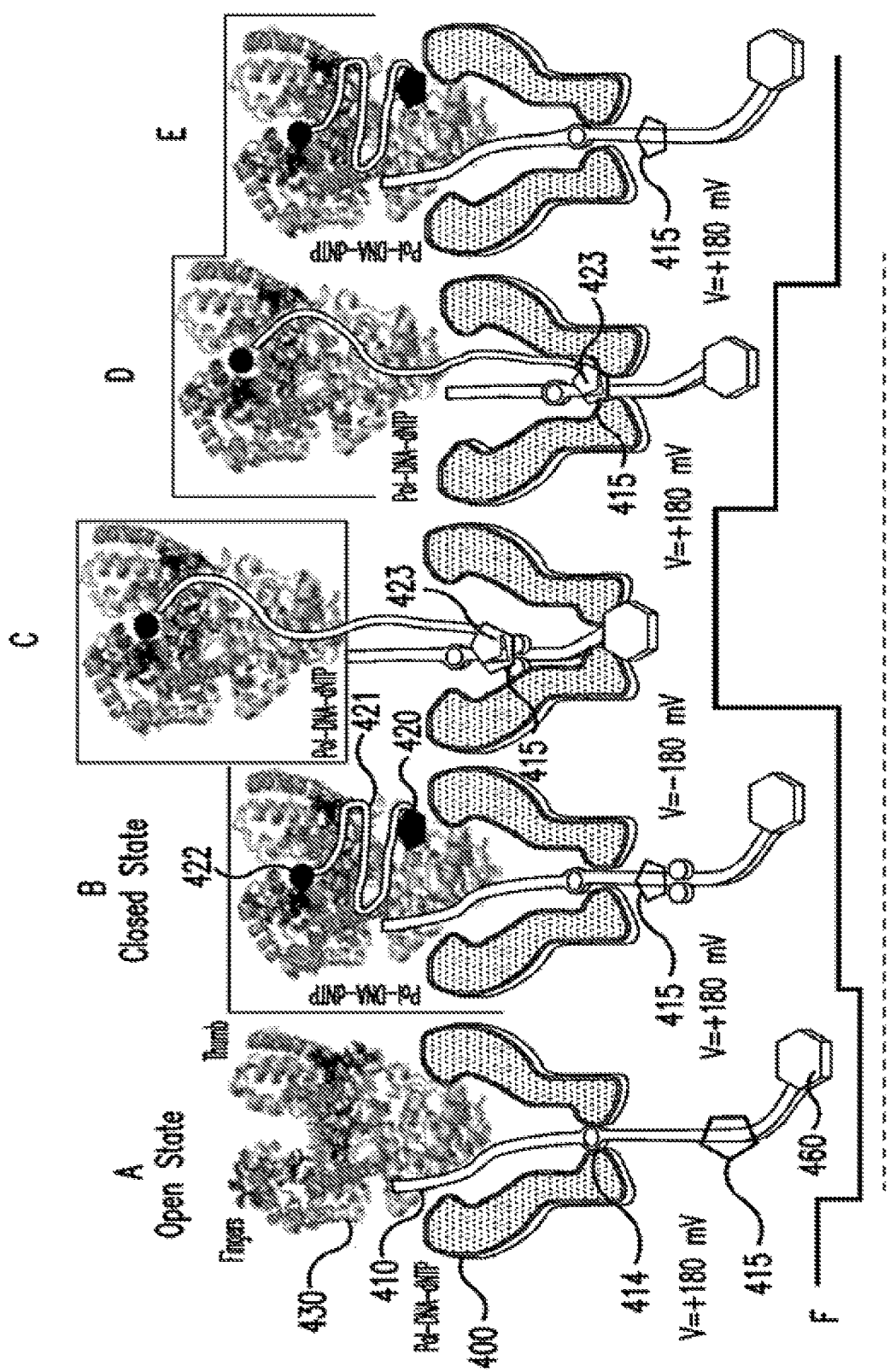
FIG. 4 A-F

| | Reaction Parameters | Tag Dwell Time (usec) |
|---|---|---|
| Reaction Scheme | $ED_n + dNTP \underset{K_{-1}}{\overset{K_1}{\rightleftharpoons}} ED_n dNTP \underset{K_{-2}}{\overset{K_2}{\rightleftharpoons}} FD_n dNTP \underset{K_{-3}}{\overset{K_3}{\rightleftharpoons}} FD_{n+1} PP_i \overset{fast}{\longrightarrow} ED_{n+1} PP_i$ <br> open, open, closed, closed, open | $1/(k_2 + k_3)$ |
| Perfect Match Nucleotide | $ED_n + dNTP \underset{\text{open}}{\overset{23\mu M}{\rightleftharpoons}} ED_n dNTP \underset{1.6 s^{-1}}{\overset{660 s^{-1}}{\rightleftharpoons}} FD_n dNTP \underset{\text{closed}}{\overset{360 s^{-1}}{\rightleftharpoons}} FD_{n+1} PP_i \overset{fast}{\longrightarrow} ED_{n+1} PP_i$ | 2760 |
| Mismatch Nucleotide | $ED_n + dNTP \underset{\text{open}}{\overset{200\mu M}{\rightleftharpoons}} ED_n dNTP \underset{420 s^{-1}}{\overset{220 s^{-1}}{\rightleftharpoons}} GD_n dNTP \underset{\text{mismatch}}{\overset{0.3 s^{-1}}{\rightleftharpoons}} GD_{n+1} PP_i \overset{fast}{\longrightarrow} ED_{n+1} PP_i$ | 2380 |

FIG. 8

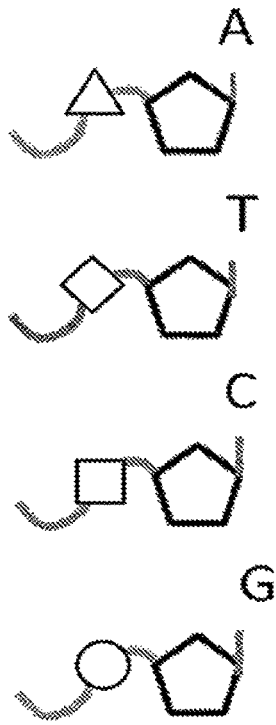
FIG. 9B
△ = 5'-CCCAT-3'      (A)
◇ = 5'-CCCATA-3'     (T)
☐ = 5'-CCCATAT-3'    (C)
◯ = 5'-CCCATATA-3'   (G)
FIG. 9C
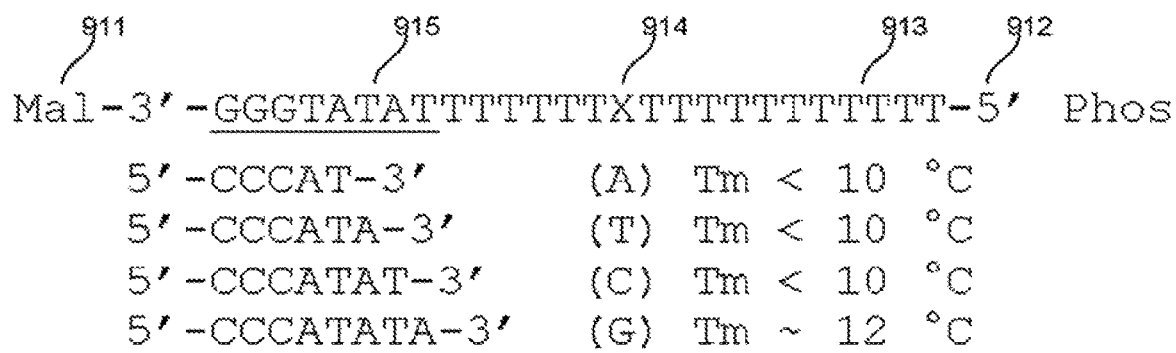
FIG. 9D

COMPOSITIONS, SYSTEMS, AND METHODS FOR SEQUENCING POLYNUCLEOTIDES USING TETHERS ANCHORED TO POLYMERASES ADJACENT TO NANOPORES

CROSS-REFERENCE TO RELATED APPLICATIONS

This application is a continuation of U.S. patent application Ser. No. 15/577,728, filed Nov. 28, 2017, which application claims priority under 35 U.S.C. § 371 of International Application No. PCT/US2016/035457, filed Jun. 2, 2016, which application claims the benefit of U.S. Provisional Patent Application Ser. No. 62/170,563, filed Jun. 3, 2015, the disclosure of all of the foregoing are incorporated herein by reference in their entireties.

This application is related to the following applications, the entire contents of each of which are incorporated by reference herein: U.S. Provisional Patent Application No. 62/007,248, filed Jun. 3, 2014 and entitled "Compositions, Systems, and Methods for Detecting Events Using Tethers Anchored to or Adjacent to Nanopores;" U.S. Provisional Patent Application No. 62/157,371, filed May 5, 2015 and entitled "Compositions, Systems, and Methods for Detecting Events Using Tethers Anchored to or Adjacent to Nanopores;" and U.S. patent application Ser. No. 14/728,721, filed Jun. 2, 2015 and entitled "Compositions, Systems, and Methods for Detecting Events Using Tethers Anchored to or Adjacent to Nanopores."

SEQUENCE LISTING

The instant application contains a Sequence Listing which has been submitted electronically in ASCII format and is hereby incorporated by reference in its entirety. Said ASCII copy, created on May 8, 2020, is named 12957-180-28_SL.txt and is 796 bytes in size.

FIELD

This application generally relates to sequencing polynucleotides.

BACKGROUND

A significant amount of academic and corporate time and energy has been invested into sequencing polynucleotides, such as DNA. For example, Olsen et al., "Electronic Measurements of Single-Molecule Processing by DNA Polymerase I (Klenow Fragment)," JACS 135: 7855-7860 (2013), the entire contents of which are incorporated by reference herein, discloses bioconjugating single molecules of the Klenow fragment (KF) of DNA polymerase I into electronic nanocircuits so as to allow electrical recordings of enzymatic function and dynamic variability with the resolution of individual nucleotide incorporation events. Or, for example, Hurt et al., "Specific Nucleotide Binding and Rebinding to Individual DNA Polymerase Complexes Captured on a Nanopore," JACS 131: 3772-3778 (2009), the entire contents of which are incorporated by reference herein, discloses measuring the dwell time for complexes of DNA with the KF atop a nanopore in an applied electric field. Or, for example, Kim et al., "Detecting single-abasic residues within a DNA strand immobilized in a biological nanopore using an integrated CMOS sensor," Sens. Actuators B Chem. 177: 1075-1082 (2012), the entire contents of which are incorporated by reference herein, discloses using a current or flux-measuring sensor in experiments involving DNA captured in a α-hemolysin nanopore. Or, for example, Garalde et al., "Distinct Complexes of DNA Polymerase I (Klenow Fragment) for Based and Sugar Discrimination during Nucleotide Substrate Selection," J. Biol. Chem. 286: 14480-14492 (2011), the entire contents of which are incorporated by reference herein, discloses distinguishing KF-DNA complexes on the basis of their properties when captured in an electric field atop an α-hemolysin pore. Other references that disclose measurements involving α-hemolysin include the following, all to Howorka et al., the entire contents of which are incorporated by reference herein: "Kinetics of duplex formation for individual DNA strands within a single protein nanopore," PNAS 98: 12996-13301 (2001); "Probing Distance and Electrical Potential within a Protein Pore with Tethered DNA," Biophysical Journal 83: 3202-3210 (2002); and "Sequence-specific detection of individual DNA strands using engineered nanopores," Nature Biotechnology 19: 636-639 (2001).

U.S. Pat. No. 8,652,779 to Turner et al., the entire contents of which are incorporated by reference herein, discloses compositions and methods of nucleic acid sequencing using a single polymerase enzyme complex including a polymerase enzyme and a template nucleic acid attached proximal to a nanopore, and nucleotide analogs in solution. The nucleotide analogs include charge blockade labels that are attached to the polyphosphate portion of the nucleotide analog such that the charge blockade labels are cleaved when the nucleotide analog is incorporated into a growing nucleic acid. According to Turner, the charge blockade label is detected by the nanopore to determine the presence and identity of the incorporated nucleotide and thereby determine the sequence of a template nucleic acid. U.S. Patent Publication No. 2014/0051069 to Jayasinghe et al., the entire contents of which are incorporated by reference herein, is directed to constructs that include a transmembrane protein pore subunit and a nucleic acid handling enzyme.

However, previously known compositions, systems, and methods such as described by Olsen, Hurt, Kim, Garalde, Howorka, Turner, and Jayasinghe may not necessarily be sufficiently robust, reproducible, or sensitive and may not have sufficiently high throughput for practical implementation, e.g., demanding commercial applications such as genome sequencing in clinical and other settings that demand cost effective and highly accurate operation. Accordingly, what is needed are improved compositions, systems, and methods for sequencing polynucleotides.

SUMMARY

Embodiments of the present invention provide compositions, systems, and methods for sequencing polynucleotides using tethers anchored to polymerases adjacent to nanopores.

Under one aspect, a composition includes a nanopore including a first side, a second side, and an aperture extending through the first and second sides. The composition also can include a plurality of nucleotides, wherein each of the nucleotides includes an elongated tag. The composition also can include first and second polynucleotides, the first polynucleotide being complementary to the second polynucleotide. The composition also can include a polymerase disposed adjacent to the first side of the nanopore, the polymerase configured to add nucleotides of the plurality of nucleotides to the first polynucleotide based on a sequence of the second polynucleotide. The composition also can include a permanent tether including a head region, a tail region, and an elongated body disposed there between, the head region being anchored to the polymerase, wherein the elongated body occurs in the aperture of the nanopore. The composition also can include a first moiety disposed on the elongated body, wherein the first moiety is configured to bind to the elongated tag of a first nucleotide upon which the polymerase is acting, as well as a reporter region disposed on the elongated body, wherein the reporter region is configured to indicate when the first nucleotide is complementary or is not complementary to a next nucleotide in the sequence of the second polynucleotide.

In some embodiments, the first moiety is configured to generate a first signal state responsive to the polymerase acting upon the first nucleotide, the first nucleotide being identifiable based on the first signal state. In some embodiments, the polymerase acting upon the first nucleotide includes the polymerase binding the first nucleotide. In some embodiments, the first signal state includes an electrical or optical signal.

In some embodiments, the reporter region is configured to generate a second signal state, it being detectable based upon the second signal state whether the first nucleotide is complementary or is not complementary to the next nucleotide of the second polynucleotide. In some embodiments, the reporter region is configured to generate the second signal state responsive to the polymerase successfully incorporating the first nucleotide into the first polynucleotide.

In some embodiments, the reporter region is configured to generate the second signal state responsive to release of pyrophosphate responsive to the polymerase successfully incorporating the first nucleotide into the first polynucleotide. In some embodiments, the polymerase is modified so as to delay release of the pyrophosphate responsive to incorporation of the first nucleotide into the first polynucleotide. In some embodiments, the polymerase includes a modified recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase. In some embodiments, the polymerase includes a modified recombinant Φ29 DNA polymerase having at least one amino acid substitution or combination of substitutions selected from the group consisting of: an amino acid substitution at position 484, an amino acid substitution at position 198, and an amino acid substitution at position 381. In some embodiments, the polymerase includes a modified recombinant Φ29 DNA polymerase having at least one amino acid substitution or combination of substitutions selected from the group consisting of E375Y, K512Y, T368F, A484E, A484Y, N387L, T372Q, T372L, K478Y, 1370 W, F198 W, and L381A.

In some embodiments, the reporter region is configured to generate the second signal state responsive to a conformational change of the polymerase. In some embodiments, a magnitude or a time duration of the conformational change of the polymerase being responsive to the first nucleotide being complementary or not complementary to the next nucleotide of the second polynucleotide, a magnitude or a time duration, or both, of the second signal state being based upon the conformational change of the polymerase.

In some embodiments, the second signal state includes an electrical signal. In some embodiments, the second signal state includes an optical signal.

In some embodiments, the elongated tag includes a first nucleotide sequence and the first moiety includes a second nucleotide sequence that is complementary to the first nucleotide sequence. A system can include such a composition, and further can include measurement circuitry configured to measure a first current or flux state through the aperture. In some embodiments, the first current or flux state is based on the elongated tag, the first nucleotide being identifiable based on the first current or flux state. In some embodiments, the measurement circuitry further is configured to measure a second current or flux state through the aperture. In some embodiments, the second current or flux state is based on a position of the reporter region within the aperture, it being determinable based on the second current or flux state whether the first nucleotide is complementary or is not complementary to the next nucleotide in the second polynucleotide.

In some embodiments, the first moiety and a second moiety of the tether are configured to hybridize with one another so as to form a hairpin structure. In some embodiments, the composition further includes a voltage source configured to apply a voltage across the first and second sides. In some embodiments, the first moiety and the second moiety of the tether are configured to dehybridize from one another responsive to the voltage in a two-step process.

Under another aspect, a method can include providing a nanopore including a first side, a second side, and an aperture extending through the first and second sides. The method further can include providing a plurality of nucleotides, wherein each of the nucleotides includes an elongated tag. The method further can include providing first and second polynucleotides, the first polynucleotide being complementary to the second polynucleotide. The method further can include providing a polymerase disposed adjacent to the first side of the nanopore, the polymerase configured to add nucleotides of the plurality of nucleotides to the first polynucleotide based on a sequence of the second polynucleotide, wherein the polymerase is anchored to a permanent tether including a head region, a tail region, and an elongated body disposed there between, the elongated body occurring in the aperture of the nanopore. The method further can include determining that a first nucleotide is being acted upon by the polymerase based on binding of the elongated tag to a first moiety disposed on the elongated body. The method further can include, with a reporter region disposed on the elongated body, indicating when the first nucleotide is complementary or is not complementary to a next nucleotide in the sequence of the second polynucleotide.

In some embodiments, said determining includes generating a first signal state responsive to the polymerase acting upon the first nucleotide and identifying the first nucleotide based on the first signal state. In some embodiments, the polymerase acting upon the first nucleotide includes the polymerase binding the first nucleotide. In some embodiments, the first signal state includes an electrical or optical signal.

In some embodiments, said indicating includes detecting a second signal state and determining based upon the second signal state that the first nucleotide is complementary or is not complementary to the next nucleotide of the second polynucleotide. In some embodiments, the method includes generating the second signal state responsive to the polymerase incorporating the first nucleotide into the first polynucleotide.

In some embodiments, the method includes generating the second signal state responsive to release of pyrophosphate responsive to the polymerase incorporating the first nucleotide into the first polynucleotide. In some embodiments, the polymerase is modified so as to delay release of the pyrophosphate responsive to incorporation of the first nucleotide into the first polynucleotide. In some embodiments, the polymerase includes a modified recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase. In some embodiments, the polymerase includes a modified recombinant Φ29 DNA polymerase having at least one amino acid substitution or combination of substitutions selected from the group consisting of: an amino acid substitution at position 484, an amino acid substitution at position 198, and an amino acid substitution at position 381. In some embodiments, the polymerase includes a modified recombinant Φ29 DNA polymerase having at least one amino acid substitution or combination of substitutions selected from the group consisting of E375Y, K512Y, T368F, A484E, A484Y, N387L, T372Q, T372L, K478Y, 1370 W, F198 W, and L381A.

In some embodiments, the method includes generating the second signal state responsive to a conformational change of the polymerase. In some embodiments, a magnitude or a time duration of the conformational change of the polymerase is responsive to the first nucleotide being complementary or not complementary to the next nucleotide of the polynucleotide, a magnitude or a time duration, or both, of the second signal state being based upon the conformational change of the polymerase.

In some embodiments, the second signal state includes an electrical signal. In some embodiments, the second signal state includes an optical signal.

In some embodiments, the elongated tag includes a first nucleotide sequence and the first moiety includes a second nucleotide sequence that is complementary to the first nucleotide sequence. In some embodiments, said determining further includes measuring a first current or flux state through the aperture. In some embodiments, the first current or flux state is based on the elongated tag, said determining further including identifying the first nucleotide based on the first current or flux state. In some embodiments, said indicating includes moving the reporter region within the aperture responsive to the polymerase acting upon the first nucleotide. In some embodiments, said indicating further includes measuring a second current or flux state through the aperture. In some embodiments, the second current or flux state is based on a position of the reporter region within the aperture, said indicating further including determining based on the second current or flux state whether the first nucleotide is complementary or is not complementary to the next nucleotide in the second polynucleotide.

In some embodiments, the first moiety and a second moiety of the tether hybridize with one another so as to form a hairpin structure. Some embodiments further include applying a voltage across the first and second sides. In some embodiments, the first moiety and the second moiety of the tether dehybridize from one another responsive to the voltage in a two-step process.

In some embodiment, the method includes determining that a subsequent nucleotide is being acted upon by the polymerase based on binding of the elongated tag to the first moiety disposed on the elongated body; and with a reporter region disposed on the elongated body, indicating when the subsequent nucleotide is complementary or is not complementary to a nucleotide that is subsequent to the next nucleotide in the sequence of the second polynucleotide. Some embodiments include repeating such steps for a plurality of subsequent nucleotides that are complementary or not complementary to a plurality of nucleotides that are subsequent to the next nucleotide.

BRIEF DESCRIPTION OF DRAWINGS

FIGS. 4A-4E schematically illustrate an exemplary use of a composition for sequencing a polynucleotide using a tether anchored to a polymerase adjacent to a nanopore, according to some embodiments of the present invention.

FIG. 4F schematically illustrates an exemplary signal that can be generated during use of the composition of FIGS. 4A-4E, according to some embodiments of the present invention.

FIG. 8 illustrates exemplary reaction parameters, e.g., rate constants and dwell times, for reaction schemes in which a nucleotide respectively being acted upon by a polymerase is a match or mismatch (adapted from Johnson, "The kinetic and chemical mechanism of high-fidelity DNA polymerases," Biochim Biophys Acta 1804(5): 1041-1048 (2010), the entire contents of which are incorporated by reference herein).

FIGS. 9B-9C schematically illustrate exemplary nucleotides including elongated tags including respective moieties that can interact with an exemplary tether during use in sequencing a polynucleotide, according to some embodiments of the present invention.

FIG. 9D schematically illustrates an exemplary tether and moieties that can interact with the tether during use in sequencing a polynucleotide, according to some embodiments of the present invention. Figure discloses SEQ ID NO: 1.

DETAILED DESCRIPTION

Figure 1A:
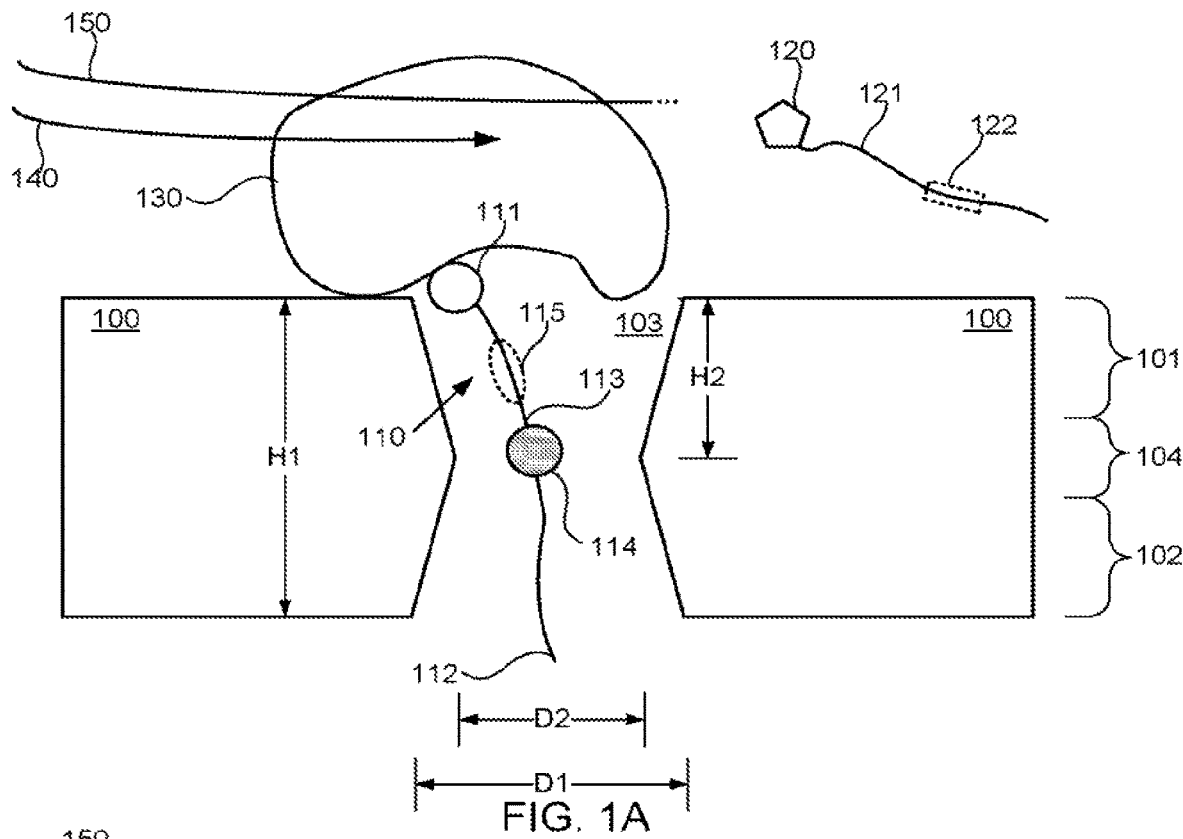
FIGS. 1A-1D schematically illustrate compositions for sequencing polynucleotides using a tether anchored to a polymerase adjacent to a nanopore, according to some embodiments of the present invention.

Embodiments of the present invention provide compositions, systems, and methods for sequencing polynucleotides using tethers anchored to polymerases adjacent to nanopores.

More specifically, the present compositions, systems, and methods suitably can be used to sequence polynucleotides in a manner that is robust, reproducible, sensitive, and has high throughput. For example, the present compositions can include a nanopore and a permanent tether that is anchored to a polymerase that is disposed adjacent to the nanopore. The nanopore can include first and second sides and an aperture that extends through the first and second sides. The permanent tether can include head and tail regions and an elongated body disposed there between. In particular embodiments, the head region of the tether is anchored to the polymerase, which is disposed adjacent to the first side of the nanopore, and the elongated body occurs in the aperture of the nanopore. Additionally, the present compositions can include a plurality of nucleotides, each of which includes an elongated tag. The tether or the elongated tag, or both, can include one or more features that facilitates sequencing a polynucleotide, e.g., a template polynucleotide. For example, the tether or the elongated tag, or both, can include one or more features that provide a first signal state based upon the polymerase acting upon a nucleotide, and can include one or more features that provide a second signal state based upon that nucleotide being complementary or not complementary to a next nucleotide in a sequence of the polynucleotide being sequenced. In some embodiments, the identity of the nucleotide being acted upon by the polymerase can be determined based on the first signal state. Additionally, in some embodiments, the complementarity of that nucleotide to a next nucleotide in a sequence of the polynucleotide being sequenced can be determined based on the second signal state, which can help to distinguish whether that nucleotide is complementary to the polynucleotide being sequenced, or if instead the polymerase temporarily acted upon a nucleotide that was not complementary to the next nucleotide in the sequence of the polynucleotide being sequenced, but without adding that nucleotide to the growing, complementary polynucleotide. Thus, the second signal state can be useful in basecalling during a nucleic acid sequencing application, for example, by providing an error checking function. It should be understood that such first and second signal states, which respectively can represent identities of nucleotides or whether such nucleotides are a match or a mismatch, need not necessarily occur at different times than one another, and indeed can occur at the same time as one other. For example, a measured signal (e.g., optical or electrical) can include a composite of more than one signal state (e.g., two signal states), each of which signal states provides information about one or more of an identity of a nucleotides or whether such nucleotide is a match or a mismatch.

Previously known methods for sequencing by synthesis (SBS) have been developed. For example, single stranded DNA (ssDNA) can pass through a biological nanopore, such as a protein nanopore, that is embedded in a barrier such as a lipid bilayer, responsive to an electrical potential being applied across the nanopore. In what can be referred to as "strand" sequencing, as nucleotides of the ssDNA pass through a pore constriction, combinations of those nucleotides can create unique current or flux blockades corresponding to the identities of nucleotides in the particular combinations pass through the constriction. These strands that are being sequenced are not permanently attached to the pore or polymerase. Rather, these strands translocate through the pore such that the net position of the strand changes relative to the pore. However, the extremely rapid translocation rate of ssDNA (~1 nt/μsec), as well as the native resolution of the constriction that encompasses a combination of nucleotides, rather than a single nucleotide, can hinder accurate measurement of such current or flux blockades on a nucleotide-by-nucleotide basis. Enzymatic "motors" have been used to slow the translocation speed to a rate which is more compatible with data acquisition (milliseconds per nucleotide). However, such motors when used in strand sequencing configurations can introduce error modes such as skipping, slipping and toggling, which can inhibit reliable detection of nucleotides in the ssDNA. These and other motor-independent error modes that can occur during strand sequencing can result from the "springiness" or elasticity of the ssDNA residing between the motor and the constriction of the nanopore. Such springiness can be a function of the sequence of the ssDNA, and can result in different currents or fluxes for the same combination of nucleotides transiting the constriction if different instances of that combination respectively are surrounded by different ssDNA sequences. Further, because the constriction can be relatively small, e.g., about 2 nt, and Brownian motion is always present, the pore "read head" can be effectively about 4 nucleotides in size, e.g., the constriction reads a combination of about 4 nucleotides at a time, thus making it more difficult to uniquely identify each nucleotide since there are 4^4 (256) currents or fluxes that need to be differentiated from one another.

Accordingly, a need remains for improvements in SBS, e.g., for inexpensive, accurate, long-read, high-throughput compositions, systems, and methods for SBS. SBS using nanopores, e.g., biological nanopores, represents one potential solution to this need because of the nanoscale reproducibility and ease of production of these proteins. Taken together, an approach which is motor free (e.g., using nucleic enzymes as a detector that is coupled to a nanopore rather than as a motor that modulates passage of a target strand through a nanopore), more tolerant of Brownian motion, and has single nucleotide resolution can be expected to greatly advance the field of nanopore DNA sequencing.

First, some terms used herein will be briefly explained. Then, some exemplary compositions, exemplary systems including measurement circuitry (e.g., electrical or optical measurement circuitry) that can be used with the present compositions, exemplary methods that can be used with the present compositions, and some specific examples of compositions that can be used during such methods, will be described.

Exemplary Terms

As used herein, the term "pore" is intended to mean a structure that includes an aperture that permits molecules to cross there through from a first side of the pore to a second side of the pore. That is, the aperture extends through the first and second sides of the pore. Molecules that can cross through an aperture of a pore can include, for example, ions or water-soluble molecules such as nucleic acids, proteins, nucleotides, and amino acids. The pore can be disposed within a barrier. When at least a portion of the aperture of a pore has a width of 100 nm or less, e.g., 10 nm or less, or 2 nm or less, the pore can be, but need not necessarily be, referred to as a "nanopore." Optionally, a portion of the aperture can be narrower than one or both of the first and second sides of the pore, in which case that portion of the aperture can be referred to as a "constriction." Alternatively or additionally, the aperture of a pore, or the constriction of a pore (if present), or both, can be greater than 0.1 nm, 0.5 nm, 1 nm, 10 nm or more. A pore can include multiple constrictions, e.g., at least two, or three, or four, or five, or more than five constrictions.

As used herein, a "barrier" is intended to mean a structure that normally inhibits passage of molecules from one side of the barrier to the other side of the barrier. The molecules for which passage is inhibited can include, for example, ions or water soluble molecules such as nucleic acids, proteins, nucleotides, and amino acids. A pore can be disposed within a barrier, and the aperture of the pore can permit passage of molecules from one side of the barrier to the other side of the barrier. Barriers include membranes of biological origin, and non-biological barriers such as solid state membranes.

As used herein, "tether" is intended to mean an elongated member having a head region, a tail region, and an elongated body there between. A tether include a molecule. A tether can be, but need not necessarily be, in an elongated state, e.g., can include an elongated molecule. For example, an elongated body of a tether can have secondary or tertiary configurations such as hairpins, folds, helical configurations, or the like. Tethers can include polymers such as polynucleotides or synthetic polymers. Tethers can have lengths (e.g., measured in a stretched or maximally extended state) ranging, for example, from about 5 nm to about 500 nm, e.g., from about 10 nm to about 100 nm. Tethers can have widths ranging, for example, from about 1 nm to about 50 nm, e.g., from about 2 nm to about 20 nm. Tethers can be linear or branched. A tether can be considered to be "permanent" when it is not removed from a composition set forth herein under the conditions in which the composition is used, for example, in a detection method. A tether that is used in a cyclic or repeated reaction can also be considered "permanent" when there is no net change in position of the tether from one cycle to the next or from one reaction to a repeat of the reaction. It will be understood that the position of a permanent tether may change during an individual cycle or reaction even though there is no net change in position across the cycles or reactions.

As used herein, a "head region" of a tether is intended to mean a functional group of the tether that is attached to another member. Such attachment can be formed via a chemical bond, e.g., via a covalent bond, hydrogen bond, ionic bond, dipole-dipole bond, London dispersion forces, or any suitable combination thereof. In one embodiment, such attachment can be formed through hybridization of a first oligonucleotide of the head region to a second oligonucleotide of another member. Alternatively, such attachment can be formed using physical or biological interactions, e.g., an interaction between a first protein structure of the head region and a second protein structure of the other member that inhibits detachment of the head region from the other member. Exemplary members to which a head region of a tether can be attached include a pore, e.g., the first or second side of the pore, a barrier in which the pore is disposed, and a molecule, such as a protein, disposed on either the first or second side of the pore. If the head region of the tether is attached to another member that is disposed on either the first or second side of the pore, the head region of the tether can be said to be adjacent to the pore. The head region can be, but need not necessarily be, located at an end of the tether.

As used herein, "anchored" is intended to mean an attachment between a first member and a second member that is permanent, e.g., is sufficiently stable as to be useful for sequencing a polynucleotide, or, e.g., is movable but undergoes no net movement under the conditions in which the attached members are used. In some embodiments, such a permanent attachment is normally irreversible under the conditions in which the attached members are used, for example, in a detection method. In other embodiments, such a permanent attachment is reversible but persists for at least the period of time in which it is used for sequencing a polynucleotide. For example, a tether can be permanently attached to or adjacent to a polymerase during use of the tether to sequence a polynucleotide, and can be subsequently removable or replaceable with another tether. Covalent bonds are only one example of an attachment that suitably can be used to anchor a first member to a second member. Other examples include duplexes between oligonucleotides, peptide-peptide interactions, and streptavidin-biotin or streptavidin-desthiobiotin.

As used herein, a "tail region" of a tether is intended to mean a portion of the tether that is disposed distally from the head region. The tail region can extend freely away from the head region, e.g., can be unattached to any other member. The tail region alternatively can be attached. Such attachment can be formed via a chemical bond, e.g., via a covalent bond, hydrogen bond, ionic bond, dipole-dipole bond, London dispersion forces, or any suitable combination thereof. In one embodiment, such attachment can be formed through hybridization of a first oligonucleotide of the tail region to a second nucleotide of another member. Alternatively, such attachment can be formed using physical or biological interactions e.g., an interaction between a first protein structure of the tail region and a second protein structure of the other member that inhibits detachment of the tail region from the other member. Any member to which the tail region is attached can be, but need not necessarily be, the same member to which the head region is attached. The tail region can be, but need not necessarily be, located at an end of the tether.

As used herein, an "elongated body" is intended to mean a portion of a member, such as a tether, that is sufficiently long and narrow to be disposed within at least a portion of an aperture of a pore. When an elongated body is attached to a nucleotide being acted upon, such an elongated body can be referred to as an "elongated tag" so as to facilitate distinction from an elongated body of a tether. An elongated body can be formed of any suitable material of biological origin or non-biological origin, or a combination thereof. In one example, the elongated body includes a polymer. Polymers can be biological or synthetic polymers. Exemplary biological polymers that suitably can be included within an elongated body include polynucleotides, polypeptides, polysaccharides, polynucleotide analogs, and polypeptide analogs. Exemplary polynucleotides and polynucleotide analogs suitable for use in an elongated body include DNA, enantiomeric DNA, RNA, PNA (peptide-nucleic acid), morpholinos, and LNA (locked nucleic acid). Exemplary synthetic polypeptides can include charged amino acids as well as hydrophilic and neutral residues. Exemplary synthetic polymers that suitably can be included within an elongated body include PEG (polyethylene glycol), PPG (polypropylene glycol), PVA (polyvinyl alcohol), PE (polyethylene), LDPE (low density polyethylene), HDPE (high density polyethylene), polypropylene, PVC (polyvinyl chloride), PS (polystyrene), NYLON (aliphatic polyamides), TEFLON® (tetrafluoroethylene), thermoplastic polyurethanes, polyaldehydes, polyolefins, poly(ethylene oxides), poly($\omega$-alkenoic acid esters), poly(alkyl methacrylates), and other polymeric chemical and biological linkers such as described in Hermanson, *Bioconjugate Techniques*, third edition, Academic Press, London (2013). Additionally, an elongated body optionally can include a moiety that can interact with another moiety. Such moieties can include biological polymers DNA, RNA, PNA, LNA, morpholinos, or enantiomeric DNA, for example. Regions of the elongated body can be charged or neutral depending on the particular implementation of the reporter readout.

As used herein, a "reporter region" is intended to mean a moiety that is, upon a change, detectable using a suitable detection method or system. Such change can include, but is not limited to, movement. Movements can be approximately 10 nm or less, or approximately 5 nm or less, or approximately 2 nm or less, or approximately 1 nm or less, or approximately 0.5 nm or less, or approximately 0.2 nm or less, or even approximately 0.1 nm or less, and can be detected using the reporter region and a suitable detection method or system. The moiety can have a detectable physical, chemical, electrical, optical, or biological property or other suitable flux blockade property. For example, the moiety can have an optical property that facilitates optical detection or characterization. Optical properties include fluorescence and generation of a Raman signal. In one illustrative example, the moiety is a fluorescent resonance energy transfer (FRET) donor or acceptor that interacts with a corresponding FRET acceptor or donor so as to emit light of a particular wavelength that can be detected. The donor and acceptor can be considered to be FRET pair partners. Or, for example, the moiety can have an electrical or flux blockade property. Electrical or flux blockade properties include electrostatic charge, e.g., a positive charge, or a negative charge. Or, for example, the moiety can have a physical property. Physical properties include the volume and shape of the moiety. In one illustrative example, movement of the moiety within the aperture causes a measurable change in current or flux through an aperture, or a constriction therein, by modulating a blockage current or flux through the aperture or constriction. Or, for example, the moiety can have a chemical or biological property that facilitates chemical or biological detection. Chemical or biological properties include presence of a chemical or biological group, e.g., a radioactive group or a group having enzymatic activity. One or more electrical, physical, chemical, biological, or other flux blockade properties of the moiety can provide a measurable change in current through an aperture or constriction, or an optical signal. In one illustrative example, movement of the moiety within an aperture causes a measurable change in a current through an aperture or constriction, or causes a measurable change in flux of molecules through an aperture or constriction, which change in flux can be electrically, chemically, biologically, or optically detectable. An abasic nucleotide is one non-limiting example of a moiety the movement of which can cause a measurable change in a current through an aperture or constriction or a measurable change in flux of molecules through an aperture or constriction.

As used herein, "motion" or "movement" can be translational, rotational, or conformational, or a combination thereof.

As used herein, "action" of a polymerase upon a nucleotide can include the nucleotide entering an active site on the polymerase. Action of a polymerase upon a nucleotide also can include, but is not limited to, the polymerase causing a chemical change to the nucleotide or a portion of that nucleotide. Chemical changes can include the polymerase removing a portion of the nucleotide, the polymerase adding the nucleotide to another molecule, the nucleotide binding or debinding from the polymerase, the polymerase modifying the nucleotide or a portion thereof, and the polymerase forming or cleaving a chemical bond, e.g., during polynucleotide synthesis, and the like. For example, action of a polymerase upon a nucleotide can include adding the nucleotide to a polynucleotide. Action of a polymerase upon a nucleotide optionally can include both motion and chemical change of the polymerase, the nucleotide, or both. As non-limiting, purely illustrative examples, action of a polymerase upon a nucleotide can include one or more of: a polymerase testing a nucleotide, the polymerase rejecting a nucleotide if the nucleotide is a mismatch to the next nucleotide in a polynucleotide that is being sequenced, the polymerase excising a nucleotide from a polynucleotide using exonuclease activity, and the polymerase excising a nucleotide from a polynucleotide using pyrophosphorylysis. FIG. 8 illustrates exemplary reaction parameters, e.g., rate constants and dwell times, for reaction schemes in which a nucleotide respectively being acted upon by a polymerase is a match or a mismatch (adapted from Johnson, "The kinetic and chemical mechanism of high-fidelity DNA polymerases," Biochim Biophys Acta 1804(5): 1041-1048 (2010), the entire contents of which are incorporated by reference herein). Polymerases such as T7 Pol typically discriminate between match and mismatch nucleotides based on a combination of increased binding affinity for the correct match nucleotide (e.g., approximately 10-fold preference correct vs. mismatch), greatly reduced catalytic rate for mismatch nucleotide (e.g., approximately 1000-fold slower for mismatch), and a greatly increased off-rate for the mismatch nucleotide from the closed catalytic state (e.g., approximately 300-fold faster for mismatch).

As used herein, a "conformational change" is intended to mean a change in shape of a molecule (e.g., a change in relative atomic coordinates of a molecule). Such a conformational change can include a portion of a molecule moving relative to another portion of the molecule. The chemical reactivity of a portion of the molecule can change responsive to the relative motion of that portion, or another portion, of the molecule. A molecule can undergo a conformational change responsive to a stimulus. Such a stimulus can include, but is not limited to, changes to or forces applied to the molecule, interactions with other molecules, or environmental factors. Changes to or forces applied to the molecule can include a physical force applied to the molecule or a portion thereof, an electrical field applied to the molecule, or a chemical reaction with the molecule or a portion thereof, or a combination thereof, e.g., binding of a substrate, catalysis, and/or release of a product. Interactions with other molecules can include the presence of another molecule, a concentration of another molecule, an action by or upon another molecule, or a combination thereof. An exemplary interaction with another molecule includes hybridization of two oligonucleotides, or a polymerase acting upon a nucleotide. Environmental factors can include a change in pH or a change in temperature, or a combination thereof.

As used herein, the term "nucleotide" is intended to mean a molecule that includes a sugar and at least one phosphate group, and optionally also includes a nucleobase. A nucleotide that lacks a nucleobase can be referred to as "abasic." Nucleotides include deoxyribonucleotides, modified deoxyribonucleotides, ribonucleotides, modified ribonucleotides, peptide nucleotides, modified peptide nucleotides, modified phosphate sugar backbone nucleotides, and mixtures thereof. Examples of nucleotides include adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP), and deoxyuridine triphosphate (dUTP).

The term "nucleotide" also is intended to encompass any nucleotide analogue which is a type of nucleotide that includes a modified nucleobase, sugar and/or phosphate moiety compared to naturally occurring nucleotides. Exemplary modified nucleobases that can be included in a polynucleotide, whether having a native backbone or analogue structure, include, inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thiouracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. As is known in the art, certain nucleotide analogues cannot become incorporated into a polynucleotide, for example, nucleotide analogues such as adenosine 5'-phosphosulfate.

Exemplary nucleotides modified at a phosphate moiety include, for example, the nucleotide analogues described by Lee et al., "Synthesis and reactivity of novel γ-phosphate modified ATP analogues," Bioorganic & Medicinal Chemistry Letters 19: 3804-3807 (2009); Kumar et al, "PEG-labeled nucleotides and nanopore detection for single molecule DNA sequencing by synthesis," Scientific Reports 2: 684 (2012); Kumar et al., "Terminal phosphate labeled nucleotides: synthesis, applications, and linker effect on incorporation by DNA polymerases," Nucleosides, Nucleotides, and Nucleic Acids 24: 401-408 (2005), and Mulder et al., "Nucleotide modification at the γ-phosphate leads to the improved fidelity of HIV-1 reverse transcriptase," Nucleic Acids Research 33: 4865-4873 (2005), the entire contents of which are incorporated by reference herein. Lee et al. describes certain exemplary γ-phosphate modified ATP analogues having the following structures:

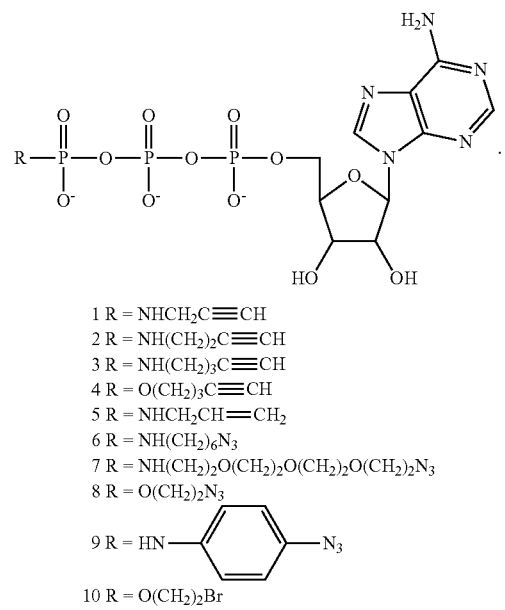

1 R = NHCH$_2$C≡CH
2 R = NH(CH$_2$)$_2$C≡CH
3 R = NH(CH$_2$)$_3$C≡CH
4 R = O(CH$_2$)$_3$C≡CH
5 R = NHCH$_2$CH=CH$_2$
6 R = NH(CH$_2$)$_6$N$_3$
7 R = NH(CH$_2$)$_2$O(CH$_2$)$_2$O(CH$_2$)$_2$O(CH$_2$)$_2$N$_3$
8 R = O(CH$_2$)$_2$N$_3$
9 R = HN—⟨phenyl⟩—N$_3$
10 R = O(CH$_2$)$_2$Br Kumar et al. (2012) discloses different length PEG-coumarin tags which can be attached to the terminal phosphate of dNTP or NTP (dNTP/NTP) or to the terminal phosphate of tetraphosphate nucleotides (dN4P/N4P). Exemplary lengths include, for example, coumarin-PEG$_{16}$-dN4P/N4P, coumarin-PEG$_{20}$-dN4P/N4P, coumarin-PEG$_{24}$-dN4P/N4P, and coumarin-PEG$_{36}$-dN4P/N4P. Kumar et al. (2005) discloses tetra- and penta-phosphate-modified nucleotides including dyes attached with or without linkers. As described in Kumar et al. (2005) exemplary dyes attached without linkers include DDAO, RESORUFIN, COUMARINS, alkyl-XANTHENES, nitrophenol, hydroxyindole, ELF, and BBT; exemplary dyes attached via linkers include R110, REG, TAMRA, ROX, Cy dyes, and ET dyes; and exemplary linkers include diaminopropane, diaminoheptane, diaminododecane, EEA, PAP, diaminocyclohexane, diamino-xylene, and penta-lysine. Mulder et al. discloses chemically modified nucleotides including 1-aminonaphthalene-5-sulfonate (ANS) attached to the γ-phosphate of a nucleotide, e.g., γ-P-aminonaphthalene-5-sulfonate deoxy or ribonucleotides (dNTP or NTP) such as ANS-ATP, ANS-CTP, ANS-GTP, and ANS-TTP and/or the deoxy forms of these or other nucleotides.

As used herein, the term "polynucleotide" refers to a molecule that includes a sequence of nucleotides that are bonded to one another. Examples of polynucleotides include deoxyribonucleic acid (DNA), ribonucleic acid (RNA), and analogues thereof. A polynucleotide can be a single stranded sequence of nucleotides, such as RNA or single stranded DNA, a double stranded sequence of nucleotides, such as double stranded DNA, or can include a mixture of a single stranded and double stranded sequences of nucleotides.

Double stranded DNA (dsDNA) includes genomic DNA, and PCR and amplification products. Single stranded DNA (ssDNA) can be converted to dsDNA and vice-versa. The precise sequence of nucleotides in a polynucleotide can be known or unknown. The following are exemplary examples of polynucleotides: a gene or gene fragment (for example, a probe, primer, expressed sequence tag (EST) or serial analysis of gene expression (SAGE) tag), genomic DNA, genomic DNA fragment, exon, intron, messenger RNA (mRNA), transfer RNA, ribosomal RNA, ribozyme, cDNA, recombinant polynucleotide, synthetic polynucleotide, branched polynucleotide, plasmid, vector, isolated DNA of any sequence, isolated RNA of any sequence, nucleic acid probe, primer or amplified copy of any of the foregoing.

As used herein, "hybridize" is intended to mean noncovalently binding a first polynucleotide to a second polynucleotide. The strength of the binding between the first and second polynucleotides increases with the complementarity between those polynucleotides.

As used herein, the term "protein" is intended to mean a molecule that includes, or consists of, a polypeptide that is folded into a three-dimensional structure. The polypeptide includes moieties that, when folded into the three-dimensional structure, impart the protein with biological activity.

As used herein, the term "enzyme" is intended to mean a molecule that catalytically modifies another molecule. Enzymes can include proteins, as well as certain other types of molecules such as polynucleotides. Examples of enzymes that also are proteins include polymerases, exonucleases and helicases.

As used herein, a "polymerase" is intended to mean an enzyme having an active site that assembles polynucleotides by polymerizing nucleotides into polynucleotides. A polymerase can bind a primed single stranded polynucleotide template, and can sequentially add nucleotides to the growing primer to form a polynucleotide having a sequence that is complementary to that of the template.

Exemplary Compositions, Systems, and Methods for Sequencing Nucleotides

Exemplary compositions including tethers anchored to polymerases adjacent to nanopores now will be described with reference to FIGS. 1A-1D. Under one aspect, a composition includes a nanopore including a first side, a second side, and an aperture extending through the first and second sides. The composition also can include a plurality of nucleotides, wherein each of the nucleotides includes an elongated tag. The composition also can include first and second polynucleotides, the first polynucleotide being complementary to the second polynucleotide. The composition also can include a polymerase disposed adjacent to the first side of the nanopore, the polymerase configured to add nucleotides of the plurality of nucleotides to the first polynucleotide based on a sequence of the second polynucleotide. The composition also can include a permanent tether including a head region, a tail region, and an elongated body disposed there between, the head region being anchored to the polymerase, wherein the elongated body occurs in the aperture of the nanopore. The composition also can include a first moiety disposed on the elongated body, wherein the first moiety is configured to bind to the elongated tag of a first nucleotide upon which the polymerase is acting. The composition also can include one or more reporter regions disposed on the elongated body, wherein the one or more reporter regions are configured to indicate when the first nucleotide is complementary or is not complementary to a next nucleotide in the sequence of the second polynucleotide.

For example, FIG. 1A schematically illustrates a cross-section of an exemplary composition that includes nanopore 100, permanent tether 110, a plurality of nucleotides 120 (one of which is shown for simplicity of illustration), polymerase 130, first polynucleotide 140, and second polynucleotide 150. Nanopore 100 includes first side 101, second side 102, aperture 103, and constriction 104. Permanent tether 110 includes head region 111, tail region 112, and elongated body 113. In the embodiment illustrated in FIG. 1A, polymerase 130 is disposed adjacent to first side 101 of nanopore 100, head region 111 of permanent tether 110 is anchored to polymerase 130, tail region 112 of permanent tether 110 is freely disposed on second side 102 of nanopore 100, and elongated body 113 of permanent tether 110 is movable within aperture 103 of nanopore 100. Elongated body 113 of permanent tether 110 includes first moiety 115 and one or more reporter regions 114. Nucleotide 120 includes elongated tag 121, which includes second moiety 122. Polymerase 130 is configured to add nucleotides of the plurality of nucleotides 120 to first polynucleotide 140 based on a sequence of second polynucleotide 150.

Figure 1B:
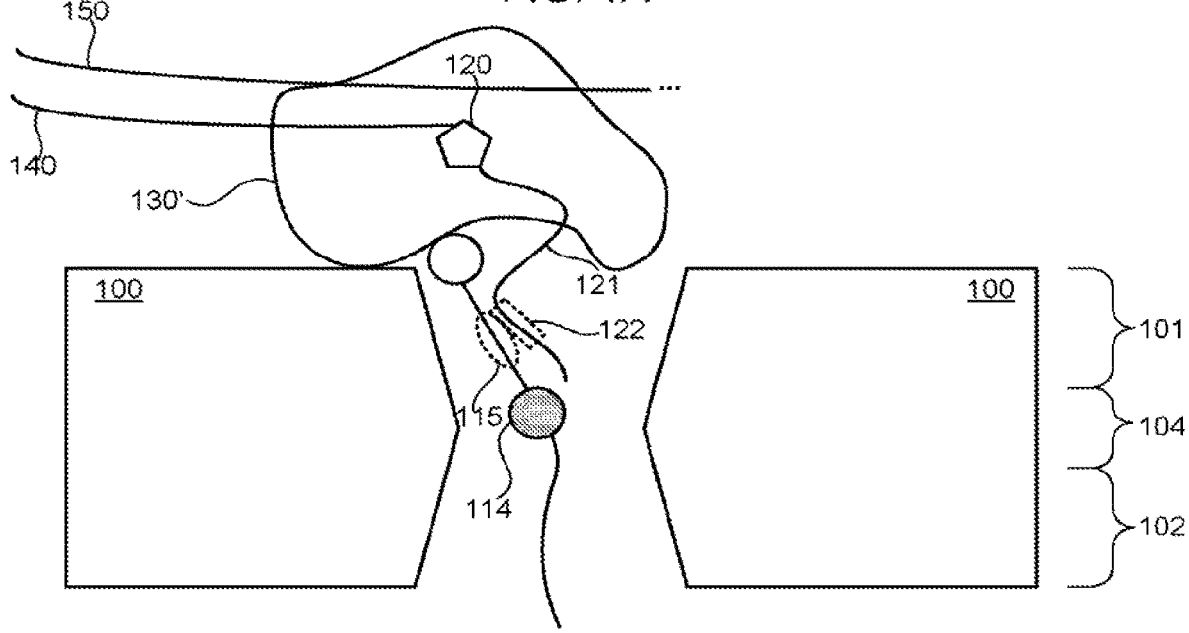
Figure 1C:
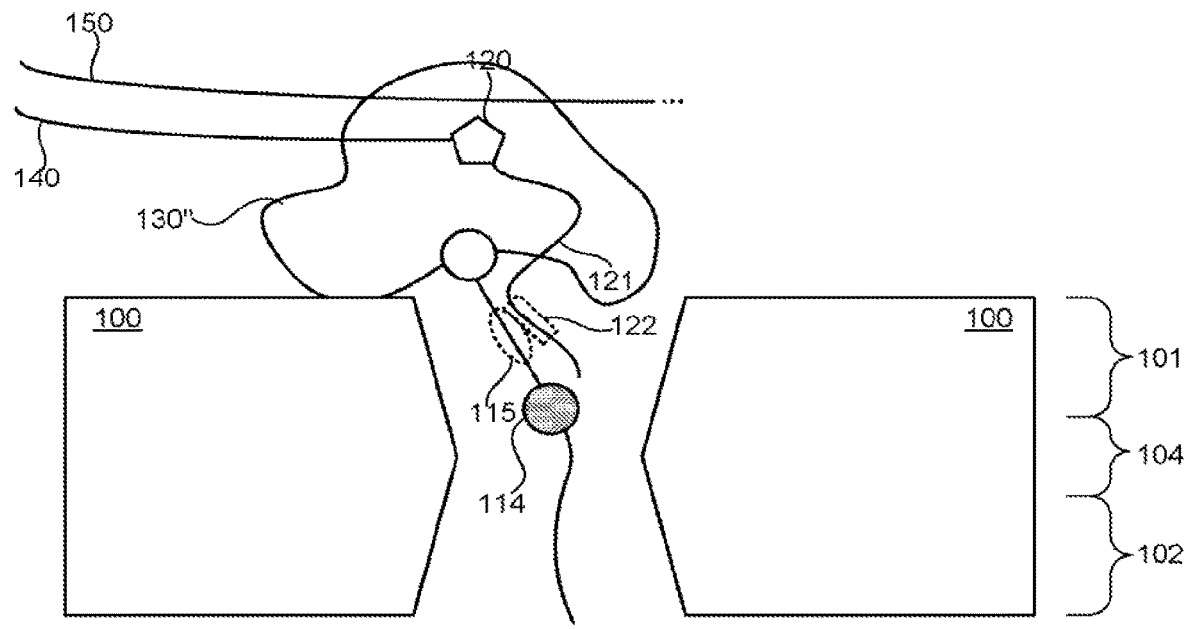
Figure 1D:
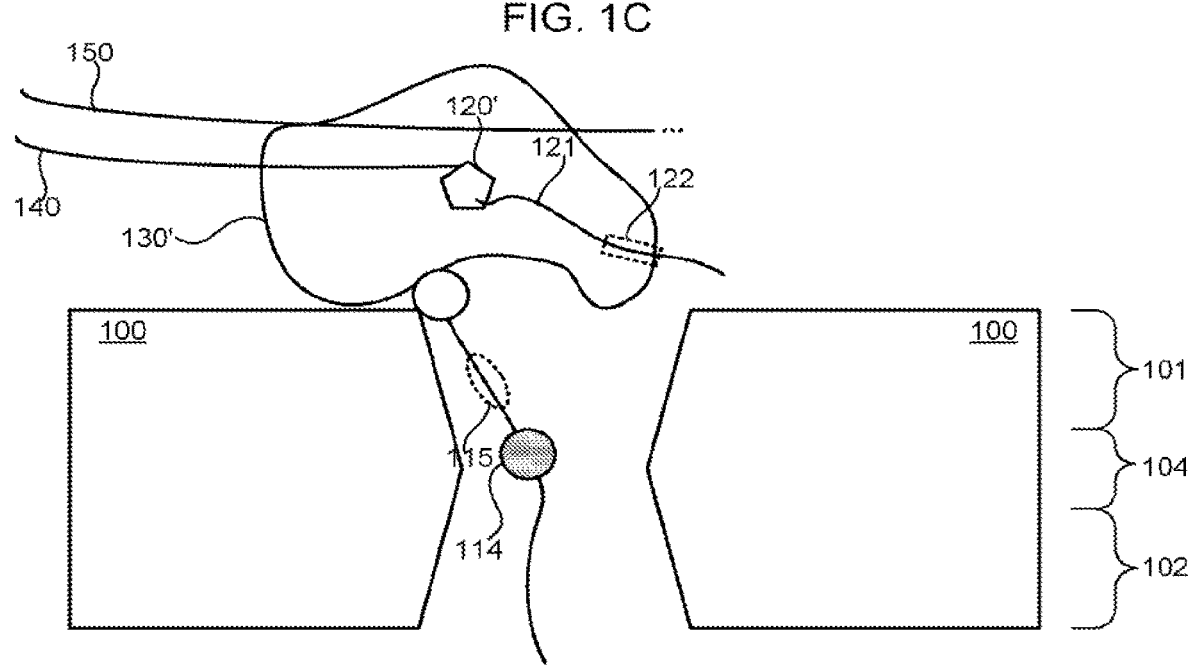

As illustrated in FIG. 1B, based upon polymerase 130 acting upon nucleotide 120, first moiety 115 of elongated body 113 of permanent tether 110 is configured to bind to elongated tag 121 of nucleotide 120, e.g., is configured to bind to second moiety 122. For example, polymerase 130 can include an active site (not specifically illustrated) that receives and binds nucleotide 120, which places second moiety 122 relatively close to first moiety 115 for a sufficient amount of time for first moiety 115 and second moiety 122 to interact with one another, e.g., to bind with one another (which also can be referred to as forming a duplex with one another). For example, in some embodiments, first moiety 115 includes a first oligonucleotide, and second moiety 122 includes a second oligonucleotide that is complementary to, and hybridizes with, the first oligonucleotide.

First moiety 115 can be configured to generate at least a first signal state responsive to polymerase 130 acting upon nucleotide 120, and nucleotide 120 can be identifiable based upon the first signal state in a manner such as described in greater detail elsewhere herein. For example, formation of a duplex between moiety 115 and moiety 122 can cause one or more reporter regions 114 to become disposed at a location within aperture 103 that results in a unique current or flux through aperture 103 based upon which nucleotide 120 can be identified. Illustratively, the first signal state can include an electrical signal or an optical signal.

Additionally, one or more reporter regions 114 of elongated body 113 of permanent tether 110 can be configured to indicate when nucleotide 120 is complementary or is not complementary to a next nucleotide in the sequence of second polynucleotide 150. For example, in some embodiments, the position of one or more reporter regions 114 within aperture 103 can be based upon the particular conformation of polymerase 130, which can be based upon whether nucleotide 120 is a match or a mismatch to the next nucleotide in the sequence of second polynucleotide 150. For further details regarding differences in polymerase conformation and kinetics between match and mismatch nucleotides, see the following references, the entire contents of each of which are incorporated by reference herein: Freudenthal et al., "New structural snapshots provide molecular insights into the mechanism of high fidelity DNA synthesis," DNA Repair, doi:10.2016/j.dnarep/2015.04.007

(available online Apr. 30, 2015); Freudenthal et al., "Watching a DNA polymerase in action," Cell Cycle 13: 691-692, doi:10.4161/cc.27789 (2014); and Freudenthal et al., "Observing a DNA polymerase choose right from wrong," Cell 154: 157-168, doi:10.1016/j.cell.2013.05.048 (2013).

For example, as is illustrated in FIG. 1B, polymerase 130 can have a modified conformation 130' based upon nucleotide 120 being a match to the next nucleotide in the sequence of second polynucleotide 150, which causes one or more reporter regions 114 to become disposed at a location within aperture 103 that results in a unique current or flux through aperture 103 based upon which it can be determined that nucleotide 120 is a match. In comparison, as is illustrated in FIG. 1B, polymerase 130 can have a modified conformation 130" based upon nucleotide 120 not being a match to the next nucleotide in the sequence of second polynucleotide 150, which causes one or more reporter regions 114 to become disposed at a location within aperture 103 that results in a unique current or flux through aperture 103 based upon which it can be determined that nucleotide 120 is a mismatch.

Note that in the embodiment illustrated in FIG. 1B, reporter region(s) 114 can provide an indication of match or mismatch while moiety 115 and moiety 122 are bound to one another. Alternatively, as is illustrated in FIG. 1D, polymerase 130 again can have a modified conformation 130' based upon nucleotide 120 being a match to the next nucleotide in the sequence of second polynucleotide 150, which causes reporter region(s) 114 to become disposed at a location within aperture 103 that results in a unique current or flux through aperture 103 based upon which it can be determined whether nucleotide 120 is a match or a mismatch. However, moiety 115 and moiety 122 need not necessarily be bound to one another in order for reporter region(s) 114 to provide such an indication. For example, moiety 115 and moiety 122 can dissociate from one another, e.g., responsive to thermal fluctuations within aperture 103, or responsive to application of a sufficient potential difference between first side 101 and second side 102, and the position of reporter region(s) 114 within aperture 103 while moieties 115 and 122 are dissociated from one another can indicate whether nucleotide 120 is a match or a mismatch. In comparison, if nucleotide 120 is a mismatch, then polymerase 130 can have a conformation 130" analogous to that illustrated in FIG. 1C, which causes reporter region(s) 114 to become disposed at a location within aperture 103 that results in a unique current or flux through aperture 103 based upon which it can be determined that nucleotide 120 is a mismatch.

Additionally, based upon nucleotide 120 being a match, polymerase 130 can incorporate nucleotide 120 into first polynucleotide, and can cleave elongated tag 121 from nucleotide 120, which can diffuse away on the cis side (e.g., first side) of nanopore 100. Additionally, based upon polymerase 130 successfully incorporating nucleotide 120 into first polynucleotide 140, polymerase 130 can release pyrophosphate or other phosphorous oxyanion that may have two or more phosphate subunits, e.g., two, three, four, five, or six phosphate subunits (not specifically illustrated). Additionally, based upon polymerase 130 not successfully incorporating nucleotide 120 into first polynucleotide 140, polymerase 130 does not release pyrophosphate.

Reporter region 114 is configured so as to generate one or more signals based on one or more of the effects resulting from nucleotide 120 being acted upon by polymerase 130 or resulting from nucleotide 120 being complementary or not complementary to a next nucleotide in the sequence of second polynucleotide 150, e.g., based on one or more of the effects of nucleotide 120 being bound to or residing in an active site of polymerase 130 or of polymerase 130 successfully or not successfully incorporating nucleotide 120 into first polynucleotide 140. Further details of such exemplary second signal states are described in greater detail below with reference to FIGS. 3, 4A-4F, 5A-5D, and 6. It can be detectable based upon the one or more signals whether the first nucleotide is being acted upon by polymerase 130 or whether the first nucleotide complementary or is not complementary to the next nucleotide of the second polynucleotide, or both is being acted upon by polymerase 130 and whether the first nucleotide complementary or is not complementary to the next nucleotide of the second polynucleotide. Illustratively, each of the one or more signals independently can include an electrical signal or an optical signal.

Optionally, elongated body 113 can include more than one reporter region, e.g., can include any suitable number of reporter regions, e.g., one, or two, or three, or four, or five, or more than five reporter regions. Each such reporter region can be the same as each other reporter region. Alternatively, each such reporter region can be different than each other reporter region. Or, some reporter regions can be the same as one another, while other reporter regions can be different than one another. In one illustrative, non-limiting example, elongated body 113 includes a polynucleotide that includes one or more abasic nucleotides that define reporter region 114. An abasic nucleotide can be detected within an aperture of a nanopore as described, for example, in Wilson, "Electronic Control of DNA Polymerase Binding and Unbinding to Single DNA Molecules Tethered in a Nanopore," Ph.D. Thesis, University of California Santa Cruz (2009), the entire contents of which are incorporated by reference herein. Illustratively, movement or presence of one or more abasic nucleotides or other suitable reporter region(s) 114 can cause a measurable change in a current through aperture 103 or constriction 104, a measurable change in flux of molecules through aperture 103 or constriction 104, or an optical signal. For example, a change in flux of molecules through aperture 103 or constriction 104 can be detected electrically, chemically, biologically, or optically.

In the embodiments illustrated in FIGS. 1A-1D, head region 111, tail region 112, and elongated body 113 of tether 110 can include any suitable material or combination of materials. For example, head region 111 can be configured so as to be anchored to polymerase 130 via a chemical bond, e.g., via a covalent bond, hydrogen bond, ionic bond, dipole-dipole bond, London dispersion forces, or any suitable combination thereof. For example, head region 111 can include a first moiety that is bonded, e.g., covalently, to a second moiety of polymerase 130. Exemplary covalent bonds that can anchor head region 111 to polymerase 130 include carbon-carbon bonds, carbon-nitrogen bonds, carbon-oxygen bonds, oxygen-oxygen bonds, sulfur-sulfur bonds, phosphorus-oxygen bonds, phosphorus-sulfur bonds, amide bonds, thioether bonds, hydrazide bonds, carbon-sulfur bonds, and bonds that result from the reaction of oxyamine with carbonyls (aldehydes and ketones), of Staudinger reagent pairs such as phosphine and azides, or click chemistry pairs such as azides and alkynes. However, the attachment need not be covalent. For example, such attachment can be formed through hybridization of a first oligonucleotide of the head region to a second oligonucleotide of polymerase 130. Alternatively, such attachment can be formed using physical or biological interactions e.g., an interaction between a first protein structure of the head region and a second protein structure of polymerase 130 that inhibits detachment of the head region from polymerase 130. For example, head region 111 can include a first alpha helix and polymerase can include a second alpha helix that locks to head region 111 so as to inhibit dissociation of head region 111 from polymerase. Interactions between receptors and ligands are also useful, examples of which include avidin-biotin, or analogs thereof; antibody-epitope; lectin-carbohydrate, and the like.

Elongated body 113 can be attached, e.g., covalently bonded, to head region 111, and tail region 112 can define an end of elongated body 113 that is distal from head region 111. Elongated body 113 can include any suitable material of biological origin or a non-biological origin, or a combination thereof. As described in greater detail herein, elongated body 113 can include one or more reporter regions that indicate when a nucleotide upon which polymerase 130 is acting is complementary or is not complementary to a next nucleotide in the sequence of second polynucleotide 150. Elongated body 113 also can include first moiety 115 that can interact with, e.g., bind to, elongated tag 121 of nucleotide 120 upon which polymerase 130 is acting. Exemplary biological materials that can be included within elongated body 113 include biological polymers such as polynucleotides, polypeptides, polysaccharides, and analogs of the aforementioned. Exemplary synthetic polymers that suitably can be included within elongated body 113 include PEG (polyethylene glycol), PPG (polypropylene glycol), PVA (polyvinyl alcohol), PE (polyethylene), LDPE (low density polyethylene), HDPE (high density polyethylene), polypropylene, PVC (polyvinyl chloride), PS (polystyrene), NYLON (aliphatic polyamides), TEFLON® (tetrafluoroethylene), thermoplastic polyurethanes, polyaldehydes, polyolefins, poly(ethylene oxides), poly($\omega$-alkenoic acid esters), poly(alkyl methacrylates), and other polymeric chemical and biological linkers such as described in Hermanson et al., mentioned further above.

Nanopore 100 can have any suitable configuration that permits disposing polymerase 130 adjacent to first side 101 of nanopore 100 such that head region 111 of tether 110 is anchored to polymerase 130 and elongated body 113 of tether 110 occurs in, e.g., can be disposed in, aperture 103 of nanopore 100. In some embodiments, nanopore 100 can be a biological pore, solid state pore, or a biological and solid state hybrid pore. A biological pore is intended to mean a pore that is made from one or more materials of biological origin. "Biological origin" refers to material derived from or isolated from a biological environment such as an organism or cell, or a synthetically manufactured version of a biologically available structure. Biological pores include, for example, polypeptide pores and polynucleotide pores.

A polypeptide pore is intended to mean a pore that is made from one or more polypeptides. The one or more polypeptides can include a monomer, a homopolymer or a heteropolymer. Structures of polypeptide pores include, for example, an $\alpha$-helix bundle pore and a $\beta$-barrel pore as well as all others well known in the art. Exemplary polypeptide pores include $\alpha$-hemolysin, Mycobacterium smegmatis porin A, gramicidin A, maltoporin, OmpF, OmpC, PhoE, Tsx, F-pilus, SP1, mitochondrial porin (VDAC), Tom40, outer membrane phospholipase A, and Neisseria autotransporter lipoprotein (NaIP). "Mycobacterium smegmatis porin A (MspA)" is a membrane porin produced by Mycobacteria, allowing hydrophilic molecules to enter the bacterium. MspA forms a tightly interconnected octamer and transmembrane beta-barrel that resembles a goblet and includes a central constriction. For further details regarding $\alpha$-hemolysin, see U.S. Pat. No. 6,015,714, the entire contents of which are incorporated by reference herein. For further details regarding SP1, see Wang et al., Chem. Commun., 49:1741-1743, 2013, the entire contents of which are incorporated by reference herein. For further details regarding MspA, see Butler et al., "Single-molecule DNA detection with an engineered MspA protein nanopore," Proc. Natl. Acad. Sci. 105: 20647-20652 (2008) and Derrington et al., "Nanopore DNA sequencing with MspA," Proc. Natl. Acad. Sci. USA, 107:16060-16065 (2010), the entire contents of both of which are incorporated by reference herein. Other pores include, for example, the MspA homolog from Norcadia farcinica, and lysenin. For further details regarding lysenin, see PCT Publication No. WO 2013/153359, the entire contents of which are incorporated by reference herein.

A polynucleotide pore is intended to mean a pore that is made from one or more nucleic acid polymers. A polynucleotide pore can include, for example, a polynucleotide origami.

A solid state pore is intended to mean a pore that is made from one or more materials of non-biological origin. "Solid-state" refers to materials that are not of biological origin. A solid-state pore can be made of inorganic or organic materials. Solid state pores include, for example, silicon nitride pores, silicon dioxide pores, and graphene pores.

A biological and solid state hybrid pore is intended to mean a hybrid pore that is made from materials of both biological and non-biological origins. Materials of biological origin are defined above and include, for example, polypeptides and polynucleotides. A biological and solid state hybrid pore includes, for example, a polypeptide-solid state hybrid pore and a polynucleotide-solid state pore.

It should be appreciated that different types of nanopores can have different dimensions than one another in multiple respects. For example, as illustrated in FIG. 1A, nanopore 100 can be characterized as having a first dimension H1 defining a thickness of nanopore 100, e.g., a thickness between an outer surface of first side 101 and an outer surface of second side 102, adjacent to aperture 103. In embodiments in which nanopore 100 includes constriction 104, nanopore 100 also can be characterized as having a second dimension H2 defining a constriction depth, e.g., a depth between the outer surface of first side 101 and the narrowest portion of constriction 104, adjacent to aperture 103. Nanopore 100 also can be characterized as having a first diameter D1 defining a diameter of aperture 103, e.g., a diameter of aperture 103 at the aperture's widest point. In embodiments in which nanopore 100 includes constriction 104, nanopore 100 also can be characterized as having a second diameter D2 defining a constriction diameter, e.g., a diameter of constriction 104 at the constriction's narrowest point. It should be appreciated that such dimensions of nanopore 100 should not be construed as limiting, and that other dimensions of nanopore 100 can be suitably defined. For example, first dimension H1 of nanopore 100 can vary along the lateral dimension, e.g., if nanopore 100 includes a relatively thin barrier in which a relatively thick pore is disposed. Or, for example, in embodiments in which nanopore 100 includes constriction 104, second dimension H2 of nanopore 100 can vary depending on the relative location of constriction 104 to the outer surface of first side 101. That is, constriction 104 can be located disposed at any suitable location within nanopore 100, and indeed can even be disposed distal to the outer surface of first side 101 or second side 102. Aperture 103 and constriction 104 need not necessarily be perfectly circular, and still can be characterized as having an approximate diameter or using any other suitable dimensions. Moreover, nanopore 100 can include multiple constrictions, each of which suitably can be characterized using appropriate dimensions.

In some embodiments, first dimension H1 of nanopore 100 is about 100 nm or smaller, or about 50 nm or smaller, or about 20 nm or smaller, or about 10 nm or smaller, or about 5 nm or smaller, or about 2 nm or smaller. For example, H1 can be between about 2 nm and about 100 nm, or between about 5 nm and about 50 nm, or between about 10 nm and about 20 nm. In embodiments that include constriction 104, second dimension H2 of nanopore 100 is about 100 nm or smaller, or about 50 nm or smaller, or about 20 nm or smaller, or about 10 nm or smaller, or about 5 nm or smaller, or about 2 nm or smaller, or about 1 nm or smaller. For example, H2 can be between about 1 nm and about 100 nm, or between about 2 nm and about 50 nm, or between about 5 nm and about 20 nm. Illustratively, H1 can be between about 5 nm and about 50 nm, and H2 can be between about 1 nm and about 5 nm. In one exemplary embodiment, H1 is about 10 nm and H2 is about 5 nm. In another exemplary embodiment, H1 is about 10 nm and H2 is about 6 nm. In another exemplary embodiment, H1 is about 10 nm and H2 is about 7 nm. In another exemplary embodiment, H1 is about 10 nm and H2 is about 8 nm. In another exemplary embodiment, H1 is about 10 nm and H2 is about 9 nm. In another exemplary embodiment, H1 is about 10 nm and H2 is about 10 nm. In another exemplary embodiment, H1 is about 5 nm and H2 is about 2 nm. In another exemplary embodiment, H1 is about 5 nm and H2 is about 3 nm. In another exemplary embodiment, H1 is about 5 nm and H2 is about 4 nm. In another exemplary embodiment, H1 is about 5 nm and H2 is about 5 nm. The terms "approximately" and "about" are intended to mean within 10% above or below the stated value.

In some embodiments, first diameter D1 of aperture 103 of nanopore 100 is about 100 nm or smaller, or about 50 nm or smaller, or about 20 nm or smaller, or about 10 nm or smaller, or about 5 nm or smaller, or about 2 nm or smaller. For example, D1 can be between about 2 nm and about 100 nm, or between about 5 nm and about 50 nm, or between about 10 nm and about 20 nm. In embodiments including constriction 104, second diameter D2 of constriction 104 of nanopore 100 is about 100 nm or smaller, or about 50 nm or smaller, or about 20 nm or smaller, or about 10 nm or smaller, or about 5 nm or smaller, or about 2 nm or smaller, or about 1 nm or smaller. For example, D2 can be between about 1 nm and about 100 nm, or between about 2 nm and about 50 nm, or between about 5 nm and about 20 nm. Illustratively, D1 can be between about 5 nm and about 50 nm, and D2 (if applicable) can be between about 1 nm and about 5 nm.

In one illustrative embodiment, D1 is about 5 to 10 nm, and D2 is about 1 to 1.2 nm. In another illustrative embodiment, D1 is about 5 to 10 nm, and D2 is about 1.2 to 1.4 nm. In yet another illustrative embodiment, D1 is about 5 to 10 nm, and D2 is about 1.4 to 1.6 nm. In yet another illustrative embodiment, D1 is about 5 to 10 nm, and D2 is about 1.6 to 1.8 nm. In yet another illustrative embodiment, D1 is about 5 to 10 nm, and D2 is about 1.8 to 2.0 nm. In exemplary embodiments where the pore is MspA, D1 can be, for example, about 4.8 nm, D2 can be, for example, about 1.1 to 1.2 nm, H1 can be, for example, about 9.6 nm, and H2 can be, for example, about 7.9 to 8.1 nm. In exemplary embodiments where the pore is α-hemolysin, D1 can be, for example, about 2.6 nm, D2 can be, for example, about 1.4 to 1.5 nm, H1 can be, for example, about 10 nm, and H2 can be, for example, about 5 nm. Other suitable combinations of dimensions suitably can be selected for other types of pores.

The characteristics of permanent tether 110 can be suitably selected based on one or more of the dimensions of nanopore 100. For example, elongated body 113 of tether 110 can have a width selected based on D1 or D2, or both D1 and D2. For example, the width of elongated body 113 can be selected such that elongated body 113 is movable within aperture 103, e.g., elongated body 113 has a width that is smaller than first diameter D1 of aperture 103. In embodiments that include constriction 104, the width of elongated body 113 also can be selected such that at least a portion of elongated body 113 is movable adjacent to constriction 104, e.g., has a width that is equal to, or smaller than, second diameter D2. Optionally, in embodiments that include constriction 104, the width of elongated body 113 also can be selected such that at least a portion of elongated body 113 is movable through constriction 104, e.g., has a width that is sufficiently smaller than second diameter D2 to permit movement of elongated body 113 through constriction 104. If nanopore 100 includes multiple constrictions (not specifically illustrated), then the width of elongated body 113 can be selected such that elongated body 113 is movable through some or all of such constrictions as appropriate.

The length of elongated body 113 of tether 110 can be selected based on H1 or H2, or both H1 and H2. For example, the length of elongated body 113 can be selected so as to be shorter than H1, so that tail region 112 would not extend beyond the outer surface of the second side 102 of nanopore 100 even if elongated body 113 were fully extended through constriction 104 toward second side 102. Or, for example, in embodiments including constriction 104, the length of elongated body 113 can be selected so as to be shorter than H2, so that tail region 112 would not extend beyond constriction 104 of nanopore 100 even if elongated body 113 were fully extended toward second side 103. In other embodiments, the length of elongated body 113 can be selected so as to be longer than H1, so that tail region 112 would extend beyond the outer surface of the second side 102 of nanopore 100 if elongated body 113 were fully extended through constriction 104 toward second side 102. Or, for example, in embodiments that include constriction 104, the length of elongated body 113 can be selected so as to be longer than H2, so that tail region 112 would extend beyond constriction 104 of nanopore 100 if elongated body 113 were fully extended toward second side 103.

The length of elongated body 113 can be selected so as to permit relatively free movement of elongated body 113 within aperture 103, at least on first side 101 of nanopore 100, substantially without steric hindrance or other interference caused by the elongated body itself. That is, elongated body 113 can be configured so as to occupy only a portion of the volume of aperture 103 on first side 101 of nanopore 100, e.g., so as to occupy less than 50% of the volume of aperture 103 on first side 101 of nanopore 100, or less than 20% of the volume of aperture 103 on first side 101 of nanopore 100, or less than 10% of the volume of aperture 103 on first side 101 of nanopore 100, or less than 5% of the volume of aperture 103 on first side 101 of nanopore 100, or less than 1% of the volume of aperture 103 on first side 101 of nanopore 100. Additionally, in the embodiment illustrated in FIGS. 1A-1D, tail region 112 of tether 110 can be unattached to nanopore 100 or to any other member, thus permitting relatively free movement of the entirety of elongated body 113 relative to head region 111. Alternatively, in embodiments such as described below with reference to FIGS. 4A-4F, 5A-5D, and 6, tail region 112 can be attached to another member so as to inhibit dissociation of polymerase 130 from nanopore 100.

In one non-limiting example, one or more reporter regions 114 can facilitate measurement of translational, rotational, or conformational movement or presence (or a combination thereof) of elongated body 113 responsive to polymerase 130 acting upon nucleotide 120 or responsive to a conformational change of polymerase 130 based upon nucleotide 120 being complementary or not complementary to a next nucleotide in the sequence of second polynucleotide 140, or responsive both to polymerase 130 acting upon nucleotide 120 and a conformational change of polymerase 130 based upon nucleotide 120 being complementary or not complementary to a next nucleotide in the sequence of second polynucleotide 140. In one exemplary embodiment, dimension D1 of aperture 103 suitably is selected so as to facilitate the use of reporter region(s) to measure movement of elongated body 113. For example, aperture 103 can be sufficiently narrow so as to measurably interact with one or more reporter regions 114 responsive to movement of reporter region(s) 114. As one example, reporter region 114 has an electrical or flux blockade characteristic, and aperture 103 has a width selected such that movement of reporter region(s) 114 causes a detectable change in current or flux through aperture 103 under an applied voltage across nanopore 100. For example, nucleotides that are larger (such as A and G) can result in more blockage when they are disposed in an aperture, e.g., having an elongated tag disposed in the constriction of MspA, as compared with T, which has a smaller elongated tag. Exemplary ranges of blockage currents or fluxes in terms of % of open pore current or flux include 0 to 10%, 10% to 20%, 20% to 30%, 30% to 40%, 40% to 50%, 60% to 70%, 70% to 80%, 80% to 90%, and 90% to 100%. In one exemplary embodiment, the range is between 20% and 70% for MspA in 300 mM KCl with a 180 mV bias and an open pore current or flux of 110 pA. Other non-limiting examples of reporter regions 114 are provided in greater detail herein.

Although FIG. 1A illustrates one exemplary arrangement of the components of nanopore 100, polymerase 130, and permanent tether 110, it should be understood that other arrangements suitably can be used. For example, polymerase 130 having head region 111 anchored thereto instead can be disposed adjacent to second side 102. Or, for example, tail region 112 of permanent tether 110 instead can be disposed on first side 101 of nanopore 100. Or, for example, tail region 112 of permanent tether 110 instead can be anchored to either the first side 101 or second side 102 of nanopore 100, or to another member that is disposed on either the first side 101 or second side 102 of nanopore 100. Some of such combinations of features are described herein and in the provisional patent applications incorporated by reference herein, but it should be appreciated that all such combinations of features are contemplated and readily can be envisioned based on the teachings herein.

The lengths of the present elongated bodies suitably can be varied such that the present tail regions can be disposed at any suitable location relative to nanopore 100. For example, elongated body 113 need not necessarily be sufficiently long that tail region 112 be disposed beyond second side 102 of nanopore 100 in the manner illustrated in FIGS. 1A-1D. Instead, elongated body 113 can be sufficiently long that tail region 112 is disposed on first side 101 of nanopore 100, or can be sufficiently long that tail region 112 is disposed on second side 102 of nanopore 100 but not beyond second side 102. Additionally, the present tail regions need not necessarily extend freely, but instead can be attached to any suitable member.

Additionally, it should be appreciated that any suitable type of nanopore 100, any suitable type of polymerase 130, and any suitable type of permanent tether 110 can be used in the embodiments provided herein, e.g., such as illustrated in FIGS. 1A-1D. For example, as noted further above, the nanopore can include a biological pore, solid state pore, or a biological and solid state hybrid pore. For example, nanopore 100 can include one or more solid state materials. Exemplary solid state materials suitable for use in a solid state nanopore include silicon (Si), silicon nitride (SiN or $SiN_x$), graphene, and silicon oxide ($SiO_2$ or $SiO_x$). For further details regarding solid state nanopores, see the following references, the entire contents of each of which are incorporated by reference herein: Dekker, "Solid-state nanopores," Nature Nanotechnology 2: 209-215 (2007); Schneider et al., "DNA Translocation through Graphene Nanopores," Nano Letters 10: 3163-3167 (2010); Merchant et al. Nano Letters 10:2915-2921 (2010); and Garaj et al., "Graphene as a subnanometre trans-electrode membrane," Nature 467: 190-193 (2010). Biological pores include, for example, polypeptide pores and polynucleotide pores. Biological pores can be disposed within a barrier that includes a membrane of biological origin, or a solid state membrane. Non-limiting examples of biological nanopores include MspA and alpha hemolysin. Exemplary membranes of biological origin include lipid bilayers. Exemplary solid state membranes include silicon and graphene. For further details regarding exemplary hybrid nanopores and the preparation thereof, see the following references, the entire contents of each of which are incorporated by reference herein: Hall et al., "Hybrid pore formation by directed insertion of alpha hemolysin into solid-state nanopores," Nature Nanotechnology 5: 874-877 (2010), and Cabello-Aguilar et al., "Slow translocation of polynucleotides and their discrimination by α-hemolysin inside a single track-etched nanopore designed by atomic layer deposition," Nanoscale 5: 9582-9586 (2013).

In some embodiments such as described in greater detail below with reference to FIGS. 7A-7D and 8, polymerase 130 illustrated in FIGS. 1A-1D optionally can be modified so as to delay one or more reaction parameters during use of the composition illustrated in FIGS. 1A-1D to sequence a polynucleotide. For example, polymerase 130 optionally can be modified so as to delay release of pyrophosphate responsive to incorporation of nucleotide 130 into first polynucleotide 140.

Additionally, it should be appreciated that a head group of a tether can be attached to a polymerase in any number of ways. For example, well-known bioconjugate chemistry such as described by Hermanson, mentioned above, can be used. In illustrative embodiments, the polymerase includes a chemical moiety for forming an attachment such as a cysteine, or a peptide linker such as a SpyTag. Further information regarding spytags and use thereof to form attachments can be found, for example, in the following references, the entire contents of each of which are incorporated by reference herein: Zakeri et al., "Peptide tag forming a rapid covalent bond to a protein, through engineering a bacterial adhesin," Proc. Nat. Acad. Sci. USA 109: E690-E697 (2012), and Fierer et al., "SpyLigase peptide-peptide ligation polymerases affibodies to enhance magnetic cancer cell capture," Proc. Nat. Acad. Sci. USA 111: E1176-E1181 (2014). Other exemplary linkers include: NETS-esters, isocyanates, and isothicyanate linker conjugation to amines, maleimides to cysteines, Click-chemistry with azides to alkynes, use of fusion tags such as Halotag, Spycatcher-Spytag, and other similar protein-protein bioconjugation methods. For further information about exemplary linkages that can be used, see the following references, the entire contents of each of which are incorporated by reference herein: Hermanson, Bioconjugate Techniques, 2nd Ed., Elsevier, 2008; and Liu et al., "Specific Enzyme Immobilization Approaches and Their Application with Nanomaterials," Topics in Catalysis 55(16-18): 1146-1156 (2012).

Figure 2A:
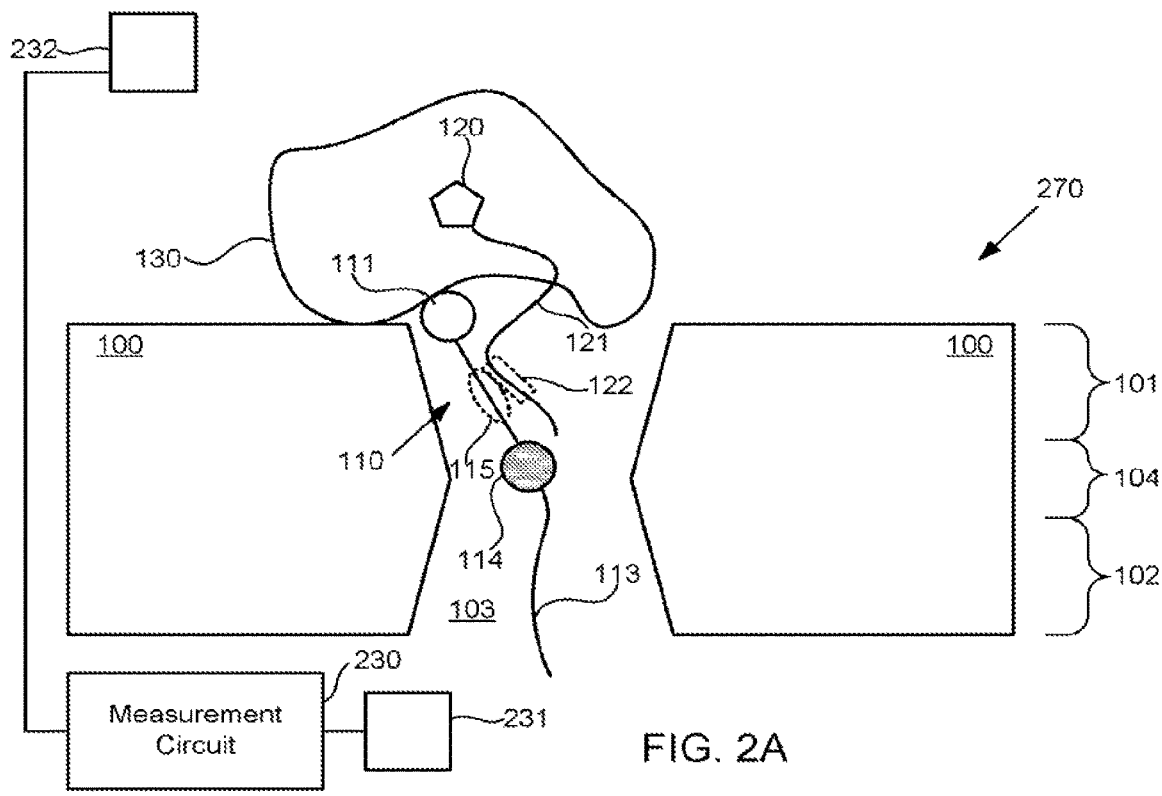
FIG. 2A schematically illustrates a system including measurement circuitry configured to measure movement of at least one reporter region within the aperture of a nanopore, according to some embodiments of the present invention.

Exemplary systems for sequencing polynucleotides using tethers anchored to polymerases adjacent to nanopores now will be described with reference to FIGS. 2A-2B. FIG. 2A schematically illustrates system 270 including a composition such as illustrated in FIGS. 1A-1D and measurement circuitry (e.g., electrical or optical measurement circuitry) configured to measure a current or flux state based upon one or both of binding of the first moiety 115 of an elongated body 113 to elongated tag 121 of nucleotide 120 upon which polymerase 130 is acting, and an indication by one or more reporter regions 114 when that nucleotide is complementary or is not complementary to a next nucleotide in the sequence of a second polynucleotide (second polynucleotide not specifically illustrated in FIG. 2A, but can be configured analogously as shown in FIGS. 1A-1D). System 270 includes nanopore 100, permanent tether 110, nucleotide 120, polymerase 130, and measurement circuit 230. Nanopore 100 includes first side 101, second side 102, aperture 103, and constriction 104. Permanent tether 110 includes head region 111, tail region 112, and elongated body 113. Nucleotide 120 includes elongated tag 121 and second moiety 122. Polymerase 130 can be configured analogously as described elsewhere herein. Additionally, elongated body 113 can include first moiety 115 that is configured to bind to elongated tag 121 of nucleotide 120 upon which polymerase 130 is acting, as well as reporter region(s) 114 configured to indicate when nucleotide 120 is complementary or is not complementary to a next nucleotide in the sequence of a second polynucleotide (not specifically, illustrated in FIG. 2A, but can be configured analogously as described above with reference to FIGS. 1A-1D).

In one illustrative example, nanopore 100, tether 110, nucleotide 120, polymerase 130, and first and second polynucleotides such as illustrated in FIGS. 1A-1D can be immersed in a conductive fluid, e.g., an aqueous salt solution. Measurement circuit 230 can be in communication with first electrode 231 and second electrode 232, and can be configured to apply a voltage between first electrode 231 and second electrode 232 so as to impose a voltage across nanopore 100. Either a direct-current (DC) or an alternating-current (AC) voltage suitably can be used. In some embodiments, measurement circuit 230 further can be configured to use first electrode 231 and second electrode 232 to measure the magnitude of a current or flux through aperture 103. In some embodiments, measurement circuit 230 further can include an optical, biological, or chemical sensor respectively configured to optically, biologically, or chemically sense the magnitude of a molecular flux through aperture 203. Exemplary optical sensors include CCDs and photodiodes. In some embodiments, measurement circuit includes one or more agents that chemically or biologically react with the molecular flux through aperture 103 so as to generate an optically detectable signal. Exemplary signals (e.g., optical or electrical signals) that can be generated using system 270 illustrated in FIG. 2A are described below with reference to FIGS. 4F and 6.

First moiety 115 of elongated body 113 of tether 110 can be configured to generate at least one signal responsive to polymerase 130 acting upon nucleotide 120, nucleotide 120 being identifiable based upon such signal. For example, as described above with reference to FIG. 1B and as illustrated in FIG. 2A, first moiety 115 can interact with, e.g., bind to, e.g., hybridize with, second moiety 122 of elongated tag 121. The binding of first moiety 115 to second moiety 122 can define a duplex that is sufficiently large as to be unable to pass through constriction 104 of nanopore 100, and instead can become lodged within, or adjacent to, constriction 104 under the voltage that first electrode 231 and second electrode 232 apply across nanopore 100. Moiety 122 of elongated tag 121 can be selected such that nucleotide 120 is identifiable based on the state of the current or flux through aperture 103 when the duplex is lodged within, or adjacent to, constriction 104. For example, each different type of nucleotide 120 (e.g., A, C, T, or G) can include a different respective elongated tag 121 than one another, e.g., each includes a different second moiety 122 that binds to a different portion of first moiety 115 than one another. In one non-limiting example, elongated tag 121 includes a first nucleotide sequence, and first moiety 115 includes a second nucleotide sequence that is complementary to the first nucleotide sequence. Measurement circuitry 230 can be configured to measure a corresponding current or flux state through aperture 103. Such current or flux state can be based on the elongated tag, nucleotide 120 being identifiable based on such current or flux state.

For example, moiety 122 of elongated tag 121 of a first nucleotide 120 (e.g., one of A, C, T, or G) can include a different nucleotide sequence than does moiety 122 of elongated tag 121 of a second nucleotide 120 (e.g., another of A, C, T, or G), and a different nucleotide sequence than does moiety 122 of elongated tag 122 of a third nucleotide 120 (e.g., yet another of A, C, T, or G), and a different nucleotide sequence than does moiety 122 of elongated tag 122 of a fourth nucleotide 120 (e.g., the remaining one of A, C, T, or G). Illustratively, each of the different moieties can bind (e.g., hybridize) to a different portion of first moiety 115 than one another, and, when the resulting duplex becomes lodged in or adjacent to constriction 104 (or otherwise interacts with constriction 104), results in a different current or flux state than one another. Additionally, or alternatively, lodging of the resulting duplex in or adjacent to constriction 104 (or otherwise interacts with constriction 104), can cause reporter region(s) 114 to become disposed at a location within aperture 103 results in a different current or flux state than does the other duplexes and corresponds to that nucleotide. Accordingly, based on the current or flux state through the aperture, corresponding to elongated tag 122 of the particular nucleotide 120 being acted upon by polymerase 130, such nucleotide is identifiable.

Reporter region(s) 114 can have a different physical, chemical, optical, electrical, biological, or other suitable flux blockade property than one or more other regions of elongated body 113, and can be configured to identify nucleotide 120 or to indicate when nucleotide 120 being acted upon by polymerase 130 or is complementary or is not complementary to a next nucleotide in the sequence of the second polynucleotide (not specifically shown in FIG. 2A, but can be configured as illustrated in FIGS. 1A-1D), or both to identify nucleotide 120 and to indicate when nucleotide 120 being acted upon by polymerase 130 or is complementary or is not complementary to a next nucleotide in the sequence of the second polynucleotide. For example, reporter region(s) can provide or generate one or more unique current or flux signatures (e.g., signal states) that individually identify the nucleotide being acted upon or individually indicate whether that nucleotide is complementary or is not complementary to the next nucleotide of the second polynucleotide, or both individually identify the nucleotide being acted upon and individually indicate whether that nucleotide is complementary or is not complementary to the next nucleotide of the second polynucleotide. For example, the reporter region(s) can generate a signal state (e.g., current or flux state) responsive to some or all of nucleotide 120 being bound by, or residing in, an active site of polymerase 130, nucleotide 120 being complementary to or not complementary to a next nucleotide in a polynucleotide being sequenced, or polymerase 130 successfully incorporating nucleotide 120 into the second polynucleotide at a position that complements the next nucleotide (not specifically shown in FIG. 2A, but can be configured as illustrated in FIGS. 1A-1D).

For example, a magnitude or a time duration of the conformational change of polymerase 130 can be responsive to nucleotide 120 being complementary or not complementary to the next nucleotide of the second polynucleotide, and a magnitude or a time duration, or both, of the corresponding signal can be based upon the conformational change of polymerase 130. Illustratively, in some embodiments, measurement circuit 130 can be configured to detect the position of reporter region(s) 114 relative to constriction 104, which position can indicate when the nucleotide upon which polymerase 130 is acting is complementary or is not complementary to a next nucleotide in the sequence of the second polynucleotide. For example, the position of reporter region(s) 114 can be based on a conformational change of polymerase 130 that can occur when polymerase 130 successfully adds nucleotide 120 to the first polynucleotide in a manner such as described elsewhere herein. Additionally, as noted elsewhere herein, in some embodiments, the position of reporter region(s) 114 relative to constriction 104 can be based upon the identity of nucleotide 120. Accordingly, a particular signal state (e.g., current or flux state) that can be measured (e.g., optically or electrically) by system 270 can indicate one or both of the identity of nucleotide 120 and whether nucleotide 120 is complementary or not to a next nucleotide in a polynucleotide being sequenced.

As another example, reporter region 114 can have a different physical property than some or all other regions of elongated body 113. For example, reporter region 114 can cause a differential blockage current or flux through aperture 103 as compared to other regions of elongated body 113. Additionally, or alternatively, reporter region 114 can have a different electrical or flux blockade property than some or all other regions of elongated body 113. For example, reporter region 114 can include an electrostatic charge, while some or all other regions of elongated body 113 can include a different electrostatic charge, or can be uncharged (e.g., can be electrically neutral). Or, for example, reporter region 114 can be uncharged, while some or all other regions of elongated body 113 can include an electrostatic charge. Or, for example, reporter region 114 can have a physical property. Physical properties include the volume and shape of reporter region 114. In one illustrative example, movement of reporter region 114 within aperture 103 causes a measurable change in current or flux through the aperture, or optional constriction 104 therein, by modulating a blockage current or flux through the aperture or constriction. Or, for example, reporter region 114 can have a chemical or biological property that facilitates chemical or biological detection. Chemical or biological properties include presence of a chemical or biological group, e.g., a radioactive group or a group having enzymatic activity.

One or more electrical, physical, chemical, optical, biological, or other flux blockade properties of reporter region 114 can provide a measurable change in current through aperture 103 or constriction 104, a measurable change in flux of molecules through aperture 103 or constriction 104, or an optical signal. In one illustrative example, movement or presence of reporter region 114 within aperture 103 causes a measurable change in a current through aperture 103 or constriction 104, or causes a measurable change in flux of molecules through aperture 103 or constriction 104, which change in flux can be electrically, chemically, biologically, or optically detectable. For example, presence or movement of reporter region 114 within aperture 103 or constriction 104 can cause an ionic current blockade or a molecular flux blockade, which can be detected optically, electrically, chemically, or biologically. Illustratively, a gradient of a molecule on the trans side can create a natural molecular flux that can be partially blocked by reporter region 114. Measurement circuitry 130 can be configured to measure such a molecular flux non-electrically (e.g., optically) using fluxes of luminescent (e.g., fluorescent or chemiluminescent molecules, or fluxes of reagents that become chemiluminescent in the presence of other reagents. For example, $Ca^{2+}$ can flux from one side of the nanopore to the other side where it encounters a calcium sensitive dye, such as Fluo-2, Fluo-4, Fluo-8, or the like, to induce fluorescence. Other reagent pairs that can be used include, but are not limited to, luminol and oxidants, calcium and aequorin, or ATP and luciferase, to name a few. For further details regarding optical detection of molecular fluxes through an aperture or constriction, see Ivankin et al., "Label-Free Optical Detection of Biomolecular Translocation through Nanopore Arrays," ACSNano 8(10): 10774-10781 (2014), the entire contents of which are incorporated by reference herein.

In non-limiting embodiments such as described in greater detail below with reference to FIGS. 4A-4F, 5A-5D, and 6, application of a sufficiently high voltage across nanopore 100 can cause a duplex formed by first moiety 115 and second moiety 122 to dissociate from one another, following which one or more reporter regions 114 can become disposed at a position within aperture 103 that is based upon the conformational state of polymerase 130. Accordingly, based upon a first signal state, nucleotide 120 can be identifiable, and a second signal state can indicate the conformational state of polymerase 130, which can indicate when nucleotide 120 is complementary or is not complementary to a next nucleotide in the sequence of the second polynucleotide. The voltage across nanopore 100 can be repeatedly reversed so as to facilitate repeated binding of first moiety and second moiety to one another, followed by measurement of the first signal state, followed by dissociation of first moiety and second moiety from one another, followed by measurement of the second signal state, for a desired number of times so as to identify nucleotide 120 upon which polymerase 130 is acting and so as to determine whether nucleotide 120 is complementary or is not complementary to a next nucleotide in the sequence of the second polynucleotide with desired accuracy.

In this regard, note that previously known real-time single molecule sequencing technologies are relatively error prone and exhibit relatively poor accuracy because such technologies may not sufficiently distinguish whether a nucleotide being acted upon actually is complementary or is not complementary to a next nucleotide in the sequence of a second polynucleotide, or if such nucleotide instead is a member of a "mismatch" complex with polymerase and primed nucleic acid. In comparison, the present compositions, systems, and methods can identify a nucleotide being acted upon, e.g., based on a first signal state, and also can determine whether that nucleotide is complementary or is not complementary to a next nucleotide in the sequence of a second polynucleotide (i.e., a match), based on a second signal state, and thus can greatly enhance accuracy of polynucleotide sequencing. It should be appreciated that other schemes for generating signal states indicating whether that nucleotide is complementary or is not complementary to a next nucleotide in the sequence of a second polynucleotide, such as provided herein, analogously can greatly enhance accuracy of polynucleotide sequencing.

For example, each of one or more reporter regions 114 can have a different physical property than some or all other regions of elongated body 113. In some embodiments, reporter region(s) 114 can cause a differential blockage current or flux through aperture 103 as compared to other regions of elongated body 113. Additionally, or alternatively, reporter region(s) 114 can have a different electrical or flux blockade property than some or all other regions of elongated body 113. For example, reporter region(s) 114 can include an electrostatic charge, while some or all other regions of elongated body 113 can include a different electrostatic charge, or can be uncharged (e.g., can be electrically neutral). Or, for example, reporter region(s) 114 can be uncharged, while some or all other regions of elongated body 113 can include an electrostatic charge. The state (e.g., magnitude) of the current or flux through aperture 103 can be based upon the position of reporter region(s) 114 within aperture 103, which can be based upon the conformational state of polymerase 130, and the time period for the current or flux state can be based on the duration of the one or more reporter regions' change in position. In one illustrative, non-limiting example, elongated body 113 includes a polynucleotide that includes one or more abasic nucleotides that define one or more reporter regions 114.

In one illustrative embodiment, nanopore 100 is a biological nanopore. Non-limiting examples of biological nanopores include MspA and alpha hemolysin. Reporter region 114 of tether 111 can include one or more abasic residues configured to be positioned within or adjacent to one or more constrictions 104 of the biological nanopore. Movement of one or more properly positioned abasic residues through a constriction of either pore can result in a readily detectable signal, e.g., a detectable change in current or flux through constriction(s) 104. Biological nanopores such as MspA and alpha hemolysin usefully can include constrictions that can serve to focus the effect of reporter region(s) 114. For example, MspA includes a single constriction with a diameter of approximately 1.2 nm and a length of approximately 0.5 nm, can provide suitable spatial resolution because the magnitude of the ionic current or flux blockade through the constriction primarily is based on the elongated-body segment threaded through the narrow region (constriction) of the nanopore.

In one illustrative embodiment, one or more reporter regions 114 include an electrostatic charge, and the first and second signal states generated by system 270, which respectively are responsive to the polymerase acting upon nucleotide 120 (for the first signal state) and indicate when nucleotide 120 is complementary or is not complementary to the next nucleotide of the second polynucleotide (for the second signal state) each include a state of the current or flux through constriction 104. However, it should be understood that measurement circuit 230 can include, or be in communication with, any element or combination of elements that facilitates measurement of any suitable reporter region(s), and need not necessarily be based on the measurement of current or flux through constriction 104 or even on the movement of the reporter region(s). Additionally, the reporter region(s) 114 need not necessarily be attached to tether 110, and instead can be attached to a nucleotide 120 or other molecule being acted upon, or can be attached to polymerase 130. For example, U.S. Patent Publication No. 2011/0312529 to He et al., the entire contents of which are incorporated by reference herein, discloses exemplary modified polymerases that can indicate a conformational state of the polymerase, e.g., are conformationally labeled.

The particular properties of the one or more reporter regions, e.g., reporter region(s) 114 or a reporter region disposed elsewhere in the composition and system, can be selected based on the particular configuration of system 270 so as to facilitate measurement of those reporter region(s). For example, one or more of the reporter regions can have an optical property, and system 270 can include, or be in communication with, an optical sensor configured to measure the optical property and to generate one or more signal states based on the identity of nucleotide 120 or when the nucleotide 120 upon which polymerase 130 is acting is complementary or is not complementary to a next nucleotide in the sequence of the second polynucleotide (not specifically illustrated in FIG. 2A but can be configured as described with reference to FIGS. 1A-1D) or based both on the identity of nucleotide 120 and when the nucleotide 120 upon which polymerase 130 is acting is complementary or is not complementary to a next nucleotide in the sequence of the second polynucleotide. In one illustrative embodiment, reporter region(s) 114 or other reporter region disposed elsewhere in the composition and system can include a first FRET pair partner, e.g., a FRET donor or acceptor, that interacts with a corresponding second FRET pair partner, e.g., a FRET acceptor or donor, so as to emit light of a particular wavelength that measurement circuit 230 is configured to detect. Or, for example, reporter region(s) 114 or other reporter region disposed elsewhere in the composition and system can have a chemical or biological property, and system 270 can include, or be in communication with, a chemical or biological sensor configured to measure the chemical or biological property and that generates a second signal state when the nucleotide 120 upon which polymerase 130 is acting is complementary or is not complementary to a next nucleotide in the sequence of the second polynucleotide (not specifically illustrated in FIG. 2A but can be configured as described with reference to FIGS. 1A-1D). As another example, the reporter region can provide a molecular flux blockade that modulates the flux of molecules through the aperture or constriction, which flux can be detected optically, electrically, chemically, or biologically.

In one non-limiting example, measurement circuit 230 is configured to measure a signal state generated by reporter region (s) 114 responsive to release of pyrophosphate or other phosphorous oxyanion responsive to polymerase 130 successfully incorporating nucleotide 120 into the first polynucleotide (not specifically illustrated in FIG. 2A but can be configured as described with reference to FIGS. 1A-1D). For example, reporter region(s) 114 can be configured to bind to pyrophosphate that is released responsive to polymerase 130 successfully incorporating nucleotide 120 into the first polynucleotide in a manner analogous to that described below with reference to FIGS. 11A-11C.

In this regard, note that polymerase 130 optionally can be modified so as to delay release of pyrophosphate responsive to incorporation of nucleotide 120 into the first polynucleotide. For example, in some embodiments, polymerase 130 can include a modified recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase. In some embodiments, polymerase 130 can include a modified recombinant Φ29 DNA polymerase having at least one amino acid substitution or combination of substitutions selected from the group consisting of: an amino acid substitution at position 484, an amino acid substitution at position 198, and an amino acid substitution at position 381. In some embodiments, polymerase 130 can include a modified recombinant Φ29 DNA polymerase having at least one amino acid substitution or combination of substitutions selected from the group consisting of E375Y, K512Y, T368F, A484E, A484Y, N387L, T372Q, T372L, K478Y, 1370 W, F198 W, and L381A. For further details regarding exemplary modified polymerases that can delay release of pyrophosphate responsive to incorporation of a nucleotide into a polynucleotide, see U.S. Pat. No. 8,133,672 to Bjornson et al., the entire contents of which are incorporated by reference herein.

Figure 11C:
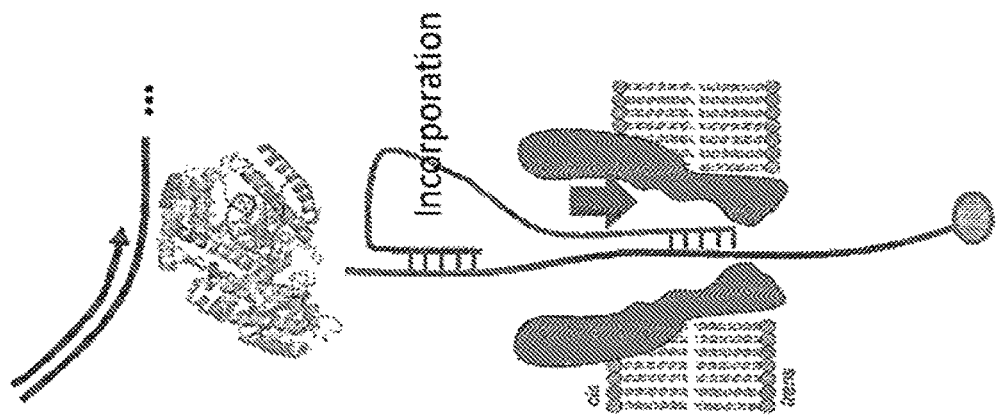
FIGS. 11A-11C schematically illustrate exemplary structures for use in modifying a kinetic constant in a reaction scheme that can be used in sequencing a polynucleotide, according to some embodiments of the present invention.
Figure 11B:
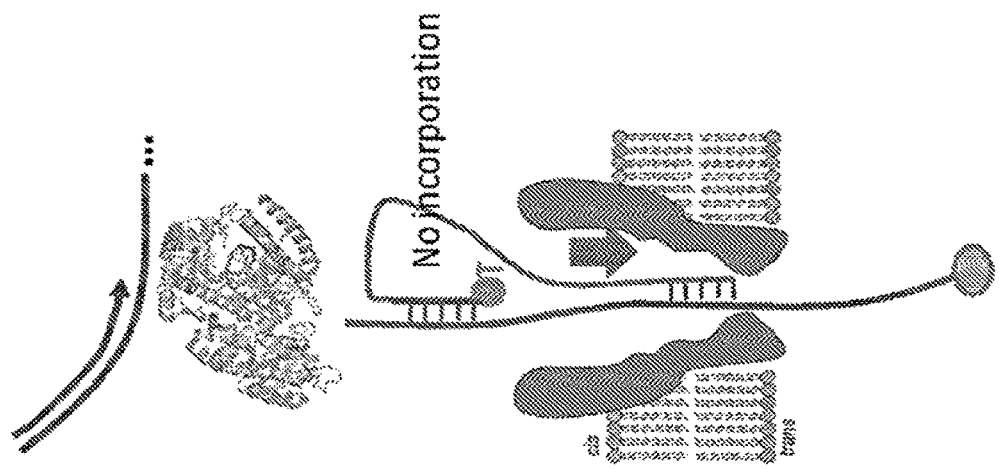
Figure 11A:
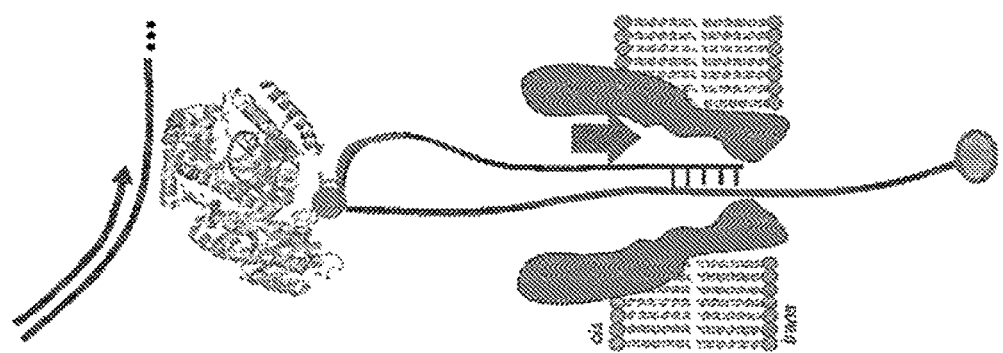

In another non-limiting example, measurement circuit 230 is configured to measure a signal state generated by reporter region(s) 114 responsive to release of elongated tag 121 responsive to polymerase 130 successfully incorporating nucleotide 120 into the first polynucleotide (not specifically illustrated in FIG. 2A but can be configured as described with reference to FIGS. 1A-1D). For example, reporter region(s) 114 can be configured to bind to a portion of elongated tag 121 that is released responsive to polymerase 130 successfully incorporating nucleotide 120 into the first polynucleotide. Illustratively, if an allosteric aptamer that can recognize the newly cleaved pyrophosphate and undergo a conformational change to expose an oligonucleotide is positioned on the linker portion of the tag, this aptamer can expose an oligonucleotide that binds to the tether upon successful incorporation. This binding can create a new stripping signal state. For example, in one non-limiting embodiment, the elongated tag attached to the nucleotide can include two moieties capable of hybridizing with the tether in a manner such as shown in FIGS. 11A-11C. One such moiety can be proximal to the phosphates and thus can be held away from the tether and close to the polymerase active site. The second such moiety can be distal to the nucleotide and can be capable of binding to the tether while the nucleotide is in the polymerase active site. A first stripping signal can be created by the distal moiety as long as the nucleotide is held in the active site and voltage cycling (AC) is occurring such as described elsewhere herein. This distal moiety signal can be indicative of the type of nucleotide in the active site. Based upon the nucleotide leaving the active site without phosphate cleavage and incorporation, the proximal moiety can hybridize with the tether, and can create a stripping signal that is affected by virtue of its remaining attachment to the nucleotide. Such a signal state can be indicative of the nucleotide not incorporating. Based upon phosphate cleavage and incorporation occurring, the proximal moiety can hybridize with the tether and can create a different stripping signal since the nucleotide is no longer present. Such a signal state can be indicative of nucleotide incorporation and phosphate cleavage.

It should be appreciated that an array of nanopores can be provided so as to sequence a plurality of polynucleotides in parallel with one another. For example, FIG. 2B schematically illustrates a plan view of a system 260 including measurement circuitry 240 configured to measure movement of one or more respective reporter regions within the respective apertures of an array of nanopores. A plurality of systems 250, each of which can be configured analogously to system 270 described above with reference to FIG. 2A, can be integrally disposed in a common substrate as one another, or can be separately prepared and disposed adjacent to one another. Each system 250 can include nanopore 100, a tether (tether not specifically illustrated), and an addressable electrode 241. Measurement circuit 240 can be configured analogously to measurement circuit 230, can be in electrical communication with each addressable electrode 241 of each system 250 via a suitable communication path, e.g., conductor (communication illustrated for only a single system 250) and with a common electrode 242. Measurement circuit 240 can be configured to selectably apply a voltage across each nanopore 100 by applying a voltage across the addressable electrode 241 of that nanopore and across common electrode 242, and to selectably measure a current or flux through that nanopore at the applied voltage. Analogous arrays readily can be envisioned for other types of detection systems, e.g., light, chemical, or biological detection systems.

Some exemplary methods for sequencing polynucleotides, and exemplary compositions that can be used during such methods, now will be described. Under one aspect, a method includes providing a nanopore including a first side, a second side, and an aperture extending through the first and second sides; providing a plurality of nucleotides, wherein each of the nucleotides comprises an elongated tag; and providing first and second polynucleotides, the first polynucleotide being complementary to the second polynucleotide. The method also can include providing a polymerase disposed adjacent to the first side of the nanopore, the polymerase configured to add nucleotides of the plurality of nucleotides to the first polynucleotide based on a sequence of the second polynucleotide, wherein the polymerase is anchored to a permanent tether including a head region, a tail region, and an elongated body disposed therebetween, the elongated body occurring in the aperture of the nanopore. The method also can include determining that a first nucleotide is being acted upon by the polymerase based on binding of the elongated tag to a first moiety disposed on the elongated body; and with one or more reporter regions disposed on the elongated body, indicating when the first nucleotide is complementary or is not complementary to a next nucleotide in the sequence of the second polynucleotide.

Figure 3:
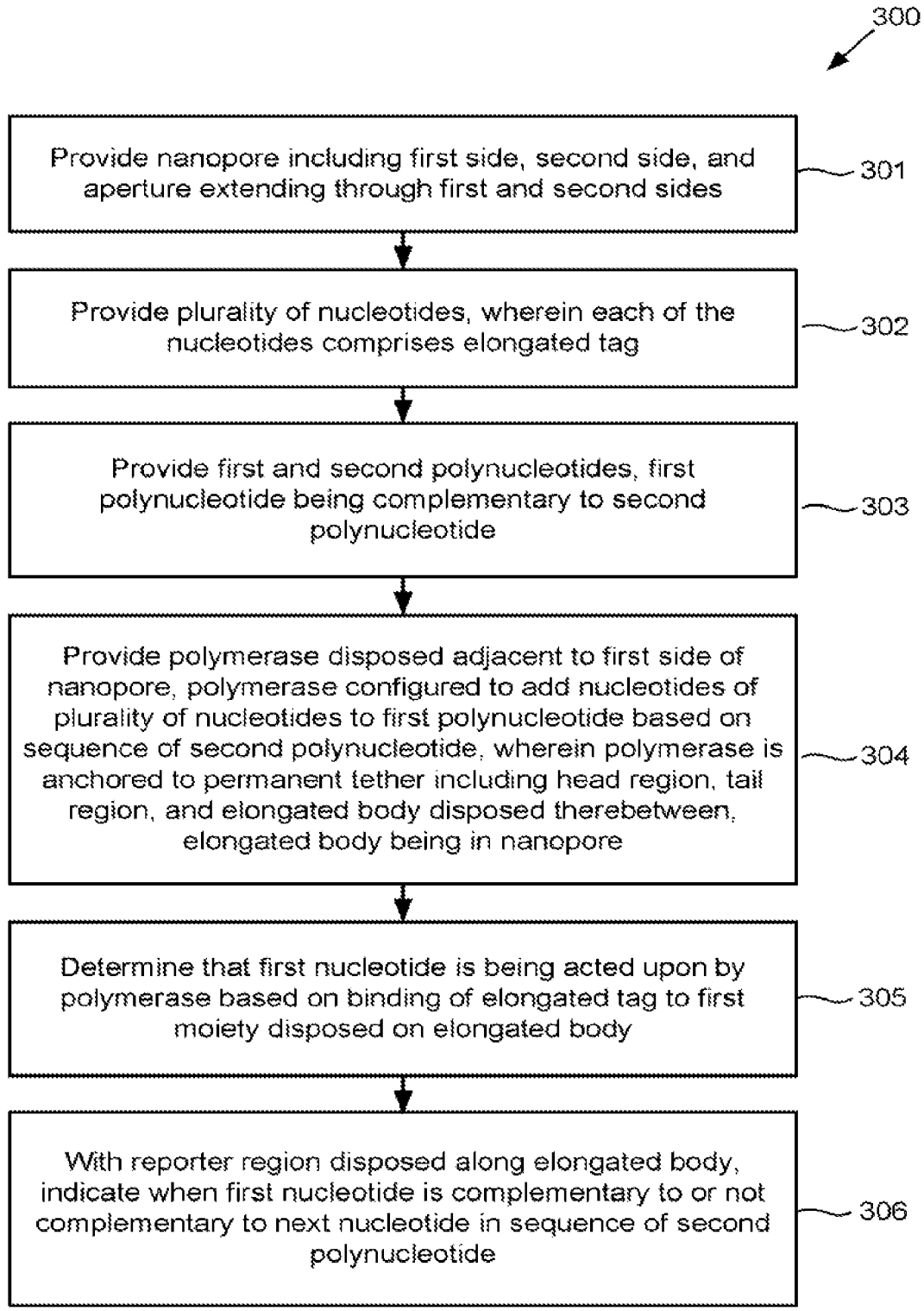
FIG. 3 illustrates a method for sequencing polynucleotides using a tether anchored to a polymerase adjacent to a nanopore, according to some embodiments of the present invention.

For example, FIG. 3 illustrates an illustrative method 300 for sequencing a polynucleotide using a composition including a tether anchored to a polymerase adjacent to a nanopore. Method 300 includes providing a nanopore including a first side, a second side, and an aperture extending through the first and second sides (step 301). The nanopore can have any suitable configuration, e.g., such as described above with reference to FIGS. 1A-1D. For example, nanopore 100 illustrated in FIG. 1A includes first side 101, second side 102, and aperture 103 extending through the first and second sides.

Step 301 also can, but need not necessarily, include preparing the nanopore. For example, step 301 can include defining a barrier and disposing a nanopore on or in the barrier. Methods of preparing nanopores are known in the art. For example, illustrative methods of preparing an MspA nanopore can be found in Butler et al., "Single-molecule DNA detection with an engineered MspA protein nanopore,"

Proc. Natl. Acad. Sci. 105: 20647-20652 (2008), the entire contents of which are incorporated by reference herein. Or, for example, illustrative methods of preparing an alpha hemolysin nanopore can be found in Howorka et al., "Sequence-specific detection of individual DNA strands using engineered nanopores," Nature Biotechnology 19: 636-639 (2001), and in Clarke et al., "Continuous base identification for single-molecule nanopore DNA sequencing," Nature Nanotechnology 4: 265-270 (2009), the entire contents of both of which are incorporated by reference herein.

Figure 9A:
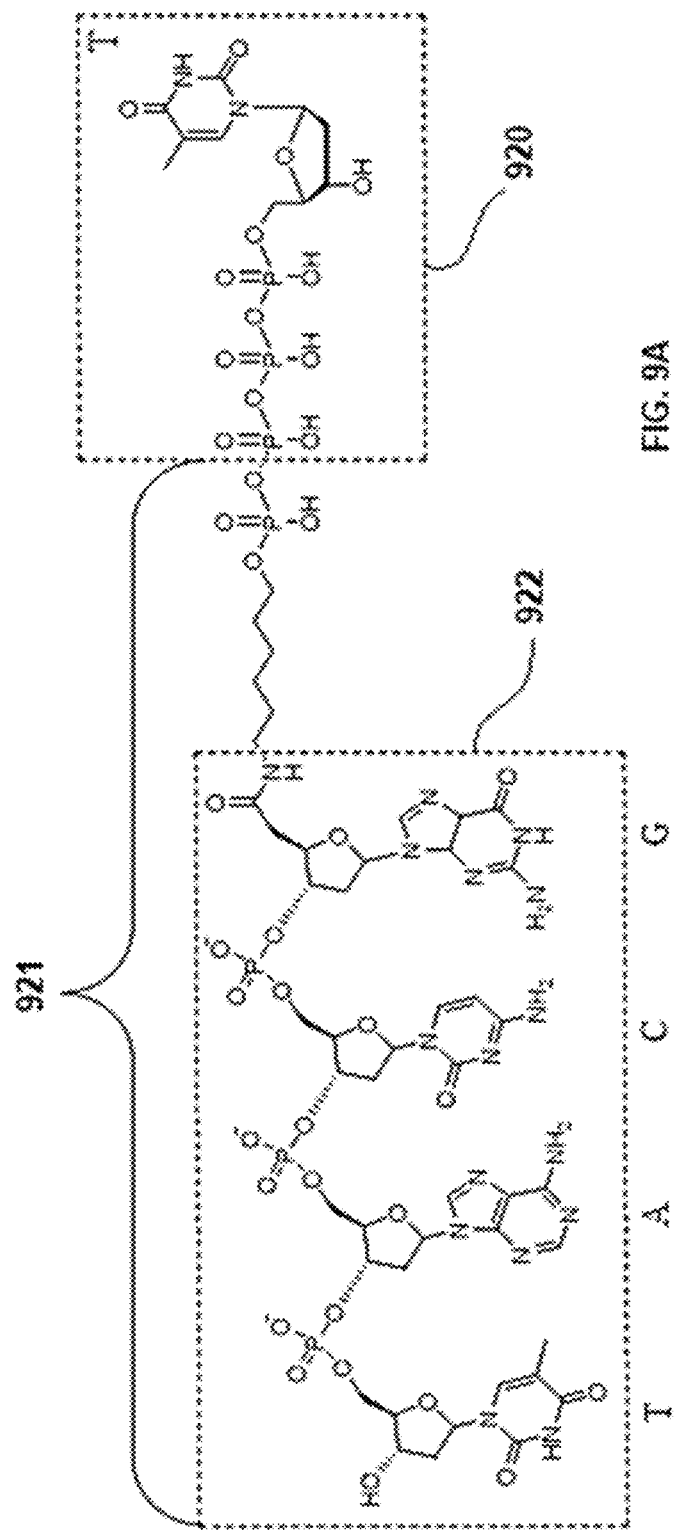
FIG. 9A schematically illustrates an exemplary nucleotide including an elongated tag including a moiety that interacts with a moiety of the tether described in FIGS. 1A-1D during use in sequencing a polynucleotide, according to some embodiments of the present invention.

Method 300 illustrated in FIG. 3 also includes providing a plurality of nucleotides, wherein each of the nucleotides includes an elongated tag (step 302). For example, FIG. 9A schematically illustrates an exemplary nucleotide 920 including an elongated tag 921 including a second moiety 922 that interacts with the first moiety 115 of tether 110 described in FIGS. 1A-1D during use in detecting a nucleotide upon which polymerase 130 is acting. In the non-limiting example illustrated in FIG. 9A, elongated tag 921 of exemplary nucleotide 920, e.g., T, can include an oligonucleotide moiety 922 attached to the gamma phosphate of the nucleotide 920, e.g., via a delta phosphate linkage. Oligonucleotide moiety 922 can include any suitable sequence of nucleotides selected to hybridize to a corresponding sequence of nucleotides within moiety 115 of tether 110. For example, oligonucleotide moiety 922 illustrated in FIG. 9A can include the exemplary sequence 5' GCAT 3', and moiety 115 can include the complementary sequence 5' ATGC 3'.

Each different type of nucleotide can include a corresponding elongated tag that is attached to its gamma phosphate in a manner analogous to that illustrated in FIG. 9A, or otherwise suitably attached. For example, FIGS. 9B-9C schematically illustrate exemplary nucleotides including elongated tags including respective moieties that interact with an exemplary tether during use in sequencing a polynucleotide. As shown in FIG. 9B, the A, T, C, and G nucleotides can include respectively elongated tags that include different moieties than one another, e.g., as respectively represented by the triangle, diamond, square, and circle. The particular moieties can be suitably selected so as to interact with, e.g., hybridize to, a corresponding moiety of the permanent tether, and to induce different respective conformational changes to the tether. FIG. 9C illustrates non-limiting examples of moieties that can be included in the elongated tags illustrated in FIG. 9B. Each such moiety can interact with, e.g., hybridize with, a different, respective portion of a corresponding moiety of the permanent tether, so as to induce a different, respective conformational change of the tether.

For example, FIG. 9D schematically illustrates an exemplary tether that includes head region 911, tail region 912, and elongated body 913 that includes one or more reporter region 914 and moiety 915. Head region 911 can include a chemical linker such as a 3' maleimide ("Mal") group for conjugation to a cysteine (Cys) residue on the pore. Tail region 912 can include a 5' phosphate group ("phos") that is charged and thus assists with feeding the tether through the aperture of the pore responsive to an applied voltage. Elongated body 913 can include a polymer, e.g., a polynucleotide such as illustrated in FIG. 9C, or any other suitable polymer, such as a biological polymer or a synthetic polymer. Reporter region 914 includes one or more abasic nucleotides denoted as "X", and in one exemplary embodiment can be located about 14-15 bases from the maleimide, which can be about the distance H2 from the pore mouth to the pore constriction for certain nanopore types. Moiety 915 can include a sequence of nucleotides, e.g., GGGTATAT, with which each of the moieties attached to the A, T, C, and G nucleotides to be acted upon can interact, e.g., hybridize, differently than one another.

Figures 10A, 10B:
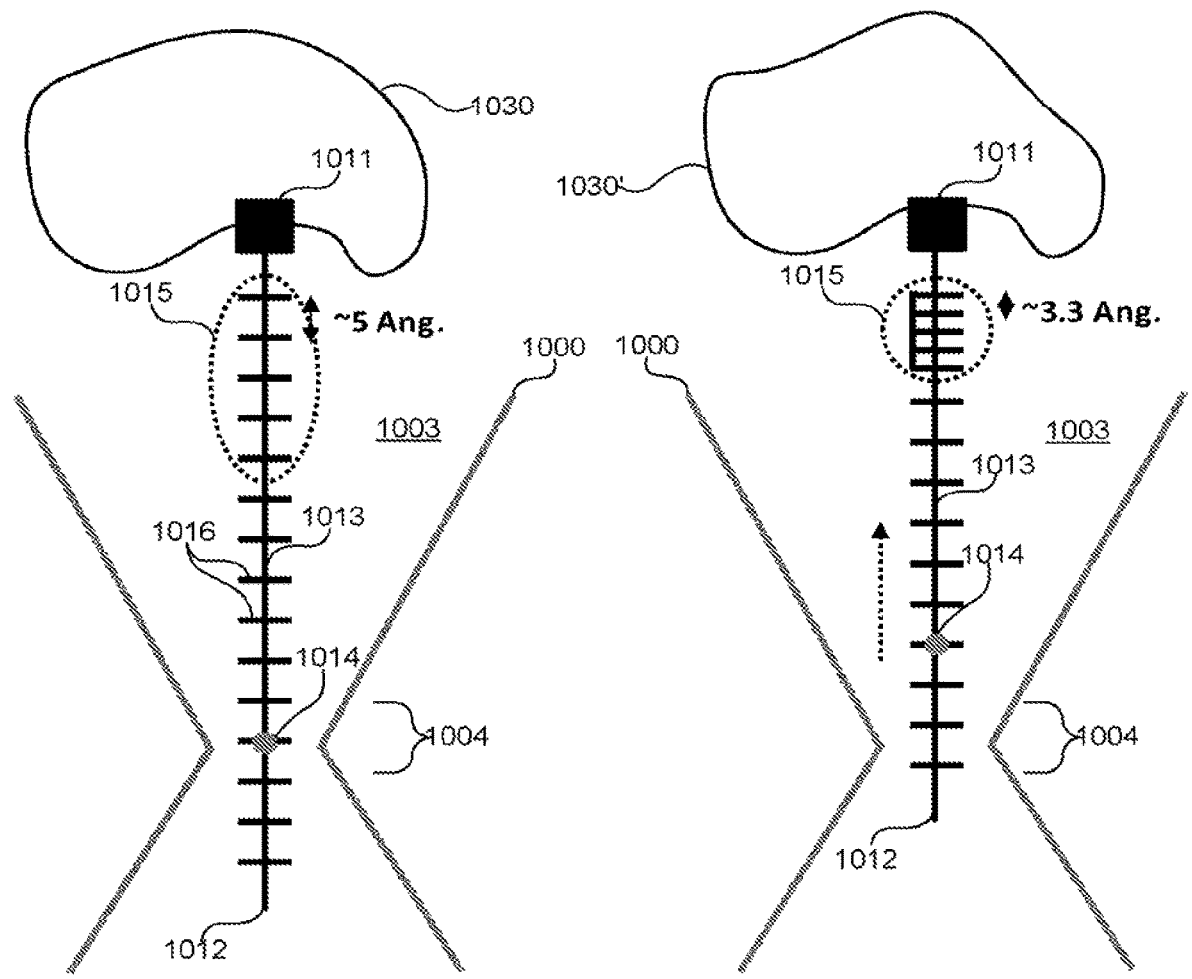
FIGS. 10A-10B schematically illustrate movement of an exemplary tether responsive to hybridization with a moiety of an elongated tag of an exemplary nucleotide during use in sequencing a polynucleotide, according to some embodiments of the present invention.

As provided herein, different types of interactions between a moiety of a permanent tether attached to a polymerase and moieties of nucleotides being acted upon can generate signal states based upon which the nucleotide can be identified or based upon which it can be determined whether that nucleotide is complementary to a next nucleotide in a polynucleotide being sequenced. FIGS. 10A-10B schematically illustrate movement of an exemplary tether responsive to hybridization with a moiety of an elongated tag of an exemplary nucleotide during use in sequencing a polynucleotide, according to some embodiments of the present invention. Head region 1011 of the tether is anchored to polymerase 1030 which is disposed adjacent to nanopore 100 that optionally includes constriction 1004, and elongated body 1013 extends through aperture 1003, e.g., such that reporter region 1014 is disposed within, or adjacent to, constriction 1014. In the embodiment illustrated in FIGS. 10A-10B, elongated body 1013 includes a polynucleotide such as ssDNA, the nucleotides of which are represented by horizontal bars 1016. Reporter region 1014 includes one or more abasic sites of the polynucleotide, e.g., ssDNA. Moiety 1015 includes a sequence of nucleotides that is selected so as to hybridize with a corresponding moiety, e.g., a complementary sequence of nucleotides, of an elongated tag of a nucleotide being acted upon by polymerase 1030 (nucleotide being acted upon, and elongated tag thereof, not specifically illustrated in FIGS. 10A-10B).

As illustrated in FIG. 10A, prior to binding of moiety 1015 to the corresponding moiety of the nucleotide being acted upon, nucleotides 1016 are spaced apart from one another by approximately 5 Angstroms. Additionally, polymerase 1030 can have a conformational state corresponding to a nucleotide not being bound by or residing in an active state of the polymerase. As illustrated in FIG. 10B, responsive to moiety 1015 interacting with, e.g., hybridizing to, the corresponding moiety of the nucleotide being acted upon, e.g., responsive to the moieties forming a double stranded DNA duplex, the spacing between nucleotides 1016 within moiety 1015 decreases to about 3.3 Angstroms. The change in length of the tether can be induced by the creation of double stranded DNA (dsDNA) from ssDNA that respectively is included within moiety 1015 and the moiety of the tag of the nucleotide being acted upon. For example, ssDNA is longer than dsDNA by about 1.5 Angstroms per nucleotide, which is within the resolution limits of the present systems, e.g., system 270 illustrated in FIG. 2A or system 260 illustrated in FIG. 2C. Each nucleotide can include a corresponding oligonucleotide moiety that is selected to create a different length of dsDNA upon hybridization of that moiety with moiety 1015, thus shortening the tether by a distance that corresponds to the nucleotide being acted upon by polymerase 1050. In some embodiments, the formula for the amount of shortening of a fully taut tether, such as a tether extended across the pore responsive to an applied voltage, can be expressed as:

$$D_s = N^* (L_{ss} - L_{ds}) \tag{1}$$

where N is the number of bases that are hybridized, $D_s$ is the distance by which the tether shortens, $L_{ss}$ is the length between nucleotides in ssDNA (approximately 5 Angstroms), and Las is the length between nucleotides in dsDNA (approximately 3.3 Angstroms). The short, black vertical line in FIG. 10B indicates a 5-base hybridization event, which shortens the tether and moves reporter region 1014 to a new location. Duplexes of 6, 7 or 8 bases can be even shorter than represented in FIG. 10B, e.g., as illustrated in FIGS. 9C-9D.

Additionally, based upon whether the nucleotide being acted upon is complementary or not to the next nucleotide in a polynucleotide being sequenced (polynucleotide not specifically illustrated), the conformation of polymerase 1030 can change. For example, as is illustrated in FIG. 10B, polymerase 1030 can have a modified conformation 1030' based upon the nucleotide being a match to the next nucleotide in the sequence of the polynucleotide being sequenced, which causes reporter region(s) 1014 to become disposed at a location within aperture 1003 that results in a unique current or flux through aperture 1003 based upon which it can be determined whether that nucleotide is a match. In comparison, polymerase 1030 can have a different modified conformation (e.g., conformation 1030" such as illustrated in FIG. 10C) based upon the nucleotide not being a match to the next nucleotide in the sequence of the polynucleotide being sequenced, which causes reporter region(s) 1014 to become disposed at a location within aperture 1003 that results in a unique current or flux through aperture 1003 based upon which it can be determined whether that nucleotide is mismatch. In this regard, note that the particular signal state (e.g., current or flux state) can indicate both the identity of the nucleotide and whether than nucleotide is a match or mismatch. Accordingly, it should be understood that different signal states, which can represent identities of nucleotides or whether such nucleotides are a match or a mismatch, need not necessarily occur at different times than one another, and indeed can occur at the same time as one other. For example, a measured signal (e.g., optical or electrical) can include a composite of more than one signal state (e.g., two signal states), each of which signal states provides information about one or more of an identity of a nucleotides or whether such nucleotide is a match or a mismatch.

Note that the moieties illustrated in FIGS. 9A-9D are intended to be purely exemplary, and not limiting of the invention. However, the moieties attached to the nucleotides to be acted upon can be selected so as satisfy one or more of the following parameters, and optionally all of the following parameters:

1. Moieties attached to different types of nucleotides than one another can interact with the moiety of the tether in a manner that is distinguishable from one another, e.g., via measurement of current or flux through the pore constriction.
2. The stability of a duplex between the moiety of the nucleotide and the corresponding moiety of the tether is sufficiently low that such moieties attached to "free" nucleotides (nucleotides that are not being acted upon by the polymerase and thus transiently interact with the tether) interact only briefly with the moiety of the tether, e.g., for less than 1 msec. For example, the stability of the duplex between the moiety of the nucleotide and the moiety of the tether can be expressed as the Tm, or melting temperature, of the duplex. The system operational temperature is expected to be about 20° C., or room temperature. Moieties that are about 5-8 nucleotides long are expected have Tm<12° C., which can provide sufficiently low stability at room temperature that moieties attached to "free" nucleotides will interact only briefly with the moiety of the tether.
3. The stability of a duplex between the moiety of the nucleotide and the corresponding moiety of the tether is sufficiently high that when the nucleotide is acted upon and held in place by the polymerase for the several milliseconds (1 to 30 msec, for example) during incorporation, such action increases the effective concentration of the moiety of the nucleotide relative to the moiety of the tether, which drives the reaction between the moieties forward and increases stability such that the effective Tm of the duplex is greater than 20° C. (or the anticipated operational temperature of the system), e.g., is greater than 30° C., or greater than 40° C., or greater than 50° C.
4. The length of the elongated tag of the nucleotide being acted upon, e.g., the length between the moiety and the gamma phosphate, can be sufficiently long that when the moiety is stably hybridized to the corresponding moiety of the tether, there is substantially no force on the nucleotide. If this length is too short, the tether can impose a force on the elongated tag of the nucleotide, which is expected to result in reduced polymerase efficiency.
5. With the tether attached to the polymerase, the position of the reporter can be expected to vary based upon whether the nucleotide in the active site of the polymerase is a match or a mismatch, because the conformation of the polymerase can be affected by the complementarity of the nucleotide to the next nucleotide in the polynucleotide being sequenced, and thus the relative position of the reporter region within the aperture, e.g., relative to the constriction. In this manner, the identity of the nucleotide as well as complementarity of the nucleotide can be discernable based on the position of the reporter in the pore constriction.

For further information about hybridizing oligonucleotides to one another, see U.S. Pat. No. 8,652,779 to Turner et al., the entire contents of which are incorporated by reference herein. According to Turner et al., at such a size scale, an oligonucleotide should sample its configuration space about 100-fold faster than a polymerase can incorporate a nucleotide. Applying such a principle to the present compositions, it is believed to be likely that the moiety of the nucleotide being acted upon will readily "find," and interact with, the corresponding moiety of the tether, and also will dissociate from the tether after the moiety is cleaved from the nucleotide being acted upon.

Note that in the exemplary moieties illustrated in FIG. 9D, each moiety attached to a nucleotide being acted upon has only a single matching hybridization with the corresponding tether moiety 915 that includes between 5 to 8 bases. While other hybridization options exist that do not cause complete hybridization, such options can be anticipated to be significantly less stable than the full-length options.

Referring again to FIGS. 1A-1C, the action of polymerase 130 upon nucleotide 120 can maintain moiety 122 in relatively close proximity to moiety 115 of tether 110, resulting in a transient increase in the local concentration of oligonucleotide moiety 122 that can induce temporary hybridization between moieties 122 and 115 preferentially to moieties that are attached to nucleotides not presently being acted upon by polymerase 130. Additionally, as noted above, polymerase 130 can cleave elongated tag 121 upon incorporating nucleotide 120 into a polynucleotide, responsive to which moiety 122 can dissociate from moiety 115. Suitable methods for providing nucleotides including elongated tags readily can be envisioned.

Method 300 illustrated in FIG. 3 also includes providing first and second polynucleotides, the first polynucleotide being complementary to the second polynucleotide (step 303). For example, step 303 can include providing a second polynucleotide, which also can be referred to as a "target" or "template," that is desired to be sequenced. Step 303 also can include providing a first polynucleotide that is complementary to the second polynucleotide, but that can be shorter than the second polynucleotide, using known methods. Illustratively, the first polynucleotide can include a primer that is complementary to, and that hybridizes with, a portion of the second polynucleotide.

Method 300 illustrated in FIG. 3 also includes providing a polymerase disposed adjacent to the first side of the nanopore (step 304). The polymerase can be configured to add nucleotides of the plurality of nucleotides (provided in step 302) to the first polynucleotide (provided in step 303) based on a sequence of the second polynucleotide (also provided in step 303). Exemplary suitable polymerases are described elsewhere herein or are known in the art. Optionally, the polymerase can be modified so as to generate a signal based on the conformation of the polymerase, e.g., as described in U.S. Patent Publication No. 2011/0312529 to He et al., or so as to slow release of pyrophosphate, e.g., as described in U.S. Pat. No. 8,133,672, the entire contents of both of which are incorporated by reference herein.

Additionally, the polymerase provided in step 304 can be anchored to a permanent tether including a head region, a tail region, and an elongated body therebetween, the elongated body including one or more reporter regions, the head region being anchored to or adjacent to the first side or second side of the nanopore. The tether can have any suitable configuration, such as described above with reference to FIGS. 1A-1D or otherwise provided herein. For example, the elongated body of the tether can be of a length that is longer than a first dimension H1 defining a thickness of the nanopore, e.g., such as illustrated in FIGS. 1A-1D. Or, for example, the elongated body can be of a length that is equal to a first dimension H1 defining a thickness of the nanopore, or that shorter than the first dimension H1. Or, for example, in embodiments that include a constriction, the elongated body can be of a length that is longer than a second dimension H2 defining a constriction depth, e.g., such as illustrated in FIGS. 1A-1D. Or, for example, in embodiments that include a constriction, the elongated body can be of a length that is shorter than the second dimension H2. Or, for example, the one or more reporter regions can be disposed at a location along the elongated body that is selected such that, based upon the elongated body being fully or partially extended when the head region is anchored to the polymerase, the polymerase is adjacent to the nanopore, and first moiety 115 of the elongated body being dissociated from second moiety 122 of the elongated tag, the reporter region(s) are positionable within the aperture of the nanopore, e.g., adjacent to or within a constriction, such as illustrated in FIGS. 1A-1D. Any suitable combination of such features can be used.

Step 304 also can, but need not necessarily, include preparing the tether. For example, step 304 can include defining an elongated body that includes portions thereof defining a head region, tail region, and one or more reporter regions. For example, as described elsewhere herein, a tether can include DNA. A DNA oligonucleotide of sufficient length can be prepared using procedures well known in the art. For example, oligonucleotides with a 5' or 3' primary amine can be purchased commercially from vendors such as Integrated DNA Technologies, Inc. (Coralville, Iowa). The oligonucleotide can be ordered so as to include one or more abasic moieties, which can be used as one or more reporter regions as described herein. A bifunctional linker, such as sulfo-SMCC (sulfosuccinimidyl-4-(N-maleimidomethyl) cyclohexane-1-carboxylate) that includes an amine reactive group (NHS) and a thiol reaction group (maleimide) can be readily obtained from commercial sources, e.g., from Thermo Fisher Scientific, Inc. (Rockford, Illinois). Such a linker can be reacted with the oligonucleotide under appropriate reaction conditions well known in the art to form a stable amide bond. After purification of the oligonucleotide from the unreacted sulfo-SMCC, the modified oligonucleotide (which is now thiol reactive by virtue of its maleimide group) can be reacted with the polymerase. The polymerase can be prepared in advance so as to include at least one solvent accessible cysteine residue that has its thiol (SH) group in reduced form. The reduced form can be obtained by incubation with 5 mM tris(2-carboxyethyl)phosphine (TCEP), for example, which is a readily available commercial compound. The modified oligonucleotide can be combined, e.g., in molar excess, with the reduced polymerase and under reaction conditions well known in the art, such that the maleimide forms a stable thioether bond. The polymerase-oligonucleotide conjugate can be purified away from excess unreacted oligonucleotide. In another example, compounds suitable for inclusion in a polyethylene glycol (PEG) based tether, e.g., maleimide-PEG, are readily available from commercial sources, such as Laysan Bio, Inc. (Arab, Alabama). For example, the maleimide can be conjugated to a reduced cysteine thiol in a manner analogous to that described above. One or more suitable reporter regions can be defined within the PEG. In another example, a disulfide bond between an oligonucleotide and an alpha hemolysin nanopore can be prepared in a manner such as described in Howorka et al., "Kinetics of duplex formation for individual DNA strands within a single protein nanopore," PNAS 98: 12996-13301 (2001), the entire contents of which are incorporated by reference herein.

Step 304 further can include disposing the elongated body of the tether within an aperture of the nanopore. Based on the length of the elongated body, the elongated body can, but need not necessarily, extend all the way through the aperture of the nanopore. For example, in embodiments such as described above with reference to FIGS. 1A-1D, the elongated body of the tether optionally can be sufficiently long that the tail region of the tether is disposed on the other side of a constriction (if present) of the nanopore than is the head region of the tether, and optionally can be disposed beyond the other side of the nanopore as is the head region of the tether. Illustratively, the elongated body of the tether can be disposed within the aperture of the nanopore by applying a suitable directional force to the elongated body of the tether. For example, a voltage can be applied across the nanopore in a manner such as described herein with reference to FIGS. 2A-2C, and the elongated body of the tether can include at least one charged moiety that, based on the voltage, attracts the tail region of the tether towards the side of the nanopore opposite that to which the head region of the tether is attached or at which the head region of the tether is attached to a first member, and causes translocation of the tail region so as to dispose all or a portion of the elongated body of the tether within the aperture of the nanopore.

Additionally, step 304 optionally can include disposing the polymerase adjacent to the first side of the nanopore. For example, the polymerase can be attached to or adjacent to the first side of the nanopore using a chemical bond, e.g., a covalent bond, hydrogen bond, ionic bond, dipole-dipole bond, London dispersion forces, or any suitable combination thereof. Or, for example, the polymerase can be attached to the first side of the nanopore using an interaction between a first protein structure on the polymerase and a second protein structure that is attached to, or adjacent to, the first of the nanopore. For example, the first and second structures can include alpha helices that interlock with one another. The attachment of the polymerase adjacent to the first side of the nanopore can be permanent, such that the polymerase is held in a generally fixed position with respect to the first side of the nanopore.

In one illustrative embodiment, the reduced thiol (—SH) group (also called a sulfhydryl group) of a cysteine residue of the polymerase or of the nanopore can be reacted with a thiol-reactive group of the other of the polymerase or of the nanopore. Examples of such groups include maleimide and iodoacetamide. As described in greater detail at www.lifetechnologies.com/us/en/home/references/molecular-probes-the-handbook/thiol-reactive-probes/introduction-to-thiol-modification-and-detection.html#head2, primary thiol-reactive reagents, including iodoacetamides, maleimides, benzylic halides, and bromomethylketones can react by S-alkylation of thiols so as to generate stable thioether products; arylating reagents such as 7-nitrobenz-2,1,3-oxadiazole (NBD) halides can react with thiols or amines by a similar substitution of the aromatic halide by the nucleophile; and because the thiolate anion is a better nucleophile than the neutral thiol, cysteine is more reactive above its pKa. Additionally, as described in greater detail at www.piercenet.com/method/sulfhydryl-reactive-cross-linker-chemistry, sulfhydryl-reactive chemical groups include haloacetyls, maleimides, aziridines, acryloyls, arylating agents, vinylsulfones, pyridyl disulfides, TNB-thiols (2-nitro-5-thiobenzoic acid), and disulfide reducing agents; such groups can conjugate to sulfhydryls via alkylation (e.g., via formation of a thioether bond) or disulfide exchange (e.g., formation of a disulfide bond). Sulfhydryl exchange reactions also suitably can be used. Alternatively, amines (—NH$_2$) can be targeted. For example, the primary amine of the lysine residue and the polypeptide N-terminus are relatively reactive. Amine residues can be targeted with N-hydroxysuccinimide esters (NHS esters), which can form a stable amide bond, or imidoester crosslinkers, which can react with primary amines to form amidine bonds. There are many other amine-reactive compounds. For example, as described at www.piercenet.com/method/amine-reactive-crosslinker-chemistry, synthetic chemical groups that can form chemical bonds with primary amines include isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters; such groups can conjugate to amines, for example, via acylation or alkylation. In still other embodiments, a modified amino acid residue can be used to introduce a novel functionality like an azide or alkyne to be used with click chemistry. For example, thiol or amine reactivities such as described above can be used with linkers that permit the addition of azide or alkyne functionalities to further be used in a click chemistry reaction.

Step 304 illustrated in FIG. 3 optionally further can include attaching the tail region of the tether to the other of the first side or second side of the nanopore or to a second member. Any suitable attachment such as provided herein, or otherwise known in the art, suitably can be used. For example, step 304 optionally can include attaching the tail region of the tether to the second side of the nanopore. Or, for example, step 304 optionally can include attaching the tail region of the tether to a second member (such as an oligonucleotide) disposed on the side of the nanopore opposite to that of the head region. In this regard, note that polymerase 130 need not necessarily be anchored to the first side of the nanopore in order for the polymerase 130 to remain bound to the nanopore. For example, under some conditions, the application of a directional force to the elongated body of a tether can cause translocation of the tail region so as to dispose all of the tether within the aperture of the nanopore. A sufficiently large force can cause the polymerase that is attached to the tether to become temporarily lodged in or on the nanopore. Although not intending to be a limiting with respect to physical configuration, the result can be termed 'corking' of the nanopore by the polymerase. Corking can be inhibited or avoided by limiting the force on the tether (e.g., applying less than 180 mV across the nanopore), limiting the duration of time that force is applied on the system, or using a sufficiently large protein that the corking interaction is avoided. Alternatively or additionally, a reverse voltage can be applied to the system to reverse the interaction between the protein and nanopore (referred to as 'uncorking'). Another option to inhibit or avoid corking or to facilitate uncorking is to remove charged amino acids from the nanopore opening or complementary charges on the surface of the protein, so as to reduce charge affinity between the two components. It can be further beneficial to add cross links to the structure of the protein (e.g., engineered cysteine pairs that for disulfide crosslinks or chemical crosslinkers), in order to stabilize the globular structure of the protein.

Corking can be observed based on a characteristic current or flux pattern that is distinct from patterns resulting from other configurations of the nanopore system. The distinct pattern can be observed for example, when applying a positive or negative bias to the nanopore system. Accordingly, current or flux patterns can be detected during assembly or use of a system that includes a protein that is localized to a nanopore via tether that is attached to the protein and disposed in the nanopore lumen. Detection of the patterns can be used to monitor assembly (e.g., to avoid corking), guide uncorking, or otherwise optimize desired assembly.

Note that because the head region of the tether is attached to the polymerase, such a directional force also can bring the polymerase adjacent to, or fully or partially disposed within, the aperture of the nanopore in a manner such as described herein with reference to FIGS. 1A-1D. For example, the attraction of the tail region towards the side of the nanopore opposite that at which the head region of the tether is attached to a first member also can cause translocation of the first member to a position adjacent to, or fully or partially disposed within, the aperture of the nanopore. While the polymerase is in such a position, the tail region 112 of tether 110 can be anchored to another member, e.g., can be hybridized to an oligonucleotide that is complementary to an oligonucleotide on the tail region 112 of the tether, and such anchoring of the tail region 112 can inhibit dissociation of the polymerase from the nanopore 100.

Method 300 illustrated in FIG. 3 also includes determining that a first nucleotide is being acted upon by the polymerase based on binding of the elongated tag to a first moiety disposed on the elongated body (step 305). For example, as described above with reference to FIGS. 1A-1D and 2A-2B, binding between first moiety 115 of the elongated body and the second moiety 122 of the elongated tag can define a duplex that generates a first signal state, e.g., a first electrical or optical signal state, that is detectable by suitable measurement circuitry, e.g., measurement circuitry 230 illustrated in FIG. 2A or measurement circuitry 240 illustrated in FIG. 2B. Different nucleotides can include different moieties 122 than one another, which moieties can generate different signals than one another, thus facilitating identification of the particular nucleotide being acted upon by polymerase 130 based upon the resulting signal.

Method 300 illustrated in FIG. 3 also includes, with the one or more reporter regions disposed along the elongated body, indicating when the first nucleotide is complementary or is not complementary to the next nucleotide in the sequence of the second polynucleotide (step 306). For example, as described above with reference to FIGS. 1A-1D and 2A-2C, reporter region(s) can be configured to generate a signal state responsive to the first nucleotide being complementary to a next nucleotide in the second polynucleotide, e.g., based upon a conformational change of the polymerase, release of pyrophosphate or other suitable phosphorous oxyanion, release of the elongated tag of the nucleotide, or the like.

For example, the polymerase can transition between what is referred to as an "open state," in which the polymerase does not bind a nucleotide, to a "closed state," in which the polymerase binds a nucleotide. See, e.g., Xia et al., "Alteration in the cavity size adjacent to the active site of RB69 DNA polymerase changes its conformational dynamics," Nucl. Acids Res. (2013), nar.gkt674, the entire contents of which are incorporated by reference herein. See also Santoso et al., "Conformational transitions in DNA polymerase I revealed by single-molecule FRET," Proc. Natl. Acad. Sci. USA, 107(2): 715-720 (2010), the entire contents of which are incorporated herein by reference.

Figure 7A:
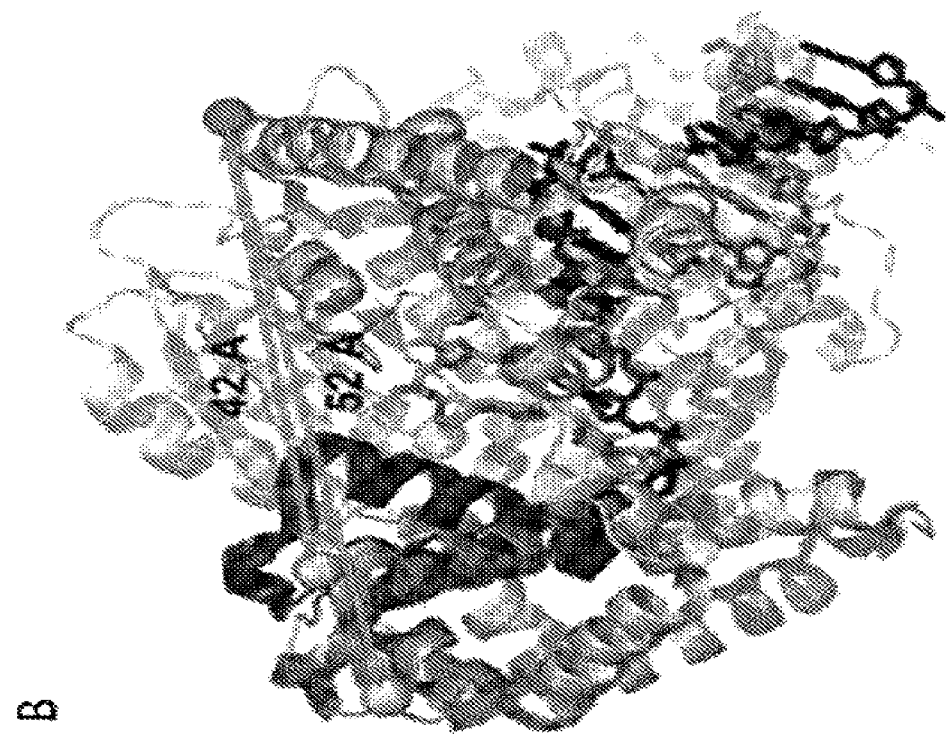
FIGS. 7A-7B schematically illustrate exemplary conformational changes of a polymerase.
Figure 7B:
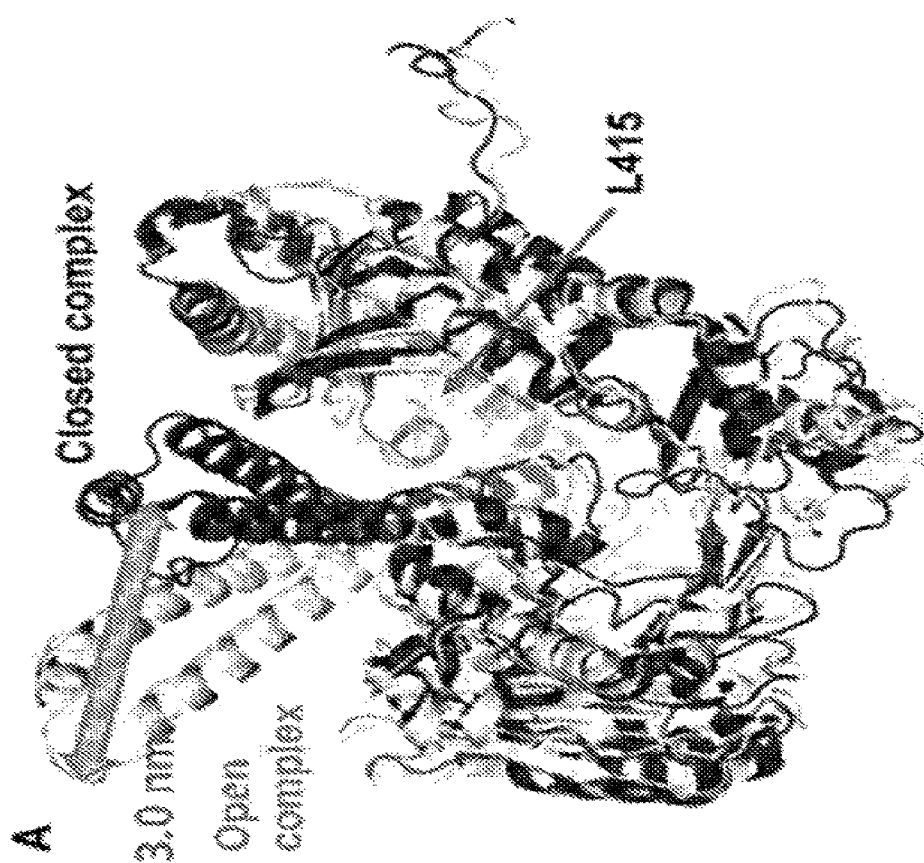

Conformational changes on the order of several nanometers are known to occur during the catalytic cycle of nucleotide incorporation as the polymerase transitions from the open to closed state, or as the polymerase switches into editing mode. For example, FIGS. 7A-7B schematically illustrate relatively large polymerase conformation changes (>1 nm) in two different polymerases. FIG. 7A illustrates RB69 polymerase, which exhibits a relatively large conformational change that results in relative movement between the thumb domain and finger domain, undergoing over 3 nm of movement between the open and closed conformations, as described by Xia et al. FIG. 7B illustrates Pol I (Klenow Fragment, or KF), which undergoes conformational changes during nucleotide incorporation as disclosed by Santoso et al. The α-carbon backbone of the polymerase is shown in beige. The DNA template strand is in dark gray, the primer strand in light gray. The terminal base pair at the active site is magenta. According to Santoso, the β carbons of the two side chains were used as fluorophore attachment sites, shown as green and red spheres, to measure conformational changes of the polymerase. The arrows indicate the distance in Angstroms between the green and red Cβ positions in the open and closed conformations. There also is evidence that the conformational changes of a polymerase can be dependent upon the identity of the nucleotide being incorporated, e.g., such as described in Olsen et al., "Electronic Measurements of Single-Molecule Processing by DNA Polymerase I (Klenow Fragment)," JACS 135: 7855-7860 (2013), the entire contents of which are incorporated by reference herein. In the nanopore embodiments of the present disclosure, the finger domain can be anchored to a nanopore while a tether is attached to the thumb domain. Alternatively, the thumb domain can be anchored to a nanopore while a tether is attached to the finger domain. In either construct, the relative movement that occurs between the finger and thumb domains during polymerase activity can be detected as relative movement between the tether and the nanopore. Attachment chemistries used to attach optical probes (e.g., FRET pairs) in the references cited herein can be used in the nanopore embodiments set forth herein. Other attachment points can be used in a polymerase-nanopore construct so long as conformational changes in the polymerase are reliably transmitted as relative movement between the tether and nanopore.

Figure 7C:
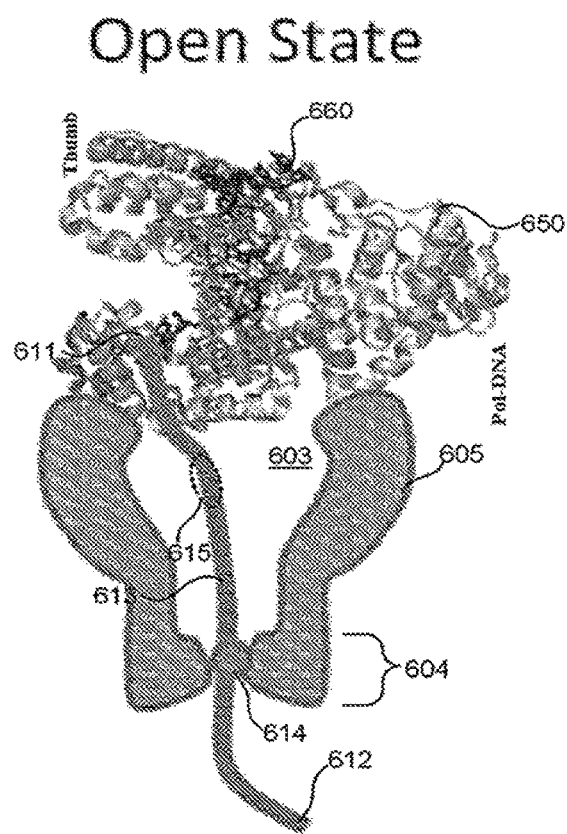
FIGS. 7C-7D schematically illustrate a composition including a tether anchored to a polymerase adjacent to a nanopore and configured for use sequencing a polynucleotide, according to some embodiments of the present invention.
Figure 7D:
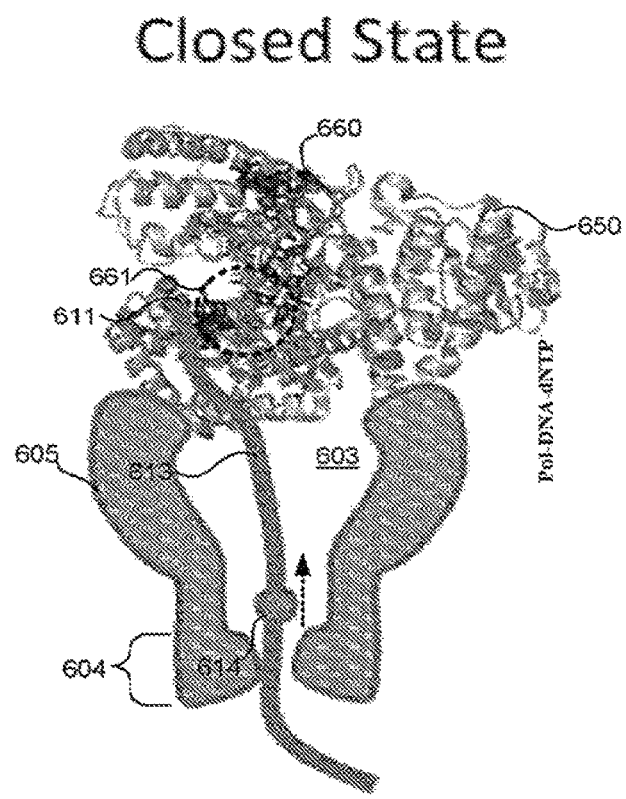

FIGS. 7C-7D schematically illustrate an exemplary composition including a permanent tether anchored to a polymerase disposed adjacent to a nanopore and configured for use in detecting a conformational change of the polymerase responsive to action of the polymerase upon a nucleotide. The nanopore includes biological pore 605, which can be disposed in a barrier (not specifically illustrated), e.g., a membrane of biological origin such as a lipid bilayer, or a solid state membrane. Biological pore 605 includes aperture 603 and constriction 604. The permanent tether includes head region 611, elongated body 613, and one or more reporter region(s) 614. Polymerase 650 is disposed adjacent to biological pore 605, and optionally can be attached to biological pore 605. Polymerase 650 is configured to receive a template polynucleotide, e.g., circular or linear ssDNA to be sequenced, to synthesize a polynucleotide having a complementary sequence to that of the ssDNA by sequentially receiving, binding, and adding nucleotides to the polynucleotide in accordance with the sequence of the ssDNA. Head region 611 of the permanent tether can be anchored to a location of polymerase 650 that undergoes a conformational change, e.g., responsive to receiving a nucleotide, binding a nucleotide, or adding a nucleotide to polynucleotide 660, and that moves reporter region(s) 614 to a sufficiently different location relative to constriction 604 so as to produce a signal that indicates when the nucleotide being acted upon is complementary or is not complementary to a next nucleotide in the sequence of the ssDNA. For example, head region 611 can be attached to a finger region of the polymerase, or a thumb of the polymerase. Exemplary attachment points in the finger and thumb regions of polymerases and chemistries for attaching moieties to these points are set forth in US Pat. App. Pub. No. 2011/0312529 A1, which is incorporated herein by reference.

For further details on the structure and function of family A and B polymerases, see Patel et al., "Getting a grip on how DNA polymerases function," Nature Structural Biology 8: 656-659 (2001), the entire contents of which are incorporated by reference herein. For further details on the structure and function of polymerases such as Pol I, see the following references, the entire contents of each of which are incorporated by reference herein: Olsen et al., "Electronic measurements of Single-Molecule Processing by DNA Polymerase I (Klenow Fragment)," JACS 135: 7855-7860 (2013); Torella et al., "Identifying molecular dynamics in single-molecule FRET experiments with burst variance analysis," Biophysics J. 100: 1568-1577 (2011); Santoso et al., "Conformational transitions in DNA polymerase I revealed by single-molecule FRET," Proc. Natl. Acad. Sci. USA, 107(2): 715-720 (2010), Markiewicz et al., "Single-molecule microscopy reveals new insights into nucleotide selection by DNA polymerase I," Nucleic Acids Res. 40: 7975-7984 (2012); Gill et al., "DNA Polymerase activity at the single-molecule level," Biochem. Soc. Trans. 39: 595-599 (2011), and Johnson et al., "Processive DNA synthesis observed in a polymerase crystal suggests a mechanism for the prevention of frameshift mutations," Proc. Natl. Acad. Sci. USA 100: 3895-3900 (2003). Any two residues or domains that are known from the above references (or other references cited herein) to undergo a change in relative position during polymerase activity can serve as attachment points to a nanopore and tether respectively in an embodiment of the present disclosure.

Figure 2B:
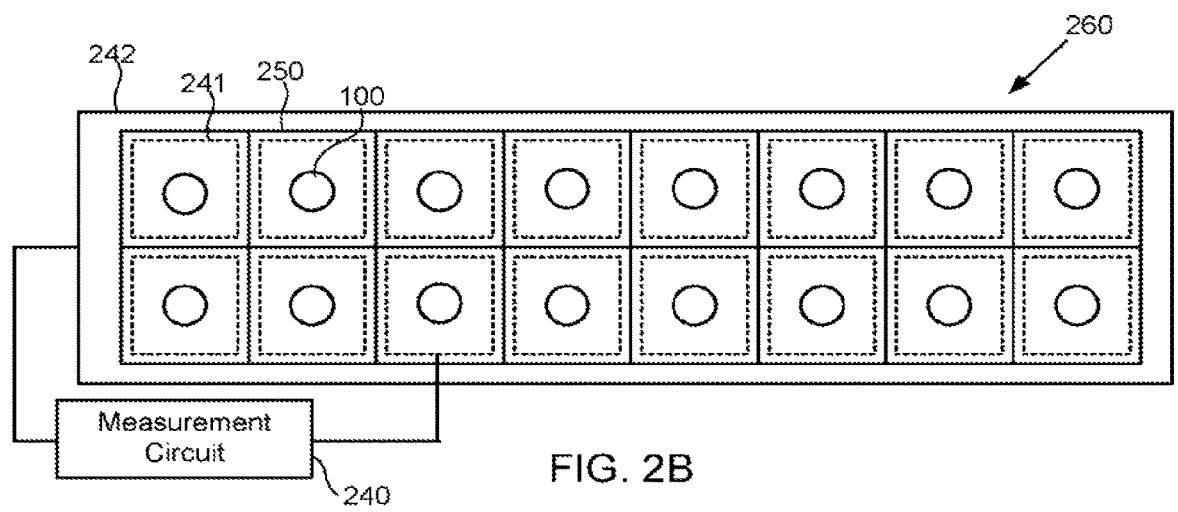
FIG. 2B schematically illustrates a plan view of a system including measurement circuitry configured to measure movement of respective reporter regions within the respective apertures of an array of nanopores, according to some embodiments of the present invention.

In one example, a voltage can be applied across the nanopore 605, e.g., using measurement circuit 230 and electrodes 231, 232 such as described further above with reference to FIG. 2A, or measurement circuit 240 and electrodes 241, 242 such as described further above with reference to FIG. 2B. Reporter region 614 or elongated body 613 includes an electrostatic charge that, responsive to the applied voltage, causes elongated body 613 to extend through constriction 604 such that reporter region(s) 614 are disposed within or adjacent to constriction 604 when first moiety 615 of elongated body 613 is not bound to a second moiety of an elongated tag of the nucleotide being acted upon. Optionally, the applied voltage can cause elongated body 613 to become taut when first moiety 615 of elongated body 613 is not bound to a second moiety of an elongated tag of the nucleotide being acted upon. As noted elsewhere herein, when first moiety 615 of elongated body 613 is bound to a second moiety of an elongated tag of the nucleotide being acted upon, the resulting duplex can become lodged in or adjacent to the constriction of the nanopore under a voltage applied across the nanopore, resulting in a first signal state based upon which the nucleotide can be identifiable. As illustrated in FIG. 7D, as the protein domains of polymerase 605 move, e.g., change conformation relative to that shown in FIG. 7D, such movements can impose a force on head region 611, which imposes a force on elongated body 613, which imposes a force on reporter region(s) 614, resulting in translational movement of reporter region(s) 614 within aperture 603, e.g., movement relative to constriction 604. As a result, a conformational change of polymerase 650 can be translated or transduced into a measurable change in current or flux through aperture 603, which also can be referred to as a blockade current or flux. It can be detectable based on such a second signal state whether the nucleotide being acted upon is complementary or is not complementary to the next nucleotide of the ssDNA.

In one illustrative embodiment, reporter region(s) 614 are constructed using modified nucleotides. For example, abasic nucleotides typically generate a 70 pA blockade current compared to residues that include bases, such as dT residues that generate only a 20 pA blockade current under conditions that include 10 mM 4-(2-hydroxyethyl)-1-piperazineethane-sulfonic acid) (HEPES) buffer, pH 8.0, 300 mM KCl, 1 mM MgCl$_2$, 1 mM DL-dithiothreitol (DTT), MspA M2 mutant pore (D90N, D91N, D93N, D118R, D134R & E139K), 180 mV across a 1,2-diphytanoyl-sn-glycero-3-phosphocholine (DPhPC) bilayer.

Movements of abasic residues on the order, e.g., of just a few Angstroms, can cause easily detectable changes in current or flux, e.g., of from one to tens of pAs. Because some polymerases move on the order of nanometers, and a single base in the tether corresponds to about 0.5 nanometers, it is anticipated that tether movements resulting from conformational changes in the polymerase to which the tether is anchored can be generated and readily transduced into currents or fluxes. Because the particular conformation of the polymerase can be based upon whether the nucleotide that the polymerase is acting upon is complementary or is not complementary to a next nucleotide in the ssDNA, it can be determined based upon a signal state (current or flux state) when that nucleotide is complementary or is not complementary to a next nucleotide in the ssDNA. Additionally, because the identity of the nucleotide influences both the magnitude of the conformational change as well as the time spent in the closed state, the signal state (current or flux state) also potentially can individually identify nucleotides as they are incorporated, so as to confirm the identification of the nucleotide of step 305 based upon the first signal state. For example, in some embodiments such as illustrated in FIG. 5B, the identity of the nucleotide can be revealed by the location of reporter 514 hybridizing with moiety 522. A corresponding signal is shown in FIG. 6, part "B." If there is a perfect match as in FIG. 5C, the polymerase can adopt a specific conformation. A corresponding signal is depicted in FIG. 6, part "D." The signals in FIG. 6, parts "C" and "D" are distinct and can uniquely signify a match or mismatch, respectively.

The magnitude or time duration, or both, of the polymerase's conformational change(s) can be based on the particular nucleotide that the polymerase is acting upon. Table 1 lists exemplary single molecule kinetic parameters that were measured for Klenow fragment processing of templates using current changes in a SWNT attached to a single polymerase and reported by Olsen et al. In Table 1, $\tau_{lo}$ corresponds to the duration of time spent in the polymerase's closed conformation, $r_{lo}$ corresponds to the mean-normalized variance for $\tau_{lo}$, $\tau_{hi}$ corresponds to the duration of time spent in the polymerase's open conformation, $r_{hi}$ corresponds to the mean-normalized variance for $\tau_{hi}$, and the rate corresponds to the rate of processing, e.g., how quickly the polymerase adds the nucleotide to the template. Olson et al., reports that the average magnitude H is a proxy for the extent of mechanical closure by the enzyme. For the present systems, methods, and compositions, the value H can be considered to be the extent of conformational change between two reference points on the polymerase, as measured in units of distance. For example, H can correspond to the magnitude of mechanical closure to be affected by nucleotide match or mismatch.

TABLE 1

| template | nudeotide | $\tau_{lo}$ (ms) | $r_{lo}$ | $\tau_{hi}$ (ms) | $r_{hi}$ | H (nA) | rate (1/s) |
|---|---|---|---|---|---|---|---|
| poly(dT)$_{42}$ | dATP | 0.33 ± 0.08 | 0.85 ± 0.09 | 71.4 ± 1.4 | 0.95 ± 0.08 | 6.94 | 14.4 ± 2.9 |
| poly(dA)$_{42}$ | dTTP | 0.42 ± 0.09 | 0.83 ± 0.06 | 63.7 ± 1.1 | 0.96 ± 0.06 | 4.90 | 16.0 ± 2.9 |
| poly(dG)$_{42}$ | dCTP | 0.32 ± 0.07 | 0.78 ± 0.05 | 39.0 ± 5.6 | 0.98 ± 0.06 | 2.53 | 26.2 ± 4.4 |
| poly(dC)$_{42}$ | dGTP | 0.33 ± 0.05 | 0.78 ± 0.05 | 38.0 ± 5.8 | 1.03 ± 0.07 | 2.40 | 28.5 ± 3.5 |

$^a$Average values ± standard deviation.
dx.doi.org/10.1021/ja311603rl *J. Am. Chem. Soc.* 2013 135: 7855-7860

Using the compositions, methods, and systems provided herein, a signal that correlates to the time duration of the open state $\tau_{hi}$, the magnitude of conformational change H, and rate of processing together can be used to indicate when the first nucleotide is complementary or is not complementary to a next nucleotide of the ssDNA, and potentially signals can be differentiated according to a unique signature for each base. Incorporation rates can also be greatly changed by the selective use modified nucleotides, such as alpha- or gamma thiol nucleotides. See, for example, U.S. Patent Publication No. 2011/0312529 to He et al., the entire contents of which are incorporated by reference herein.

In one illustrative embodiment, the template DNA is circularized and polymerase 650 is a strand-displacing polymerase (such as Phi29). In this manner, the template can be sequenced multiple times in a rolling circle mode such as known in the art. Such an embodiment also can inhibit inadvertently pulling the template DNA into or through constriction 604, because only ssDNA can translocate. Any stray ssDNA that may find its way through constriction 604 (or if a linear template is used) is expected to transit rapidly and is expected to manifest as noise in the signal. Alternatively, one can employ one or more positively charged reporter region(s) 614 under reverse polarity such that only the reporter region(s) are drawn into the constriction 604, whereas negatively charged DNA will be repelled.

In some embodiments, polymerase 650 can be attached, e.g., anchored, to the mouth of biological pore 605. This could be accomplished using cysteine/thiol conjugation chemistry, for example. Such a conjugation can provide that polymerase 650 is anchored in a reproducible and stable orientation that can enhance the transfer of conformational motion of the polymerase 650 to translational motion of reporter region(s) 614. However, conjugation of the polymerase to the pore need not be required. For example, the force exerted by the tether responsive to the applied voltage can be sufficient to hold the polymerase in place, or another member (e.g., an oligonucleotide) can be bound to the tail end of the tether so as to inhibit dissociation of the polymerase from the nanopore.

Additionally, note that a rapid AC current can be used instead of a DC current in order to produce the requisite electric field. This has the advantage of inhibiting AgCl electrode depletion and lengthening the time the device can run.

Note that the duplex formed between the moiety of the elongated tag and the moiety of the tether can be in thermodynamic equilibrium. It should be appreciated that a duplex in thermodynamic equilibrium can have on and off rates that are based upon the length and character of the nucleic acid sequence, and that the duplex may dissociate from time-to-time. It can be useful for the mean time spent in the duplex state (the inverse of the off rate) to be shorter than the average lifetime of the polymerase-nucleotide complex during the incorporation event, so that after incorporation and tag release from the nucleotide, the tag will diffuse away and not block incoming nucleotide tags. The effective on rate can be sufficiently high to result in relatively fast re-binding as compared with the lifetime of the polymerase-nucleotide complex, so that incorporation events are detected and so that the duplex reforms after any dissociation events occurring during nucleotide incorporation. The on rate will be pseudo-first order in the concentration of the elongated tag of the nucleotide, which can be considered to make such an arrangement a stochastic sensor of the concentration of the elongated tag. Note that freely diffusing elongated tags can have a relatively low concentration (e.g., from 10 nM to 100 nM, or from 100 nM to 250 nM, or from 250 nM to 500 nM, or from 500 nM to 1 uM), whereas the elongated tag of the nucleotide being acted upon will effectively have a relatively high concentration because it is bound to the nucleotide which is held in place by the polymerase during incorporation, and thus is not free to diffuse away.

In certain exemplary embodiments described herein, the elongated body of the tether and the elongated tag of the nucleotide being acted upon by the polymerase respectively can include, or can even consist solely of, single-stranded DNA (ssDNA). However, it should be appreciated that other types of molecules suitably can be used. For example, any tether suitably can be used that includes an elongated body having one or more of the following features, and optionally includes all of the following features:

1. The elongated body can include a region that interacts with moieties respectively attached to different types of nucleotides in a manner that the moieties are distinguishable from one another, e.g., via measurement of current or flux through the pore constriction.
2. The elongated body can include a charged region that causes it to be pulled through the constriction of the pore responsive to an applied voltage. The elongated body can be held taut in such a configuration. This charged region can be located adjacent to the pore constriction to result in a net force.
3. The elongated body can include one or more reporter regions that yield a clearly distinguishable signal state when the nucleotide upon which the polymerase is acting is complementary or is not complementary to a next nucleotide in the sequence of the polynucleotide being sequenced. The reporter region(s) and the charged region can be the same as one another; that is, a single region can be both a reporter region and a charged region. Additionally, it should be understood that different signal states, which can represent identities of nucleotides or whether such nucleotides are a match or a mismatch, need not necessarily occur at different times than one another, and indeed can occur at the same time as one other. For example, a measured signal (e.g., optical or electrical) can include a composite of more than one signal state (e.g., two signal states), each of which signal states provides information about one or more of an identity of a nucleotides or whether such nucleotide is a match or a mismatch.

An exemplary material that can be included in the elongated body of the tether, or the elongated tag of the nucleotide being acted upon, or both, is a polymer. Polymers include biological polymers and synthetic polymers. Exemplary biological polymers that are suitable for use in the elongated body of the tether, or the elongated tag of the nucleotide being acted upon, or both, include polynucleotides, polypeptides, polysaccharides, polynucleotide analogs, and polypeptide analogs. Exemplary polynucleotides and polynucleotide analogs suitable for use in the elongated body of the tether, or the elongated tag of the nucleotide being acted upon, or both, include DNA, enantiomeric DNA, RNA, PNA (peptide-nucleic acid), morpholinos, and LNA (locked nucleic acid). Exemplary synthetic polypeptides can include charged amino acids as well as hydrophilic and neutral residues. In some embodiments, the tether is not a nucleic acid or does not include nucleotides. For example, a tether can exclude naturally occurring nucleotides, non-naturally occurring nucleotide analogs or both. One or more of the nucleotides set forth herein or otherwise known in the art can be excluded from a tether.

Other exemplary polymers that can be suitable for use in the elongated body of the tether, or the elongated tag of the nucleotide being acted upon, or both, include synthetic polymers such as PEG (polyethylene glycol), PPG (polypropylene glycol), PVA (polyvinyl alcohol), PE (polyethylene), LDPE (low density polyethylene), HDPE (high density polyethylene), polypropylene, PVC (polyvinyl chloride), PS (polystyrene), NYLON (aliphatic polyamides), TEFLON® (tetrafluoroethylene), thermoplastic polyurethanes, polyaldehydes, polyolefins, poly(ethylene oxides), poly(ω-alkenoic acid esters), poly(alkyl methacrylates), and other polymeric chemical and biological linkers such as described in Hermanson, mentioned further above. Additionally, as noted above, the moieties of the elongated body of the tether, or the elongated tag of the nucleotide being acted upon, or both, can be individual short nucleotide sequences that interact with one another. These moieties can be non-interacting with polymerase such as RNA, PNA or LNA labels, morpholinos, or enantiomeric DNA, for example. The moiety need not be formed of the same polymer as other portions of the elongated body of the tether or the elongated tag of the nucleotide being acted upon. Elongated tags can be readily attached to the gamma phosphate of nucleotides, as is well known in the art. Additionally, in one illustrative embodiment, that isoG and isoC bases can be used on the nucleotide elongated tags, or on the tether, or both, so as to inhibit hybridization of the elongated tags or tether with the DNA being sequenced. Additionally, other schemes can be used to induce secondary structure in the tether to shorten it, such as a hairpin.

Additionally, note that the tether can include multiple moieties, each of which respectively interacts with a moiety attached to a given type of nucleotide. The interaction between the moiety of the nucleotide with the corresponding moiety of the tether can move the reporter region(s) of the tether by a corresponding amount that facilitates identification of the corresponding nucleotide via a signal, e.g., via a current or flux through the aperture of the pore.

In one non-limiting, illustrative embodiment, the pore includes MspA, which can provide a satisfactory separation of nucleotide-specific currents or fluxes, e.g., a 3.5-fold greater separation of nucleotide-specific currents or fluxes as compared to alpha-hemolysin. However, it should be appreciated that alpha-hemolysin or other types of pores suitably can be used with the present compositions, systems, and methods.

Additionally, note that in embodiments in which a voltage is applied across the pore and movements of the reporter region(s) are measured via current or flux through the pore, the voltage can suitably be applied using either direct current (DC) or alternating current (AC). AC current can help to extend electrode life, help to eject cleaved elongated tags from the pore if the tags become stuck. Additionally, note that a positively charged tether can be used with a reverse bias on the pore so as to inhibit the DNA being sequenced from being drawn into the pore. Additionally, note that a positively charged tether and positively charged elongated tags can be used with a reverse bias on the pore so as to inhibit the DNA being sequenced from being drawn into the pore.

Additionally, a stochastic sensing method can be employed. In this arrangement, an AC current can be used to move the hybridized duplex adjacent to the constriction. For example, FIGS. 4A-4E schematically illustrate a composition including a tether anchored to or adjacent to a nanopore and configured for use in detecting action of a polymerase upon a nucleotide using a tether anchored to or adjacent to a nanopore responsive to a change in electrical potential across the nanopore, and FIG. 4F illustrates an exemplary signal that can be generated during use of such a composition.

The composition illustrated in FIG. 4A includes nanopore 400 including a first side, a second side, an aperture extending through the first and second sides, and a constriction disposed between the first and second sides (components of nanopore 400 not specifically labeled, but can be analogous to those illustrated in FIGS. 7C-7D); permanent tether 410 including a head region anchored to the first side of nanopore 400, a tail region that optionally is coupled to another member 460 (e.g., an oligonucleotide) that inhibits dissociation of polymerase 430 from nanopore 400, and an elongated body that includes one or more reporter regions 414 and first moiety 415 (other components of tether 410 not specifically labeled, but can be analogous to those illustrated in FIGS. 7C-7D); and polymerase 430. As illustrated in FIG. 4A, when polymerase 430 is not acting upon a nucleotide, the polymerase can be in an open state. The signal illustrated in FIG. 4F depicted under FIG. 4A includes a current or flux state corresponding to reporter region(s) 414 being disposed in a location that is characteristic of the open state of polymerase 430, under a positive voltage applied across nanopore 400, e.g., +180 mV, where +180 mV indicates 0 mV on the first side of the nanopore and +180 mV on the second side of the nanopore.

The composition illustrated in FIG. 4B further includes nucleotide 420 including elongated tag 421 that includes second moiety 422. Polymerase 430 acts upon nucleotide 420, causing polymerase 430 to change conformation to a closed state such as illustrated in FIG. 4B. The signal illustrated in FIG. 4F depicted under FIG. 4B includes a current or flux state corresponding to reporter region(s) 414 being disposed in a location that is characteristic of the closed state of polymerase 430, under a positive voltage applied across nanopore 400, e.g., +180 mV. Note that under such a positive voltage, first moiety 415 may be disposed on the opposite side of nanopore 400 from moiety 422 of nucleotide 420, thus inhibiting formation of a duplex between moiety 415 and moiety 422 under the positive voltage. Note that moiety 415 can be located at any suitable position along the elongated tag of tether 410, e.g., can be located between the tail region and reporter region(s) 414 such as illustrated in FIG. 4A, or can be adjacent to the head region, adjacent to the tail region, adjacent to the reporter region, or between the head region and reporter region(s) 414.

As illustrated in FIG. 4C, an interaction between moiety 422 of nucleotide 420 and moiety 415 of tether 410 can define duplex 423 under a reverse voltage, e.g., under a negative voltage based upon which moieties 415 and 422 are disposed on the same side of nanopore 400 as one another. The signal illustrated in FIG. 4F depicted under FIG. 4C includes a current or flux state corresponding to the positions of reporter region(s) 414 and duplex 423 under the negative voltage applied across nanopore 400, e.g., −180 mV, where −180 mV indicates 0 mV on the first side of the nanopore and −180 mV on the second side of the nanopore. The position of reporter region 414 can be made sensitive, depending on where the tether is attached to the polymerase, to distinguishing between match and mismatch nucleotides in a manner analogous to that described in the Freudenthal references noted above.

Such as illustrated in FIG. 4D, upon reversing the voltage to a positive voltage, e.g., +180 mV, duplex 423 can become lodged in or adjacent to the constriction of the nanopore. The signal illustrated in FIG. 4F depicted under FIG. 4D includes a current or flux state corresponding to the position of duplex 423, as well as the particular moieties defining duplex 423, under the positive voltage applied across nanopore 400, e.g., +180 mV. Based upon moiety 422 being selected so as to correspond a single type of nucleotide, the signal can be used to determine which nucleotide is being acted upon by polymerase 430. Note that duplex 423 formed between moiety 415 and moiety 422 can be sufficiently large as to inhibit movement of the duplex through the constriction.

As illustrated in FIG. 4E, responsive to continued application of the positive voltage, e.g., +180 mV, duplex 423 can dissociate. Such dissociation can be considered to "interrupt" duplex 423 formed between moiety 415 and moiety 422. In some embodiments, moiety 415 can move through the constriction so as to be disposed on the second side of nanopore 400. The portion of FIG. 4F immediately below FIG. 4E illustrates an exemplary current or flux through the aperture under the positive voltage following dissociation of moiety 415 from moiety 422. The signal illustrated in FIG. 4F depicted under FIG. 4E includes a current or flux state corresponding to reporter region(s) 414 being disposed in a location that is characteristic of the closed state of polymerase 430, under a positive voltage applied across nanopore 400, e.g., +180 mV. Moiety 422 can be configured so as to remain disposed on the first side of nanopore 400 even if moiety 415 becomes disposed on the second side of nanopore 400, so as to temporarily inhibit interaction between moieties 415 and 422. As illustrated in FIG. 4C, following such dissociation, the voltage applied across aperture 403 can again be changed, e.g., can be changed back to the first voltage, responsive to which moieties 415 and 422 can interact with one another so as again to define duplex 423.

It should be appreciated that the signals corresponding to the relative positions of reporter region(s) 414 and duplex 423 and the particular moieties defining duplex 423 can be detectable in any suitable manner. For example, the composition can be in operable communication with a measurement circuit such as described above with reference to FIG. 2A or FIG. 2B. The measurement circuit can be configured to detect the current or flux through the aperture of nanopore 400, which can vary over time based upon the conformational state of polymerase 430 and based upon moiety 422 of the particular nucleotide 420 being acted upon by polymerase 430. In one illustrative embodiment, nanopore 400, tether 410, polymerase 430, and nucleotide 420 can be immersed in a conductive fluid, e.g., an aqueous salt solution. A measurement circuit configured analogously to measurement circuit 230 illustrated in FIG. 2A or measurement circuit 240 illustrated in FIG. 2B can be in communication with first and second electrodes and can be configured to apply a first voltage between those electrodes so as to apply a voltage across nanopore 400, as represented by the "+" and "−" signs illustrated in FIG. 4A, and to use the electrodes to measure the magnitude of a current or flux through aperture 403 at the first voltage. For example, the portion of FIG. 4F immediately below FIG. 4A illustrates an exemplary current or flux through the aperture of nanopore 400 at a first voltage. Reporter region 414 can have a different electrical or flux blockade property than some or all other regions of the elongated body of the tether (not specifically labeled). For example, reporter region(s) 414 can include an electrostatic charge, while some or all other regions of elongated body can include a different electrostatic charge, or can be uncharged (e.g., can be electrically neutral). Or, for example, reporter region(s) 414 can be uncharged, while some or all other regions of the elongated body can include an electrostatic charge. In one illustrative, non-limiting example, the elongated body of the tether includes a polynucleotide that includes one or more abasic nucleotides that define reporter region(s) 414. The magnitude of the current or flux through the aperture of nanopore 400 can measurably change responsive to the relative location of reporter region(s) 414 within aperture 403, the relative location of duplex 423, and the moieties defining duplex 423, based upon which the conformational state of polymerase 430 and the action of polymerase 430 can be determined.

Note that in some embodiments, the respective lengths of the elongated body of the tether and the linker bridging the nucleotide and the elongated tag, the respective locations of moieties 415 and 422, and the respective location of reporter region(s) 414 are co-selected so as to inhibit or preclude the application of force to nucleotide 420 while the nucleotide is being acted upon by polymerase 430, and thus to inhibit such a force from modifying the performance of the polymerase. In one illustrative embodiment, the interaction between moiety 415 and moiety 422 forms duplex 423. The length of the elongated body of the tether, and the location of moiety 415 along the elongated body, can be co-selected such that moiety 415 can be extended through the constriction of nanopore 400 responsive to an appropriate applied voltage, e.g., so as to cause dissociation between moiety 415 and moiety 422. The size of duplex 423 can inhibit movement of the duplex through the constriction of nanopore 400, and can shield nucleotide 420 from forces that otherwise may have been applied to nucleotide 420 via elongated tag 421. In one exemplary embodiment, reporter region(s) 414 are disposed at a suitable location along the elongated body of tether 410 so as to be disposed within, or adjacent to, the constriction of nanopore 400 when moieties 415 and 422 dissociate from one another under the positive voltage.

In another example, example, FIGS. 5A-5D schematically illustrate a composition including a tether anchored to or adjacent to a nanopore and configured for use in detecting action of a polymerase upon a nucleotide using a tether anchored to or adjacent to a nanopore responsive to a change in electrical potential across the nanopore, and FIG. 6 illustrates exemplary signals that can be generated during use of such a composition.

Figure 5A:
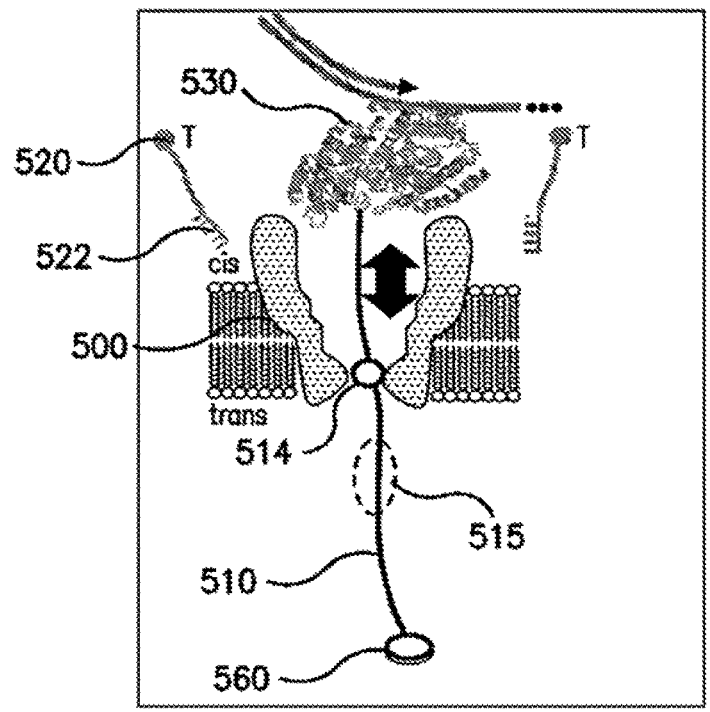
FIGS. 5A-5D schematically illustrate an exemplary use of a composition for sequencing a polynucleotide using a tether anchored to a polymerase adjacent to a nanopore, according to some embodiments of the present invention.
Figure 5B:
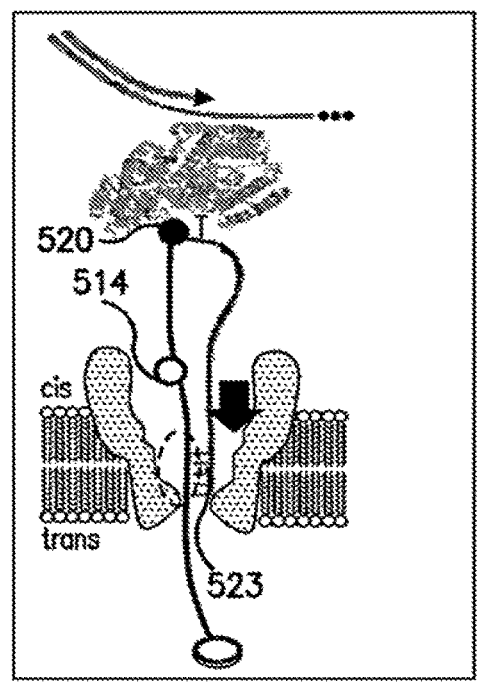

The composition illustrated in FIG. 5A includes nanopore 500 including a first side, a second side, an aperture extending through the first and second sides, and a constriction disposed between the first and second sides (components of nanopore 500 not specifically labeled, but can be analogous to those illustrated in FIGS. 7C-7D); permanent tether 510 including a head region anchored to the first side of nanopore 500, a tail region that optionally is coupled to another member 560 (e.g., an oligonucleotide) that inhibits dissociation of polymerase 530 from nanopore 500, and an elongated body that includes one or more reporter regions 514 and first moiety 515 (other components of tether 510 not specifically labeled, but can be analogous to those illustrated in FIGS. 7C-7D); nucleotide 520 including an elongated tag (not labeled) that includes second moiety 522; and polymerase 530. As illustrated in FIG. 5A, when polymerase 530 is not acting upon nucleotide 520, the polymerase can be in an open state or a closed state, each of which has a unique signal relating to their unbound states. The signal illustrated in FIG. 6 denoted "A" (long-dashes line) includes a current or flux state corresponding to reporter region(s) 514 being disposed in a location that is characteristic of the unbound states of polymerase 530, under a positive voltage applied across nanopore 500, e.g., +180 mV.

The composition illustrated in FIG. 5B includes polymerase 530 acting upon nucleotide 520, causing polymerase 530 to change conformation to a closed state. Additionally, an interaction between moiety 522 of nucleotide 520 and moiety 515 of tether 510 can define duplex 523. Under a positive voltage, e.g., +180 mV, duplex 523 can become lodged in or adjacent to the constriction of nanopore 500. The signal illustrated in FIG. 6 denoted "B" (solid line)

includes a current or flux state corresponding to the position of duplex 523, as well as the particular moieties defining duplex 523, under the positive voltage applied across nanopore 500, e.g., +180 mV. Based upon moiety 522 being selected so as to correspond a single type of nucleotide, the signal can be used to determine which nucleotide is being acted upon by polymerase 530. Note that duplex 523 formed between moiety 515 and moiety 522 can be sufficiently large as to inhibit movement of the duplex through the constriction. Illustratively, the "reporter" for each different nucleotide can include the bases immediately adjacent to the duplex (e.g., just below the last duplex base in FIG. 5B). Thus, in one non-limiting example, there can be four reporters to identify the nucleotides. There also can be a fifth reporter, which is reporter 514 that is shown as a circle. Reporter 514 can be used to report the conformational state of polymerase 530 as in FIGS. 5C and 5D. This conformational state can depend on whether the polymerase is holding a matched or mismatched nucleotide.

Figure 5C:
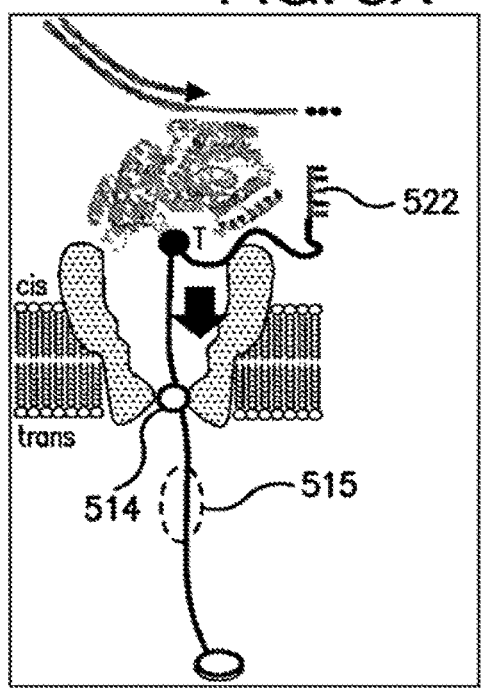
Figure 5D:
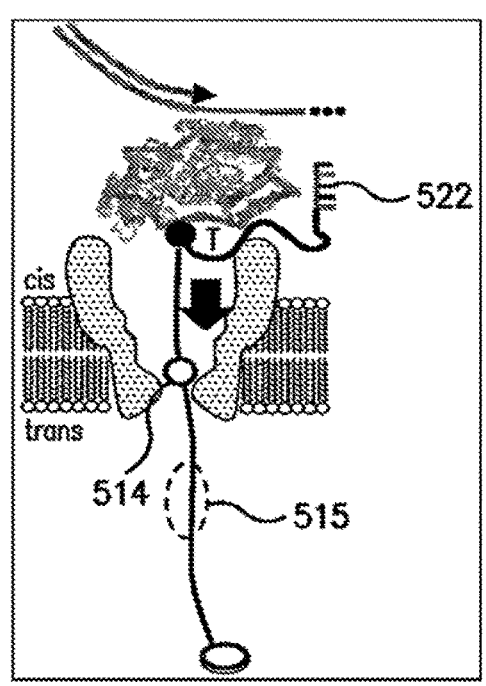
Figure 6:
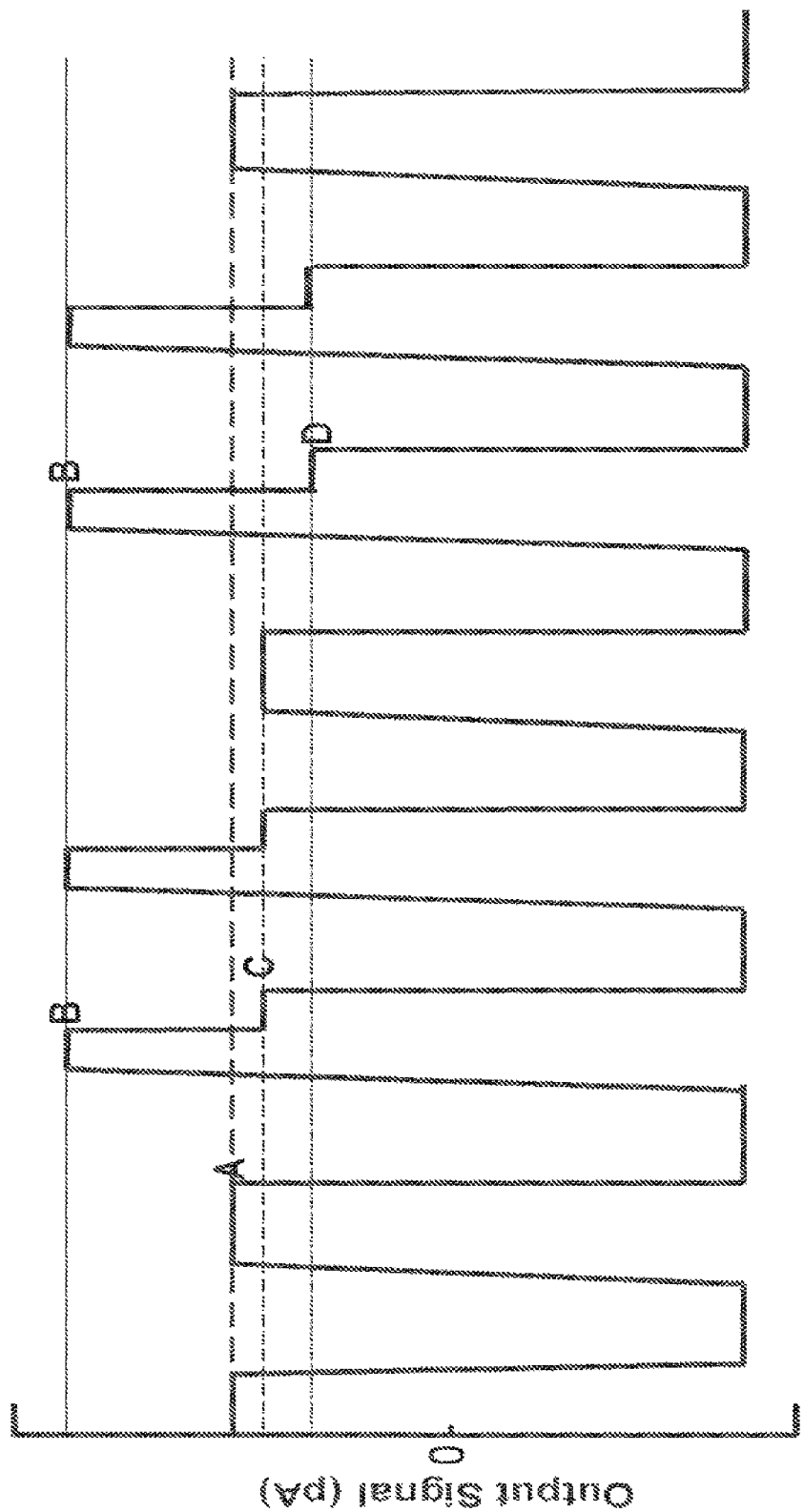
FIG. 6 schematically illustrates an exemplary signal that can be generated during use of the composition of FIGS. 5A-5D, according to some embodiments of the present invention.

For example, as illustrated in FIG. 5C, responsive to continued application of the positive voltage, e.g., +180 mV, duplex 523 can dissociate. Such dissociation can be considered to "interrupt" duplex 523 formed between moiety 515 and moiety 522. In some embodiments, moiety 515 can move through the constriction so as to be disposed on the second side of nanopore 500. The portion of FIG. 6 denoted "C" (short-dashes line) illustrates an exemplary current or flux through the aperture under the positive voltage following dissociation of moiety 515 from moiety 522. The current or flux state denoted "C" corresponds to reporter region(s) 514 being disposed in a location that is characteristic of the closed state of polymerase 530 in which the correct (match) nucleotide 520 is bound by the polymerase, under a positive voltage applied across nanopore 500, e.g., +180 mV.

In this example, polymerase 530 incorporates nucleotide 520 into the polynucleotide being sequenced, cleaves the tag of that nucleotide, and subsequently binds another nucleotide that may or may not be complementary to the next nucleotide in the polynucleotide being sequenced. For example, the "T" nucleotide illustrated in FIG. 5C happens to be complementary to the next nucleotide in the polynucleotide being sequenced, whereas the "T" nucleotide illustrated in FIG. 5D happens not to be complementary to the next nucleotide in the polynucleotide being sequenced. In the example illustrated in FIG. 5D, under application of the positive voltage, e.g., +180 mV, polymerase 530 may change to a unique conformation that occurs only when the nucleotide being acted upon is a mismatch to the next nucleotide in the polynucleotide being sequenced. This slightly repositions reporter region(s) 514 in the constriction of nanopore 500 relative to the position of reporter region(s) 514 for the case where the nucleotide was a match, e.g., as illustrated in FIG. 5C. The portion of FIG. 6 denoted "D" (dotted line) illustrates an exemplary current or flux through the aperture under the positive voltage polymerase 530 changing to the conformation corresponding to a mismatched nucleotide, under a positive voltage applied across nanopore 500, e.g., +180 mV. Note that the signal level of the dotted line at "D" is different than the signal level of the dashed line at "C," thus facilitating distinguishing match nucleotides from mismatch nucleotides. Additionally, each mismatched base also can have a unique polymerase confirmation, resulting in distinguishable signal states.

Note that the above states are not intended to be limiting, but are provided by way of example. Other detectable states than those shown can occur. For example, there can be multiple detectable states for the polymerase when it has no nucleotide corresponding to such configurations as open and closed, or even multiple states when there is a mismatched nucleotide associated with the polymerase in either the open or closed states.

It should be appreciated that the signals corresponding to the relative positions of reporter region(s) 514 and duplex 523 and the particular moieties defining duplex 523 can be detectable in any suitable manner such as provided elsewhere herein. Additionally, it should be appreciated that the signal indicating when the nucleotide being acted upon is complementary or is not complementary to a next nucleotide in the sequence of the polynucleotide being sequence, need not be electrical or optical, and indeed can be generated in any suitable manner.

Additionally, it should be noted that the dissociation of a duplex such as may be formed based on an interaction between a first moiety of an elongated body and a second moiety of an elongated tag responsive to an applied voltage can be characterized as defining a first pathway that is characterized by two or more kinetic constants. Additionally, the indication when the first nucleotide is complementary or is not complementary to a next nucleotide in the sequence of a polynucleotide being sequenced, e.g., a conformational change of the polymerase, release of pyrophosphate, or release of the elongated tag of the nucleotide, can be characterized as defining a second pathway that is characterized by two or more kinetic constants. The statistical distribution of signals measured (e.g., optically or electrically measured) during the course of obtaining measurements of the first pathway or the second pathway can be based on the relative values of the kinetic constants corresponding to that pathway. For example, based upon a given kinetic constant for the first pathway or the second pathway being significantly greater than the other kinetic constants for that pathway, the kinetics of that pathway can be dominated by that given kinetic constant, and the resulting statistical distribution of signals can be described by an exponential function. In comparison, two or more of the kinetic constants for the first pathway or for the second pathway can be selected so as to be of the same order of magnitude as one another, or even so as to be substantially the same as one another (e.g., to differ from one another by a factor of five or less, or four or less, or three or less, or two or less), such that the kinetics of that pathway are not dominated by either kinetic constant, and the resulting statistical distribution of signals can be described by a gamma function, in which there is substantially no probability of zero-time or very short events that are substantially non-observable. In comparison, with an exponential distribution, there is a high probability of short or zero-time events that are substantially non-observable.

Figure 12A:
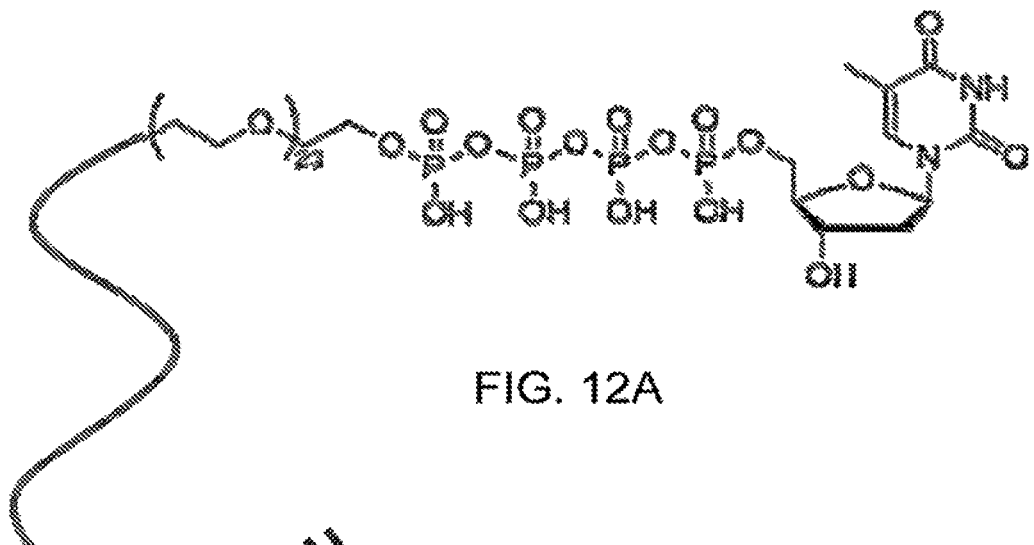
FIGS. 12A-12B illustrate exemplary structures for use in modifying a kinetic constant in a reaction scheme in which a nucleotide is being acted upon by a polymerase, according to some embodiments of the present invention.
Figure 12B:
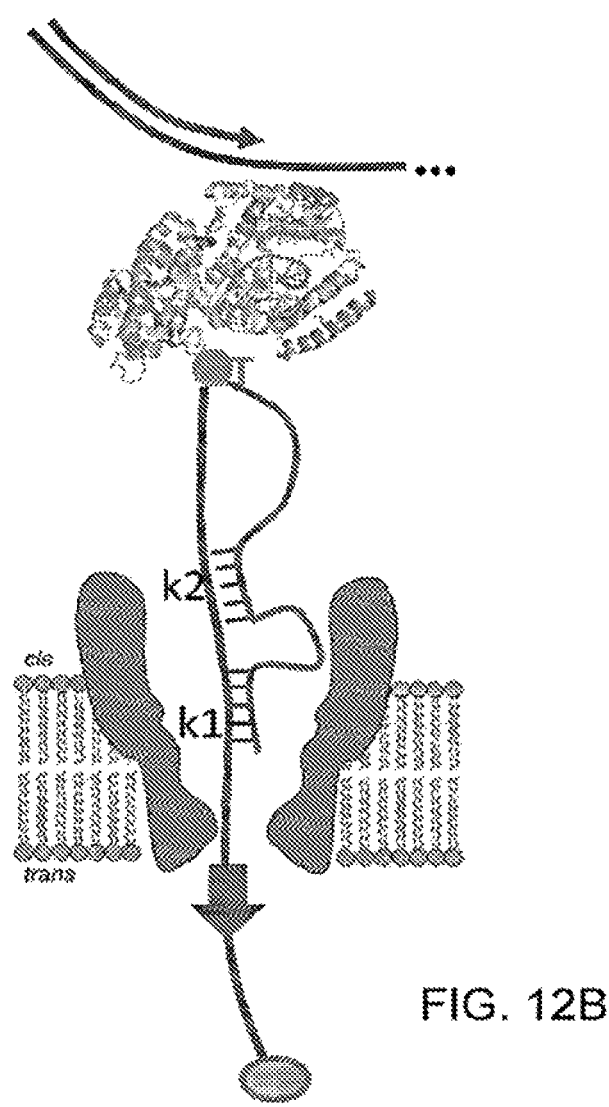

One or more of the kinetic constants of the first or second pathway can be modified in any suitable manner so as to be of the same order as one or more other of the kinetic constants of that pathway, or even so as to be substantially the same as one or more other of the kinetic constants of that pathway. For example, as noted above, the polymerase can be modified so as to delay release of pyrophosphate responsive to incorporation of a nucleotide into the first nucleotide, thus modifying at least one kinetic constant of that pathway. As another example, the tether further can include a second moiety that hybridizes with the first moiety so as to form a hairpin structure. The first and second moieties of the tether can be configured to dehybridize from one another in a two-step process responsive to a voltage applied across the nanopore, thus modifying at least one kinetic constant of that pathway. An exemplary tetraphosphate modified nucleotide with a label configured to form a hairpin structure is shown in FIG. 12A. Upon hybridization with the tether, a hairpin is formed as shown in FIG. 12B. This hairpin can be expected to have two stripping rate constants, k1 and k2, that are shown in FIG. 12B. These rate constants can be designed to be of a similar magnitude as one another, so that when added together, they can form a gamma distribution.

As noted elsewhere herein, a variety of compositions suitably can be included in the elongated tag of the nucleotide or the elongated body of the tether, or both. Such compositions can include DNA, PNA, LNA, RNA, morpholinos, PEG (polyethylene glycol), and the like, and can have any suitable length. An oligonucleotide label containing an appropriately modified nucleotide suitably can be linked to such different compositions, for example, using click chemistry compatible precursors are ideal. In one example, the nucleotide is azide-labeled, which would facilitate the use of alkyne-labeled oligonucleotides which are easily synthesized. Exemplary molecules include tetraphosphate-labeled nucleotides such as shown below, in which (A) corresponds to azide-$P_4O_{13}$-dTTP, and (B) corresponds to alkyne-$P_4O_{13}$-dTTP. These nucleotides can be modified with any desired tag by using standard click chemistry:

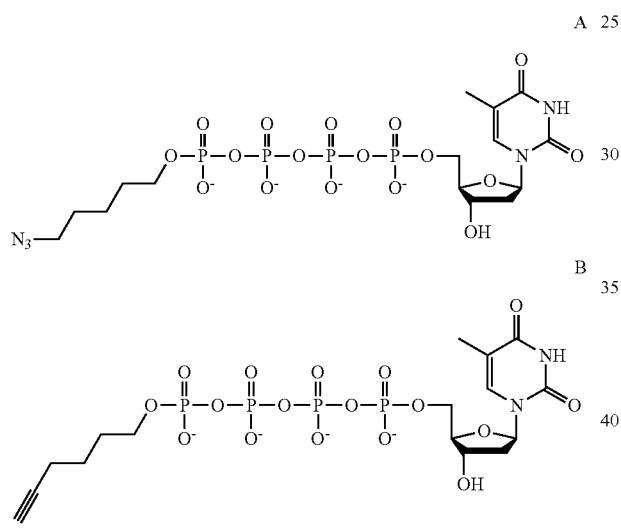

References on making and labeling tetraphosphate nucleotides include the following, the entire contents of each of which are incorporated by reference herein:

Kumar, S., A. Sood, J. Wegener, P. J. Finn, S. Nampalli, J. R. Nelson, A. Sekher, P. Mitsis, J. Macklin and C. W. Fuller, "Terminal phosphate labeled nucleotides: synthesis, applications, and linker effect on incorporation by DNA polymerases," *Nucleosides Nucleotides Nucleic Acids* 24(5-7): 401-408 (2005);

Sood, A., S. Kumar, S. Nampalli, J. R. Nelson, J. Macklin and C. W. Fuller, "Terminal phosphate-labeled nucleotides with improved substrate properties for homogeneous nucleic acid assays," *J Am Chem Soc* 127(8): 2394-2395 (2005);

Kumar, S., C. Tao, M. Chien, B. Hellner, A. Balijepalli, J. W. Robertson, Z. Li, J. J. Russo, J. E. Reiner, J. J. Kasianowicz and J. Ju, "PEG-labeled nucleotides and nanopore detection for single molecule DNA sequencing by synthesis," *Sci Rep* 2: 684 (8 pages) (2012);

Bonnac, L., S. E. Lee, G. T. Giuffredi, L. M. Elphick, A. A. Anderson, E. S. Child, D. J. Mann and V. Gouverneur, "Synthesis and O-phosphorylation of 3,3,4,4-tetrafluoro-aryl-C-nucleoside analogues," *Org Biomol Chem* 8(6): 1445-1454 (2010); and Lee, S. E., L. M. Elphick, A. A. Anderson, L. Bonnac, E. S. Child, D. J. Mann and V. Gouverneur, "Synthesis and reactivity of novel gamma-phosphate modified ATP analogues," *Bioorg Med Chem Lett* 19(14): 3804-3807 (2009).

Other Alternative Embodiments

While various illustrative embodiments of the invention are described above, it will be apparent to one skilled in the art that various changes and modifications may be made therein without departing from the invention. For example, although certain compositions, systems, and methods are discussed above with reference to sequencing polynucleotides such as DNA or RNA, it should be understood that the present compositions, systems, and methods suitably can be adapted for use in detecting any type of event, e.g., the motion of a molecule, or a portion thereof, that can be linked to the presence or motion of a reporter region adjacent to a constriction of a nanopore. The appended claims are intended to cover all such changes and modifications that fall within the true spirit and scope of the invention.

What is claimed:

1. A composition including:
a substrate having a first side and a second side,
a nanopore extending through the first and second sides of the substrate, wherein the nanopore has a diameter D1, and wherein nanopore comprises a constricting region that has a diameter D2 at the narrowest point, and wherein D2<D1,
a plurality of nucleotides, wherein each of the nucleotides comprises an elongated tag;
first and second polynucleotides, the first polynucleotide being complementary to the second polynucleotide;
a polymerase disposed adjacent to the first side of the nanopore, wherein the polymerase adds nucleotides of the plurality of nucleotides to the first polynucleotide based on a sequence of the second polynucleotide;
a permanent tether including a head region, a tail region, and an elongated body disposed therebetween, the head region being anchored to the polymerase, wherein the elongated body is disposed in the nanopore;
a first moiety disposed on the elongated body, wherein the first moiety is configured to bind to the elongated tag of a first nucleotide upon which the polymerase is acting; and
a reporter region disposed on the elongated body, wherein the reporter region is configured to indicate when the first nucleotide is complementary or is not complementary to a next nucleotide in the sequence of the second polynucleotide,
wherein the first moiety is configured to generate a first signal state responsive to the polymerase acting upon the first nucleotide, the first nucleotide being identifiable based on the first signal state, and
wherein the reporter region is configured to generate a second signal state when the first nucleotide is complementary or is not complementary to the next nucleotide of the second polynucleotide.

2. The composition of claim 1, wherein the reporter region disposed on the elongated body is located within the constricting region of the nanopore.

3. The composition of claim 1, wherein the elongated body and tail region do not extend beyond the second side of the substrate.

4. The composition of claim 1, wherein the tail region extends beyond the second side of the substrate.

5. The composition of claim 1, wherein the polymerase acting upon the first nucleotide comprises the polymerase binding the first nucleotide.

6. The composition of claim 1, wherein the first signal state includes an electrical or optical signal.

7. The composition of claim 1, wherein the reporter region is configured to generate the second signal state responsive to the polymerase successfully incorporating the first nucleotide into the first polynucleotide.

8. The composition of claim 1, wherein the reporter region is configured to generate the second signal state responsive to release of pyrophosphate responsive to the polymerase successfully incorporating the first nucleotide into the first polynucleotide.

9. The composition of claim 8, wherein the polymerase is modified so as to delay release of the pyrophosphate responsive to incorporation of the first nucleotide into the first polynucleotide.

10. The composition of claim 9, wherein the polymerase comprises a modified recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase.

11. The composition of claim 9, wherein the polymerase comprises a modified recombinant Φ29 DNA polymerase having at least one amino acid substitution or combination of substitutions selected from the group consisting of: an amino acid substitution at position 484, an amino acid substitution at position 198, and an amino acid substitution at position 381.

12. The composition of claim 9, wherein the polymerase comprises a modified recombinant Φ29 DNA polymerase having at least one amino acid substitution or combination of substitutions selected from the group consisting of E374Y, K512Y, T368F, A484E, A484Y, N387L, T372Q, T372L, K478Y, 1370 W, F198 W, and L381A.

13. The composition of claim 1, the reporter region being configured to generate the second signal state responsive to a conformational change of the polymerase.

14. The composition of claim 1, wherein the elongated tag comprises a first nucleotide sequence and the first moiety comprises a second nucleotide sequence that is complementary to the first nucleotide sequence.

15. A system including the composition of claim 14, and further including measurement circuitry configured to measure a first current or flux state through the nanopore.

16. The system of claim 15, wherein the first current or flux state is based on the elongated tag, the first nucleotide being identifiable based on the first current or flux state.

17. The system of claim 16, the measurement circuitry further being configured to measure a second current or flux state through the nanopore.

18. The system of claim 17, wherein the second current or flux state is based on a position of the reporter region within the aperture, it being determinable based on the second current or flux state whether the first nucleotide is complementary or is not complementary to the next nucleotide in the second polynucleotide.

19. The system of claim 17, further including a voltage source configured to apply a voltage across the first and second sides of the nanopore.

20. The system of claim 17, wherein the first moiety and the second moiety of the permanent tether are configured to dehybridize from one another responsive to the voltage in a two-step process.

21. A method including:
(a) providing a substrate having a first side, a second side, and a nanopore extending through the first and second sides of the substrate, wherein the nanopore has a diameter D1, and wherein nanopore comprises a constricting region that has a diameter D2 at the narrowest point, and wherein D2<D1,
(b) providing a plurality of nucleotides, wherein each of the nucleotides comprises an elongated tag;
(c) providing first and second polynucleotides, the first polynucleotide being complementary to the second polynucleotide;
(d) providing a polymerase disposed adjacent to the first side of the substrate, the polymerase configured to add nucleotides of the plurality of nucleotides to the first polynucleotide based on a sequence of the second polynucleotide, wherein the polymerase is anchored to a permanent tether including a head region, a tail region, and an elongated body disposed therebetween, the elongated body is disposed in the nanopore;
(e) determining that a first nucleotide is being acted upon by the polymerase based on binding of the elongated tag to a first moiety disposed on the elongated body; and (f) with a reporter region disposed on the elongated body, indicating when the first nucleotide is complementary or is not complementary to a next nucleotide in the sequence of the second polynucleotide, wherein the first moiety is configured to generate a first signal state responsive to the polymerase acting upon the first nucleotide, the first nucleotide being identifiable based on the first signal state, and wherein the reporter region is configured to generate a second signal state when the first nucleotide is complementary or is not complementary to the next nucleotide of the second polynucleotide.

* * * * *

UNITED STATES PATENT AND TRADEMARK OFFICE
CERTIFICATE OF CORRECTION

PATENT NO. : 11,970,734 B2
APPLICATION NO. : 16/870238
DATED : April 30, 2024
INVENTOR(S) : Kevin L. Gunderson and Jeffrey G. Mandell It is certified that error appears in the above-identified patent and that said Letters Patent is hereby corrected as shown below:

In the Claims

At Column 55, Line 8, delete "D2<D1," and insert -- D2<D1; --.

At Column 56, Line 13, delete "1370 W, F198 W," and insert -- 1370W, F198W, --.

At Column 56, Line 50, delete "D2<D1," and insert -- D2<D1; --.

Signed and Sealed this
Sixteenth Day of July, 2024

Katherine Kelly Vidal
Director of the United States Patent and Trademark Office

SEQUENCE LISTING

```
<160> NUMBER OF SEQ ID NOS: 1

<210> SEQ ID NO 1
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (12)..(12)
<223> OTHER INFORMATION: a, c, t or g

<400> SEQUENCE: 1
tttttttttt tnttttttta tatggg                                            26
```